US012017066B2

(12) United States Patent
Wang et al.

(10) Patent No.: US 12,017,066 B2
(45) Date of Patent: Jun. 25, 2024

(54) MODULATION OF EXTRACELLULAR VESICLES WITH ELECTRICAL STIMULATION

(71) Applicants: Mayo Foundation for Medical Education and Research, Rochester, MN (US); Regents of the University of Minnesota, Minneapolis, MN (US)

(72) Inventors: Hai-Long Wang, Rochester, MN (US); Gregory A. Worrell, Rochester, MN (US); Vanda A. Lennon, Rochester, MN (US); Haidong Dong, Rochester, MN (US); Lynn T. Bemis, Golden, CO (US); Richard G. Melvin, Duluth, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 541 days.

(21) Appl. No.: 16/771,323

(22) PCT Filed: Jan. 4, 2019

(86) PCT No.: PCT/US2019/012375

§ 371 (c)(1),
(2) Date: Jun. 10, 2020

(87) PCT Pub. No.: WO2019/136268

PCT Pub. Date: Jul. 11, 2019

(65) Prior Publication Data

US 2020/0384266 A1 Dec. 10, 2020

Related U.S. Application Data

(60) Provisional application No. 62/614,091, filed on Jan. 5, 2018.

(51) Int. Cl.

*A61N 1/36* (2006.01)
*A61K 9/00* (2006.01)
*A61K 31/7105* (2006.01)
*A61K 31/713* (2006.01)
*A61N 2/00* (2006.01)

(52) U.S. Cl.

CPC ...... *A61N 1/36002* (2017.08); *A61K 31/7105* (2013.01); *A61K 31/713* (2013.01); *A61N 2/002* (2013.01); *A61K 9/0019* (2013.01); *A61K 9/0043* (2013.01)

(58) Field of Classification Search

CPC ... A61N 1/36002; A61N 2/002; A61K 9/0019
USPC ............ 514/44 A; 435/6.1, 91.1, 91.31, 455, 435/458; 536/23.1, 24.5; 424/9.1
See application file for complete search history.

(56) References Cited

U.S. PATENT DOCUMENTS

| | | | |
|---|---|---|---|
| 2011/0137381 A1 | 6/2011 | Lee et al. |
| 2012/0083861 A1 | 4/2012 | Fried et al. |
| 2015/0216899 A1 | 8/2015 | Pusic et al. |
| 2016/0243171 A1 | 8/2016 | Shiels et al. |

FOREIGN PATENT DOCUMENTS

| | | |
|---|---|---|
| EP | 2715351 | 10/2016 |
| WO | WO 2012162563 | 11/2012 |

OTHER PUBLICATIONS

Dickens et al (Sci. Signal, vol. 10, eaai7696, pp. 1-12 (2017) (Year: 2017).*

Campbell et al (Medical Hypotheses, vol. 88, pp. 6-9 (2016)) (Year: 2016).*

Johnsen et al (Biochimica et Biophysica Acta, vol. 1846, pp. 75-87 (2014)) (Year: 2014).*

Kirson et al (PNAS, vol. 104, No. 24, pp. 10152-10157 (2007)) (Year: 2007).*

Gilligan et al (Int. J. Mol. Sci., vol. 18, 1122, pp. 1-12 (2017)) (Year: 2017).*

Abrahamsson et al., "Tissue specific expression of extracellular microRNA in human breast cancers and normal human breast tissue in vivo," Oncotarget, May 8, 2015, 6(26):22959-22969.

Anastassiou et al., "Ephaptic coupling of cortical neurons," Nat. Neuroscience, Feb. 2011, 14(2)217-224.

Applied Biomedical Engineering, 1st ed., Gargiulo et al., (eds.), Aug. 2011, Chapter 3, 28 pages.

Apweiler et al., "The InterPro database, an integrated documentation resource for protein families, domains and functional sites," Nucleic Acids Research, Jan. 2001, 29(1):37-40.

Arroyo et al., "Argonaute2 complexes carry a population of circulating microRNAs independent of vesicles in human plasma," Proc. Natl. Acad. Sci. USA, Mar. 22, 2011, 108(12):5003-5008.

Aspelund et al., "A dural lymphatic vascular system that drains brain interstitial fluid and macromolecules," J. Exp. Medicine, Jun. 2015, 212(7):991-999.

Bache et al., "Detection and quantification of microRNA in cerebral microdialysate," J. Transl. Medicine, May 7, 2015, 13:149, 10 pages.

Becker et al., "Extracellular Vesicles in Cancer: Cell-to-Cell Mediators of Metastasis," Cancer Cell, Dec. 12, 2016, 30(6):836-848.

Bell et al., "Epilepsy surgery outcomes in temporal lobe epilepsy with a normal MRI," Epilepsia, Sep. 2009, 50(9):2053-2060.

Bemis et al., "Distinct aerobic and hypoxic mechanisms of HIF-alpha regulation by CSN5," Genes & Development, Apr. 2004, 18(7):739-744.

(Continued)

*Primary Examiner* — Jane J Zara

(74) *Attorney, Agent, or Firm* — Fish & Richardson P.C.

(57) ABSTRACT

Methods for modulating the release and content of extracellular vesicles from target cells using electrical stimulation are provided. Compositions comprising extracellular vesicles or extracts of extracellular vesicles and methods of administering the compositions to a subject are also provided.

10 Claims, 12 Drawing Sheets

(56) References Cited

OTHER PUBLICATIONS

Bemis et al., "EGFR-mutant lung adenocarcinoma in a patient with Li-Fraumeni syndrome," Lancet Oncology, Jun. 2007, 8(6):559-560.
Bemis et al., "MicroRNA-137 Targets Microphthalmia-associated Transcription Factor Expression in Melanoma Cell Lines," Cancer Research, Mar. 1, 2008, 68(5):1362-1368.
Bergey et al., "Long-term treatment with responsive brain stimulation in adults with refractory partial seizures," Neurology, Feb. 24, 2015, 84(8):810-817.
Blouin et al., "Human hypocretin and melanin-concentrating hormone levels are linked to emotion and social interaction," Nat. Communications, Mar. 5, 2013, 4;1547, 9 pages.
Bower et al., "Evidence for Consolidation of Neuronal Assemblies after Seizures in Humans," J. Neuroscience, Jan. 21, 2015, 35(3):999-1010.
Bower et al., "Spatiotemporal neuronal correlates of seizure generation in focal epilepsy," Epilepsia, May 2012, 53(5):807-816.
Brinkmann et al., "Crowdsourcing reproducible seizure forecasting in human and canine epilepsy," Brain, Jun. 2016, 139(Pt 6):1713-1722.
Burkholder et al., "Interictal Scalp Electroencephalography and Intraoperative Electrocorticography in Magnetic Resonance Imaging-Negative Temporal Lobe Epilepsy Surgery," JAMA Neurology, Jun. 2014, 71(6):702-709.
Buzsaki et al., "High-frequency network oscillation in the hippocampus," Science, May 15, 1992, 256(5059):1025-1027.
Campbell et al., "Electrical stimulation to optimize cardioprotective exosomes from cardiac stem cells," Med. Hypotheses, Mar. 2016, 88:6-9.
Carlson et al., "Sex differences in seizure types and symptoms," Epilepsy & Behavior, Dec. 2014, 41:103-108.
Chamberlain et al., "Peripherin-IgG association with neurologic and endocrine autoimmunity," J. Autoimmunity, Jun. 2010, 34(4):469-477.
Chan et al., "ANNA-3 Anti-Neuronal Nuclear Antibody: Marker of Lung Cancer-Related Autoimmunity," Ann Neurology, Sep. 2001, 50(3):301-311.
Chan et al., "MicroRNA-21 is an antiapoptotic factor in human glioblastoma cells," Cancer Research, Jul. 15, 2005, 65(14):6029-6033.
Chen et al., "Anti-PD-1/PD-L1 therapy of human cancer: past, present, and future," J. Clin. Investigation, Sep. 2015, 125(9):3384-3391.
Chen et al., "Exosomal PD-LI Contributes to Immunosuppression and is Associated with Anti-PD-1. Response," Nature, Aug. 2018, 560(7718):382-386.
Chen et al., "Preparation of rodent primary cultures for neuron-glia, mixed glia, enriched microglia, and reconstituted cultures with microglia," Methods Mol. Biology, Jun. 2013, 1041:231-240.
Cho et al., "Brain Slices as Models for Neurodegenerative Disease and Screening Platforms to Identify Novel Therapeutics," Curr. Neuropharmacology, Mar. 2007, 5(1):19-33.
Christensen et al., "Gender Differences in Epilepsy," Epilepsia, Jun. 2005, 46(6):956-960.
Coles et al., "Feasibility study of a caregiver seizure alert system in canine epilepsy," Epilepsy Research, Oct. 2013, 106(3):456-460.
De Toro et al., "Emerging roles of exosomes in normal and pathological conditions: new insights for diagnosis and therapeutic applications," Front. Immunology, May 2015, 6:203, 12 pages.
DeAizpurua et al., "Antagonism of Voltage-gated Calcium Channels in Small Cell Carcinomas of Patients with and without Lambert-Eaton Myasthenic Syndrome by Autoantibodies, ω-Conotoxin and Adenosine," Cancer Research, Sep. 1, 1988, 48(17):4719-4724.
Deeb et al., "Proceedings of the Fourth Annual Deep Brain Stimulation Think Tank: A Review of Emerging Issues and Technologies," Front. Integr. Neuroscience, Nov. 2016, 10:38, 21 pages.
Deuschl et al., "A Randomized Trial of Deep-Brain Stimulation for Parkinson's Disease," N. Engl. J. Medicine, Aug. 31, 2006, 355(9):896-908.
Dickens et al., "Astrocyte-shed extracellular vesicles regulate the peripheral leukocyte response to inflammatory brain lesions," Sci. Signaling, Apr. 4, 2017, 10(473):eaai7696, 13 pages.
Dickson et al., "Cloning, Expression and Purification of a Functional Nonacetylated Mammalian Mitochondrial Chaperonin 10," J. Biol. Chemistry, Oct. 28, 1994, 269(43):26858-26864.
Diebel et al., "Beyond the Ribosome: Extra-translational Functions of tRNA Fragments," Biomark. Insights, Jan. 2016, 11(SI):1-8.
Dignan et al., "Successful Implementation of Genetic Education for Native Americans Workshops at National Conferences," Genetics, Feb. 2005, 169(2):517-521.
Dong et al., "Tumor-associated B7-H1 promotes T-cell apoptosis: A potential mechanism of immune evasion," Nature Medicine 8 (8). Nat. Medicine, Aug. 2002, 8(8):793-800.
Donson et al., "Pediatric Brainstem Gangliogliomas Show BRAFV600E Mutation in a High Percentage of Cases," Brain Pathology, Mar. 2014, 24(2):173-183.
El Andaloussi et al., "Extracellular vesicles: biology and emerging therapeutic opportunities," Nat. Rev. Drug Discovery, May 2013, 12(5):347-357.
Ezzyat et al. "Direct Brain Stimulation Modulates Encoding States and Memory Performance in Humans," Curr. Biology, May 8, 2017, 27(9):1251-1258.
Fang et al., "Autoimmune Glial Fibrillary Acidic Protein Astrocytopathy," JAMA Neurology, Nov. 2016, 73(11):1297-1307.
Fields et al., "New Insights into Neuron-Glia Communication," Science, Oct. 18, 2002, 298(5593):556-562.
Fisher et al., "Electrical stimulation of the anterior nucleus of thalamus for treatment of refractory epilepsy," Epilepsia, May 2010, 51(5):899-908.
Fisher, "Therapeutic Devices for Epilepsy," Ann. Neurology, Feb. 2012, 71(2):157-168.
Frigola et al., "Identification of a Soluble Form of B7-H1 that Retains Immunosuppressive Activity and is Associated with Aggressive Renal Cell Carcinoma," Clin. Cancer Research, Apr. 1, 2011, 17(7):1915-1923.
Furman et al., "Aquaporin-4 square array assembly: Opposing actions of MI and M23 isoforms," Proc. Natl. Acad. Sci. USA, Nov. 11, 2003, 100(23):13609-13614.
Gemmill et al., "The TRC8 hereditary kidney cancer gene suppresses growth and functions with VHL in a common pathway," Oncogene, May 16, 2002, 21(22):3507-3516.
Gilligan et al., "Engineering Exosomes for Cancer Therapy," Int. J. Mol. Sciences, May 24, 2017, 18(6):1122, 12 pages.
Gorter et al., "Hippocampal subregion-specific microRNA expression during epileptogenesis in experimental temporal lobe epilepsy," Neurobiol. Disease, Feb. 2014, 62:508-520.
Hansen et al., "An Ion Selectivity Filter in the Extracellular Domain of Cys-loop Receptors Reveals Determinants for Ion Conductance," J. Biol. Chemistry, Dec. 26, 2008, 283(52):36066-36070.
Hatzel et al., "Identification of heat shock protein 10 within the equine embryo, endometrium, and maternal peripheral blood mononuclear cells," Theriogenology, Mar. 2015, 83(5):832-839.
He et al., "MiR-21 is required for anti-tumor immune response in mice: an implication for its bi-directional roles," Oncogene, Mar. 27, 2017, 36(29):4212-4223.
Heck et al., "Two-year seizure reduction in adults with medically intractable partial onset epilepsy treated with responsive neurostimulation: Final results of the RNS System Pivotal trial," Epilepsia, Mar. 2014, 55(3):432-441.
Hiroaki et al., "Implications of the Aquaporin-4 Structure on Array Formation and Cell Adhesion," J. Mol. Biology, Jan. 27, 2006, 355(4):628-639.
Howbert et al., "Forecasting seizures in dogs with naturally occurring epilepsy," PLoS One, Jan. 8, 2014, 9(1):e81920, 8 pages.
Jacobs et al., "Direct Electrical Stimulation of the Human Entorhinal Region and Hippocampus Impairs Memory," Neuron, Dec. 7, 2016, 92(5):983-990.
Jimenez-Mateos et al., "Epilepsy and microRNA," Neuroscience, May 2013, 238:218-229.

(56) References Cited

OTHER PUBLICATIONS

Kamondi et al., "Theta Oscillations in Somata and Dendrites of Hippocampal Pyramidal Cells In Vivo: Activity-Dependent Phase-Precession of Action Potentials," Hippocampus, Dec. 7, 1998, 8(3):244-261.
Kanai et al., "Blockade of B7-H1 Suppresses the Development of Chronic Intestinal Inflammation," J. Immunology, Oct. 15, 2003, 171(8):4156-4163.
Kile et al., "Low frequency stimulation decreases seizure activity in a mutation model of epilepsy," Epilepsia, Sep. 2010, 51(9):1745-1753.
Kirson et al., "Alternating electric fields arrest cell proliferation in animal tumor models and human brain tumors," Proc. Natl. Acad. Sci. USA, Jun. 12, 2007, 104(24):10152-10157.
Koubeissi et al., "Electrical stimulation of a small brain area reversibly disrupts consciousness," Epilepsy & Behavior, Aug. 2014, 37:32-35.
Kremen et al., "Behavioral state classification in epileptic brain using intracranial electrophysiology," J. Neural Engineering, Apr. 2017, 14(2):026001, 9 pages.
Kucewicz et al., "Evidence for verbal memory enhancement with electrical brain stimulation in the lateral temporal cortex," Brain, Apr. 2018, 141(4):971-978.
Kucewicz et al., "High frequency oscillations are associated with cognitive processing in human memory," Brain, Aug. 2014, 137(PT 8):2231-2244.
Lafourcade et al., "MiRNAs in Astrocyte-Derived Exosomes as Possible Mediators of Neuronal Plasticity," J. Exp. Neuroscience, Aug. 2016, 10(S1):1-9.
Langevin et al., "Deep Brain Stimulation of the Basolateral Amygdala for Treatment-Refractory Posttraumatic Stress Disorder," Biol. Psychiatry, May 15, 2016, 79(10):E82-E84.
Latchman et al., "PD-L2 is a second ligand for PD-1 and inhibits T cell activation," Nat. Immunology, Mar. 2001, 2(3):261-268.
Laxton et al., "A phase I trial of deep brain stimulation of memory circuits in Alzheimer's disease," Ann. Neurology, Oct. 2010, 68(4):521-534.
Lennon et al., "Calcium-channel Antibodies in Lambert-Eaton Syndrome and Other Paraneoplastic Syndromes," N. Engl. J. Medicine, Jun. 1, 1995, 332(22):1467-1474.
Lennon et al., "Enteric Neuronal Autoantibodies in Pseudoobstruction With Small-cell Lung Carcinoma," Gastroenterology, Jan. 1991, 100(1):137-142.
Lennon et al., "Experimental Autoimmune Myasthenia: A Model of Myasthenia Gravis in Rats and Guinea Pigs," J. Exp. Medicine, Jun. 1975, 141(6):1365-1375.
Lennon et al., "IgG marker of optic-spinal multiple sclerosis binds to the aquaporin-4 water channel," J. Exp. Medicine, Aug. 2002, 202(4):473-477.
Lennon et al., "Immunization with neuronal nicotinic acetylcholine receptor induces neurological autoimmune disease," J. Clin. Investigation, Mar. 2003, 111(6):907-913.
Lennon et al., "Immunopharmacological Disease: A Break in Tolerance to Receptor Sites," Lancet, Mar. 27, 1971, 1(7700):630-633.
Lennon et al., "Myasthenia gravis induced by monoclonal antibodies to acetylcholine receptors," Nature, May 22, 1980, 285(5762):238-240.
Li et al., "MicroRNAs dysregulation in epilepsy," Brain Research, Oct. 2014, 1584:94-104.
Li et al., "Therapeutic targeting of microRNAs: current status and future challenges," Nat. Rev. Drug Discovery, Aug. 2014, 13(8):622-638.
Liu et al., "B7-H1 antibodies lose antitumor activity due to activation of p38 MAPK that leads to apoptosis of tumor-reactive CD8 + T cells," Sci. Reports, Nov. 8, 2016, 6:36722, 10 pages.
Lochhead et al., "Intranasal delivery of biologics to the central nervous system," Adv. Drug Deliv. Reviews, May 2015, 64(7):614-628.
Lozano et al., "A Phase II Study of Fornix Deep Brain Stimulation in Mild Alzheimer's Disease," J. Alzheimer's Disease, Sep. 2016, 54(2):777-787.
Lundstrom et al., "Chronic Subthreshold Cortical Stimulation to Treat Focal Epilepsy," JAMA Neurology, Nov. 2016, 73(11):1370-1372.
Lundstrom et al., "Chronic subthreshold cortical stimulation: a therapeutic and potentially restorative therapy for focal epilepsy," Expert Rev. Neurotherapeutics, Jul. 2017, 17(7):661-666.
Macy et al., "Clinical and molecular characteristics of congenital glioblastoma," Neuro-Oncology, Jul. 2012, 14(7):931-941.
Manthey et al., "Using Electrical Stimulation to Enhance the Efficacy of Cell Transplantation Therapies for Neurodegenerative Retinal Diseases: Concepts, Challenges, and Future Perspectives," Cell Transplantation, Feb. 3, 2017, 26(6):949-965.
Matsumoto et al., "Network oscillations modulate interictal epileptiform spike rate during human memory," Brain, Aug. 2013, 136(Pt 8):2444-2456.
Matsumoto et al., "Pathological and physiological high-frequency oscillations in focal human epilepsy:" J. Neurophysiology, Oct. 2013, 110(8):1958-1964.
Mayberg et al., "Deep Brain Stimulation for Treatment-Resistant Depression," Neuron, Mar. 3, 2005, 45(5):651-660.
Milone et al., "Mode Switching Kinetics Produced by a Naturally Occurring Mutation in the Cytoplasmic Loop of the Human Acetylcholine Receptor epsilon Subunit," Neuron, Mar. 1998, 20(3):575-588.
Moldovan et al., "The treatment of Parkinson's disease with deep brain stimulation: current issues," Neural Regen. Research, Jul. 2015, 10(7):1018-1022.
Monai et al., "Astrocytes as a target of transcranial direct current stimulation (tDCS) to treat depression," Neurosci. Research, Jan. 2018, 126:15-21.
Monai et al., "Astrocytic calcium activation in a mouse model of tDCS-Extended discussion," Neurogenesis, Sep. 2016, 3(1):e1240055, 7 pages.
Natale et al., "Activation of G protein-coupled estrogen receptor signaling inhibits melanoma and improves response to immune checkpoint blockade," eLife, Jan. 16, 2018, 7:e31770, 19 pages.
Nedergaard et al., "New roles for astrocytes: Redefining the functional architecture of the brain," Trends in Neuroscience, Oct. 2003, 26(10):523-530.
Nitsche et al., "Transcranial direct current stimulation: State of the art 2008," Brain Stimulation, Jul. 2008, 1(3):206-223.
Noe et al., "Long-term Outcomes After Nonlesional Extratemporal Lobe Epilepsy Surgery," JAMA Neurology, Aug. 2013, 70(8):1003-1008.
Nolte-'t et al., "Immune Cell-derived Vesicles: Modulators and Mediators of Inflammation," Curr. Pharm. Design, Apr. 2012, 18(16):2357-2368.
Nordin et al., "Ultrafiltration with size-exclusion liquid chromatography for high yield isolation of extracellular vesicles preserving intact biophysical and functional properties," Nanomedicine: Nanotech. Biol. Medicine, May 2015, 11(4):879-883.
Oguro-Okano et al., "Molecular Diversity of Neuronal-Type Calcium Channels Identified in Small Cell Lung Carcinoma," Mayo Clin. Proceedings, Dec. 1992, 67(12):1150-1159.
Papadopoulos et al., "Aquaporins and cell migration," Pjlugers Arch. Eur. J. Physiology, Jul. 2008, 456(4):693-700.
Parish et al., "Long-Range Temporal Correlations in Epileptogenic and Non-Epileptogenic Human Hippocampus," Neuroscience, 2004, 125(4):1069-1076.
Patel et al., "PD-L1 Expression as a Predictive Biomarker in Cancer Immunotherapy," Mol. Cancer Therapeutics, Apr. 2015, 14(4):847-856.
PCT International Preliminary Report on Patentability in International Appln. No. PCT/US2019/012375, dated Jul. 7, 2020, 20 pages.
PCT International Search Report and Written Opinion in International Appln. No. PCT/US2019/012375, dated Apr. 1, 2019, 23 pages.

(56) References Cited

OTHER PUBLICATIONS

Peng et al., "Expression Patterns of miR-124, miR-134, miR-132, and miR-21 in an Immature Rat Model and Children with Mesial Temporal Lobe Epilepsy," J. Mol. Neuroscience, Jun. 2013, 50(2):291-297.
Peng et al., "MicroRNA delivery for regenerative medicine," Adv. Drug Deliv. Reviews, Jul. 2015, 88:108-122.
Perea et al., "Neuron-glia networks: integral gear of brain function," Front. Cell. Neuroscience, Nov. 6, 2014, 8:378, 8 pages.
Perkel, "Membrane messengers: Extracellular vesicles," Science, Jun. 10, 2016, 352(6291):1349-1351.
Pittock et al., "Aquaporin-4 autoantibodies in a paraneoplastic context," Arch. Neurology, May 2008, 65(5):629-632.
Pittock et al., "Eculizumab in AQP4-IgG-positive relapsing neuromyelitis optica spectrum disorders: an open-label pilot study," Lancet Neurology, Jun. 2013, 12(6):554-562.
Rattay, "The Basic Mechanism for the Electrical Stimulation of the Nervous System," Neuroscience, Mar. 1999, 89(2):335-346.
Raymaekers et al., "Deep brain stimulation for treatment-resistant major depressive disorder: a comparison of two targets and long-term follow-up," Transl. Psychiatry, Oct. 31, 2017, 7(10):e1251, 8 pages.
Reuland et al., "MicroRNA-26a is Strongly Downregulated in Melanoma and Induces Cell Death through Repression of Silencer of Death Domains (SODD)," J. Invest. Dermatology, May 2013, 133(5):1286-1293.
Rodrigues et al., "Role of Extracellular Vesicles in Viral and Bacterial Infections: Pathogenesis, Diagnostics, and Therapeutics," Theranostics, Apr. 9, 2018, 8(10):2709-2721.
Roos et al., "miR-146a-mediated suppression of the inflammatory response in human adipocytes," Sci. Reports, Dec. 6, 2016, 6:38339, 11 pages.
Ru et al., "The multiMiR R package and database: integration of microRNA-target interactions along with their disease and drug associations," Nucleic Acids Research, Jul. 25, 2014, 42(17):e133, 10 pages.
Rufino-Ramos et al., "Extracellular vesicles: Novel promising delivery systems for therapy of brain diseases," J. Control. Release, Sep. 28, 2017, 262:247-258.
Sciamanna et al., "Nicotinic Acetylcholine Receptors of Muscle and Nuronal (a7) Types Coexpressed in a Small Cell Lung Carcinoma," J. Neurochemistry, Dec. 1997, 69(6):2302-2311.
Seifert et al., "A method to distinguish morphologically similar Peromyscus species using extracellular RNA and high-resolution melt analysis," Anal. Biochemistry, Sep. 1, 2016, 508:65-72.
Shen et al., "Protein Targeting to Exosomes/Microvesicles by Plasma Membrane Anchors," J. Biol. Chemistry, Apr. 22, 2011, 286(16):14383-14395.
Soreq et al., "Deep brain stimulation modulates nonsense-mediated RNA decay in Parkinson's patients leukocytes," BMC Genomics, Jul. 2013, 14:478.
Srivastava et al., "Role of inflammation and its miRNA based regulation in epilepsy: Implications for therapy," Clin. Chim. Acta, Jan. 15, 2016, 452:1-9.
Stead et al., "Microseizures and the spatiotemporal scales of human partial epilepsy," Brain. Sep. 2010, 133(9):2789-2797.
Stupp et al., "NovoTTF-100A versus physician's choice chemotherapy in recurrent glioblastoma: A randomised phase III trial of a novel treatment modality," Eur. J. Cancer, Sep. 2012, 48(14):2192-2202.
Takeda et al., "Novel Microdialysis Method to Assess Neuropeptides and Large Molecules in Free-moving Mouse," Neuroscience, Jul. 14, 2011, 186:110-119.
Theodoraki et al., "Clinical Significance of PD-L1+ Exosomes in Plasma of Head and Neck Cancer Patients," Clin. Cancer Research, Dec. 12, 2017, 24(4):896-905.
Thieben et al., "Potentially reversible autoimmune limbic encephalitis with neuronal potassium channel antibody," Neurology, Apr. 2004, 62(7):1177-1182.
Toprani et al., "Long-lasting hyperpolarization underlies seizure reduction by low frequency deep brain electrical stimulation," J. Physiology, Nov. 2013, 591(22):5765-5790.
Turpin et al., "Role of extracellular vesicles in autoimmune diseases," Autoimmun. Reviews, Feb. 2016, 15(2):174-183.
van der Vlist et al., "CD4+ T cell activation promotes the differential release of distinct populations of nanosized vesicles," J. Extracell. Vesicles, Apr. 16, 2012, 1:18364, 9 pages.
Van Gompel et al., "Increased cortical extracellular adenosine correlates with seizure termination," Epilepsia, Feb. 2014, 55(2):233-244.
Vernino et al., "Autoantibodies to Ganglionic Acetylcholine Receptors in Autoimmune Autonomic Neuropathies," N. Engl. J. Medicine, Sep. 21, 2000, 343(12):847-855.
Vernino et al., "New Purkinje Cell Antibody (PCA-2): Marker of Lung Cancer-Related Neurological Autoimmunity," Ann. Neurology, Mar. 2000, 47(3):297-305.
Vickers et al., "MicroRNAs are transported in plasma and delivered to recipient cells by high-density lipoproteins," Nat. Cell Biology, Mar. 20, 2011, 13(4):423-443.
Wang et al., "Acetylcholine receptor M3 domain: stereochemical and volume contributions to channel gating," Nat. Neuroscience, Mar. 1999, 2(3):226-233.
Wang et al., "Control of Cation Permeation through the Nicotinic Receptor Channel," PLoS Comput. Biology, Feb. 2008, 4(2):e41, 9 pages.
Wang et al., "Curariform Antagonists Bind in Different Orientations to the Nicotinic Receptor Ligand Binding Domain," J. Biol. Chemistry, Aug. 22, 2003, 278(34):32284-32291.
Wang et al., "Export of microRNAs and microRNA-protective protein by mammalian cells," Nucleic Acids Research, Nov. 2010, 38(20):7248-7259.
Wang et al., "Fundamental Gating Mechanism of Nicotinic Receptor Channel Revealed by Mutation Causing a Congenital Myasthenic Syndrome," J. Gen, Physiology, Sep. 2000, 116(3):449-462.
Wang et al., "Intramembrane Proton Binding Site Linked to Activation of Bacterial Pentameric Ion Channel," J. Biol. Chemistry, Feb. 24, 2012, 287(9):6482-6489.
Wang et al., "Mutation in the M1 Domain of the Acetylcholine Receptor alpha Subunit Decreases the Rate of Agonist Dissociation," J. Gen. Physiology, Jun. 1997, 109(6):757-766.
Wang et al., "Single-Channel Current Through Nicotinic Receptor Produced by Closure of Binding Site C-Loop," Biophysical Journal, May 2009, 96(9):3582-3590.
Wang et al., "TNF-alpha promotes extracellular vesicle release in mouse astrocytes through glutaminase," J. Neuroinflammation, Apr. 20, 2017, 14:87, 10 pages.
Wass et al., "The Effects of Remifentanil on Epileptiform Discharges during Intraoperative Electrocorticography in Patients Undergoing Epilepsy Surgery," Epilepsia, Oct. 2001, 42(10):1340-1344.
Weiss et al., "Field effects in the CNS play functional roles," Front. Neural Circuits, May 18, 2010, 4:15, 10 pages.
Williams et al., "Activation of M3 Muscarinic Acetylcholine Receptors Inhibits Voltage-dependent Calcium Influx in Small Cell Lung Carcinoma," J. Biol. Chemistry, Jan. 25, 1990, 265(3):1443-1447.
Witwer et al., "Standardization of sample collection, isolation and analysis methods in extracellular vesicle research," J. Extracell. Vesicles, May 27, 2013, 2:20360, 25 pages.
Worrell et al., "Evidence for self-organized criticality in human epileptic hippocampus," NeuroReport, Nov. 15, 2002, 13(16):2017-2021.
Worrell et al., "High-frequency oscillations and other electrophysiological biomarkers of epilepsy: clinical studies," Biomark. Medicine, Oct. 2011, 5(5):557-566.
Worrell et al., "High-frequency oscillations and seizure generation in neocortical epilepsy." Brain, Jul. 2004, 127(Pt 7):1496-1506.
Worrell et al., "Recording and analysis techniques for high-frequency oscillations," Prog. Neurobiology, Sep. 2012, 98(3):265-278.
Worrell et al., "Virial expansion of a quantum particle in a classical gas: Application to the orthopositronium decay rate," Phys. Rev. A, Apr. 1996, 53(4):2101-2107.

(56) References Cited

OTHER PUBLICATIONS

Yamada et al., "In Vivo Microdialysis Reveals Age-Dependent Decrease of Brain Interstitial Fluid Tau Levels in P301S Human Tau Transgenic Mice," J. Neuroscience, Sep. 14, 2011, 31(37):13110-13117.
Yan et al., "Altered microRNA profiles in plasma exosomes from mesial temporal lobe epilepsy with hippocampal sclerosis," Oncotarget, Jan. 2017, 8(3):4136-4146.
Yanez-Mo et al., "Biological properties of extracellular vesicles and their physiological functions," J. Extracell. Vesicles, May 14, 2015, 4:27066, 60 pages.
Yang et al., "Evaluating glymphatic pathway function utilizing clinically relevant intrathecal infusion of CSF tracer," J. Transl. Medicine, May 2013, 11:107, 9 pages.
Yang et al., "miR-125b Regulation of Androgen Receptor Signaling Via Modulation of the Receptor Complex Co-Repressor NCOR2," BioResearch Open Access, Apr. 2012, 1(2):55-62.
Yongjun et al., "Abstract 17819: Electrical Stimulation Enhances Stem Cells-Mediated Angiogenesis via Exosomes," Circulation, Nov. 11, 2016, 134:A17819.
Yu et al., "CRMP-5 Neuronal Autoantibody: Marker of Lung Cancer and Thymoma-Related Autoimmunity," Ann. Neurology, Feb. 2001, 49(2):146-154.
Yu et al., "Exosomes as miRNA carriers: Formation-Function-Future," Int. J. Mol. Sciences, Dec. 2016, 17(12):2028, 12 pages.
Zekeridou et al., "Aquaporin-4 autoimmunity," Neurol. Neuroimmunol. Neuroinflammation, May 2015, 2(4):e110.
Zhao et al., "MicroRNA-146a acts as a guardian of the quality and longevity of hematopoietic stem cells in mice," eLife, May 2013, 2:e00537, 24 pages.
Zhou et al., "A method for extracting and characterizing RNA from urine: For downstream PCR and RNAseq analysis," Anal. Biochemistry, Nov. 2017, 536:8-15.
Zhou et al., "A tRNA Fragment, tRF5-Glu, regulates BCAR3 expression and proliferation in ovarian cancer cells," Oncotarget, Sep. 2017, 8(56):95377-95391.
Lamichhane et al., "Exogenous DNA Loading into Extracellular Vesicles via Electroporation is Size-Dependent and Enables Limited Gene Delivery," Mol. Pharm., Oct. 2015, 12(10):3650-3657.
Wang et al., "Programmable Modulation for Extracellular Vesicles," bioRxiv, Mar. 2019, 15 pages, doi: 10.1101/566448.

* cited by examiner

Use direct conjugated H1A –Alexa 488

MODULATION OF EXTRACELLULAR VESICLES WITH ELECTRICAL STIMULATION

CROSS-REFERENCE TO RELATED APPLICATIONS

This application is a National Stage application under 35 U.S.C. § 371 of International Application No. PCT/US2019/012375, having an International Filing Date of Jan. 4, 2019, which claims priority to U.S. Application Ser. No. 62/614,091, filed on Jan. 5, 2018. The disclosure of the prior application is considered part of the disclosure of this application, and is incorporated in its entirety into this application.

TECHNICAL FIELD

This invention relates to the production and modification of extracellular vesicles and their contents by electrical stimulation, and methods and compositions for using produced extracellular vesicles and their contents.

BACKGROUND

Every living cell releases extracellular vesicles that are critical for cellular signaling and a wide range of biological functions. Extracellular vesicles (EVs) are small membrane surrounded vesicles secreted from all cell types and widely distributed in blood, urine, milk, and other bodily fluids. EVs function as mediators of signaling, carrying a broad range of bioactive molecules between cells[53]. Studies have suggested both physiological and potentially pathological roles of EVs in viral infection[80], cancer spread[81], autoimmunity[82] and neurodegenerative diseases[83]. EVs transfer their cargos (proteins, lipids and RNAs) in both a paracrine manner (to adjacent target cells) and an endocrine manner (to distant target cells)[84].

SUMMARY

The present invention is generally directed to the release of extracellular vesicles (EVs) from one or more target cells and more specifically directed to modulating the release and contents of EVs from target cells using electrical stimulation.

In one aspect, a method of increasing or decreasing the amount of one or more cargo molecules present in or on the surface of an extracellular vesicle derived from a target cell is provided, the method including electrically stimulating the target cell, wherein the amount of the one or more cargo molecules is increased or decreased as compared to the amount of the one or more cargo molecules present inside or on the surface of an extracellular vesicle of the same or same type of target cell produced without electrical stimulation. In some cases, electrically stimulating the target cell can include applying an electrical field to the target cell at a frequency of between about 0.001 Hz to about 1000 Hz at about 0.002 mV/mm to about 5 mV/mm for about 1 to about 5 minutes.

In some cases, the method can optionally include one or more of the following features. The electric field can be a uniform electric potential field. Electrically stimulating the target cell can include applying patterned pulses. Stimulating the target cell can include stimulating an organ or portion of an organ containing said target cell. Stimulating the target cell can include stimulating a brain slice in vitro. The target cell can be a cultured cell. The target cell can be an electrically silent cell. The target cell can be a glial cell. The target cell can be an astrocyte.

In some cases, the method can optionally include one or more of the following features. The electric field can be a uniform electric potential field. Electrically stimulating the target cell can include applying patterned pulses.

In some cases, the cargo molecule can be PD-L1. In some cases of the method, an amount of PD-L1 is decreased as compared to an amount of PD-L1 present inside or on the surface of an extracellular vesicle of the same or same type of target cell produced without electrical stimulation.

In some cases, the extracellular vesicles are extracellular vesicles carrying PD-L1.

In another aspect, a method for modulating the release and cargo content of extracellular vesicles from a target cell is provided, the method including electrically stimulating the target cell. In some cases, electrically stimulating the target cell can include applying an electrical field to the target cell at a frequency of between about 0.001 Hz to about 1000 Hz at about 0.002 mV/mm to about 5 mV/mm for about 1 to about 5 minutes.

In some cases, modulating the release of extracellular vesicles can include decreasing the amount of extracellular vesicles carrying PD-L1 released from the target cell as compared to an amount of extracellular vesicles carrying PD-L1 released from the same target cell or target cell type without electrical stimulation.

In some cases, modulating the cargo content of extracellular vesicles can include decreasing the amount of PD-L1 inside or on the surface of extracellular vesicles released from the target cell an as compared to an amount of PD-L1 inside or on the surface of extracellular vesicles released from the target cell or target cell type without electrical stimulation.

In some cases, the target cell can be selected from the group consisting of a renal cell, a breast cell, and a glial cell. In some cases, the target cell can be a cancer cell.

In another aspect, a method is provided for reducing exosomal PD-L1 derived from one or more target cells, or present in a target tissue or an extracellular milieu surrounding one or more target cells, the method including electrically stimulating the one or more target cells, at least a portion of the target tissue or target tissue region containing at least a portion of the target cells or target tissue.

In some cases, electrically stimulating the one or more target cells, at least a portion of the target tissue or target tissue region containing at least a portion of the target cells or target tissue can include applying an electrical field to the target cell at a frequency of between about 0.001 Hz to about 1000 Hz at about 0.002 mV/mm to about 5 mV/mm for about 1 to about 5 minutes.

In some cases, electrically stimulating the one or more target cells, at least a portion of the target tissue or target tissue region containing at least a portion of the target cells or target tissue can include applying an electrical field to the target cell at a frequency of about 200 Hz at about 5 mV/mm for about 5 minutes.

In some cases, electrically stimulating the one or more target cells, at least a portion of the target tissue or target tissue region containing at least a portion of the target cells or target tissue can include applying an electrical field to the target cell at a frequency of about 20 Hz at about 5 mV/mm for about 5 minutes.

In some cases, the electric field can be a uniform electric potential field. In some cases, electrically stimulating the one or more target cells, at least a portion of the target tissue or target tissue region containing at least a portion of the target cells or target tissue can include applying patterned pulses.

In another aspect, a method is provided for treating cancer in a subject having a tumor, the method including electrically stimulating at least a portion of the tumor or a portion of the subject containing the tumor.

In another aspect, a method is provided for reducing spread of a tumor in a subject having the tumor, the method including electrically stimulating at least a portion of the tumor or a portion of the subject containing the tumor.

In some cases of one or more of the methods, electrically stimulating at least a portion of the tumor or a portion of the subject containing the tumor can optionally include applying an electrical field to the target cell at a frequency of between about 0.001 Hz to about 1000 Hz at about 0.002 mV/mm to about 5 mV/mm for about 1 to about 5 minutes. In some cases of these methods, electrically stimulating at least a portion of the tumor or a portion of the subject containing the tumor can include applying an electrical field to the target cell at a frequency of about 200 Hz at about 5 mV/mm for about 5 minutes. In some cases of these methods, electrically stimulating at least a portion of the tumor or a portion of the subject containing the tumor can include applying an electrical field to the target cell at a frequency of about 20 Hz at about 5 mV/mm for about 5 minutes.

In some cases of one or more of the methods, the electric field can be a uniform electric potential field. In some cases of these methods, electrically stimulating at least a portion of the tumor or a portion of the subject containing the tumor can include applying patterned pulses.

In some cases of one or more of the methods, the methods can optionally include one or more of the following features. The tumor can be a solid tumor. The tumor can be a breast adenocarcinoma, a renal adenocarcinoma, or a glioblastoma. An amount of PD-L1 present inside or on the surface of an extracellular vesicle produced by one or more cells of the tumor can be decreased as compared to the amount of PD-L1 present inside or on the surface of an extracellular vesicle of the same or same type of cell produced without electrical stimulation. An amount of exosomal PD-L1 present in or around the tumor can be decreased as compared to the amount of PD-L1 present in or around the same or same type of tumor without electrical stimulation In some cases of one or more of the methods, the method can further include administering to the subject one or more additional therapies before, during, or after the electrical stimulation. In some cases, the one or more additional therapies can be selected from the group consisting of chemotherapy, radiation therapy, and immunotherapy. In some cases, the chemotherapy can include administering a chemotherapeutic agent selected from the group consisting of doxorubicin, paclitaxel, cyclophosphamide, and combinations thereof.

In another aspect, a method of generating extracellular vesicles from one or more electrically silent cells is provided, the method including electrically stimulating the cell. In some cases, electrically stimulating the target cell can include applying an electrical field to the target cell at a frequency of between about 0.001 Hz to about 1000 Hz at about 0.002 mV/mm to about 5 mV/mm for about 1 to about 5 minutes.

In some cases, the method can optionally include one or more of the following features. The electric field can be a uniform electric potential field. Electrically stimulating the target cell can include applying patterned pulses. The electrically silent cell can be a glial cell. The electrically silent cell can be an astrocyte. In another aspect, a method of increasing content of one or more miRNAs in extracellular vesicles released from a target cell is provided, the method including electrically stimulating the target cell, wherein the content of the one or more miRNAs is increased as compared to the amount of the one or more miRNAs present inside or on the surface of an extracellular vesicle of the same or same type of target cell produced without electrical stimulation. In some cases, electrically stimulating the target cell can include applying an electrical field to the target cell at a frequency of between about 0.001 Hz to about 1000 Hz at about 0.002 mV/mm to about 5 mV/mm for about 1 to about 5 minutes.

In some cases, the method can optionally include one or more of the following features. The electric field can be a uniform electric potential field. Electrically stimulating the target cell can include applying patterned pulses. The one or more miRNAs can be selected from miR-21, miR-146, miR-423-5p, miR-4700-5p, miR-181a-5p, miR-92b-3p, miR-99b-5p, miR-320b, miR-23b-3p, miR-125b-5p, miR-27b-3p, miR-21-5p, miR-184, miR-23a-3p, miR-203a-3p, miR-125a-3p, miR-22-3p, miR-320a-3p, miR-103a-3p, miR-10a-5p, miR-27a-3p, miR-7704, miR-107, miR-148a-3p, miR-25-3p, miR-let-7f-5p, miR-221-3p, miR-4492, miR-let-7i-5p, miR-let-7a-5p, miR-92a-3p, let-7c-5p, 125a-5p, 10b-5p, 151a-3p, 28-3p, 191-5p, miR-7977, miR-130a-3p, miR-143-3p, miR-26a-5p, miR-100-5p, miR-3168, miR-1469, miR-4680-3p, miR-4259, miR-205-5p, miR-3195, miR-let-7b-5p, miR-30a-5p, miR-30d-5p, miR-375-3p, miR-183-5p, miR-146b-5p, miR-378a-3p, miR-26b-5p, miR-9-5p, miR-222-3p, miR-423-3p, miR-744-5p, miR-99a-5p, miR-4775, miR-4324, miR-662, miR-4781-3p, miR-5100, miR-361-5p, miR-125b-1-3p, miR-30d-3p, miR-125b-2-3p, miR-193b-3p, miR-141-3p, miR-24-3p, miR-5047, miR-21-3p, miR-129-5p, miR-151a-5p, miR-30a-3p, miR-210-3p, miR-6728-5p, miR-204-5p, miR-30e-5p, miR-98-5p, miR-186-5p, miR-486-5p, miR-10395-3p, miR-431-5p, miR-148b-5p, miR-182-5p, miR-3661, miR-6068, and combinations thereof. The target cell can be an astrocyte.

In another aspect, a method of producing extracellular vesicles derived from astrocytes is provided, the method including obtaining the astrocytes; culturing the astrocytes; and electrically stimulating the astrocytes. In some cases, electrically stimulating the target cell can include applying an electrical field to the target cell at a frequency of between about 0.001 Hz to about 1000 Hz at about 0.002 mV/mm to about 5 mV/mm for about 1 to about 5 minutes.

In some cases, the method can optionally include one or more of the following features. The electric field can be a uniform electric potential field. Electrically stimulating the target cell can include applying patterned pulses. Obtaining the astrocytes can include harvesting the astrocytes from brain tissue or from patient-derived Induced Pluripotent Stem Cells (iPSC). Culturing the astrocytes can include culturing the astrocytes for a time period of from about 21 days to about 28 days.

In some cases, the method can further include washing the astrocytes prior to the step of electrically stimulating the astrocytes. In some cases, the method can further include collecting extracellular vesicles released after the step of electrically stimulating the astrocytes.

In another aspect, a composition is provided, the composition including one or more modified extracellular vesicles or an extract from one or more modified extracellular vesicles, wherein the modified extracellular vesicles are produced by electrical stimulation of a target cell, and wherein the one or more modified extracellular vesicles or the extract from one or more modified extracellular vesicles contain one or more cargo molecules in an amount that is greater or lesser than the amount of the one or more cargo molecules present inside or on the surface of an extracellular vesicle from the same cell or an extract of one or more extracellular vesicles from the same cell produced without electrical stimulation. In some cases, the one or more cargo molecules can be selected from a protein, a lipids, an mRNAs, and an miRNA. In some cases, the one or more cargo molecules can be an miRNA. In some cases, the production of extracellular vesicles can be tuned to produce extracellular vesicles that carry a specific set of miRNAs.

In another aspect, a method of stimulating the brain of a subject is provided, the method including delivering to the subject a composition including one or more modified extracellular vesicles or an extract from one or more modified extracellular vesicles, wherein the modified extracellular vesicles are produced by electrical stimulation of a target cell, and wherein the one or more modified extracellular vesicles or the extract from one or more modified extracellular vesicles contain one or more cargo molecules in an amount that is greater or lesser than the amount of the one or more cargo molecules present inside or on the surface of an extracellular vesicle from the same cell or an extract of one or more extracellular vesicles from the same cell produced without electrical stimulation. In some cases, delivering the composition can be selected from intravenous injection and intranasal delivery.

In another aspect, a method of treating a brain disorder is provided, the method including administering to a subject having brain disorder a composition including one or more modified extracellular vesicles or an extract from one or more modified extracellular vesicles, wherein the modified extracellular vesicles are produced by electrical stimulation of a target cell, and wherein the one or more modified extracellular vesicles or the extract from one or more modified extracellular vesicles contain one or more cargo molecules in an amount that is greater or lesser than the amount of the one or more cargo molecules present inside or on the surface of an extracellular vesicle from the same cell or an extract of one or more extracellular vesicles from the same cell produced without electrical stimulation. In some cases, delivering the composition can be selected from intravenous injection and intranasal delivery. In some cases, the brain disorder can be selected from Parkinson's disease, essential tremor, dystonia, cognitive disorders, and epilepsy.

In another aspect, a method of stimulating electrically active cells is provided, the method including stimulating extracellular vesicle release by electrically silent cells. In some cases, the electrically active cells and the electrically silent cells can be situated adjacent one another. In some cases, the electrically active cells can be neurons. In some cases, the electrically silent cells can be glial cells. In some cases, the electrically silent cells can be astrocytes.

In another aspect, a method of stimulating the release of extracellular vesicles from electrically silent cells is provided, the method including biochemically or electrically stimulating activity of spatially adjacent electrically active cells. In some cases, the electrically active cells can be neurons. In some cases, the electrically silent cells can be glial cells. In some cases, the electrically silent cells can be astrocytes.

The methods and compositions described herein provide several advantages. First, modulation of EV production and cargo content by electrical stimulation of target cells provides methods for understanding and individualized treatment of disease processes, such as epilepsy. The methods described herein may provide insight into how external and endogenous electrical activity modulate EVs. The effect of external electric fields on EVs may represent a basic phenomenon that could be traced back to the very beginning of single-cell life-forms responding to external electric fields. The fundamental role, if any, of the brain's large-scale electrical activity as measured by electroencephalogram (EEG) has remained unclear. The electrical activity of the brain includes several frequency bands, including delta (1-4 Hz), theta (>4-8 Hz), alpha (>8-13 Hz), beta (>13-30 Hz), low gamma (>30-70 Hz), and high gamma (>70-150 Hz), and there is evidence that via ephaptic coupling the spike timing of individual neurons is modulated by local field potentials[72]. One of the most dramatic changes in EEG in mammalian brain is during the transition from wake and sleep where the EEG changes to higher amplitude low frequency activity. This dramatic change in the EEG could provide a behavioral state specific tuning of EV release and cargo. The methods described herein could provide tool for understanding brain activity and its biological effect.

Second, modulation of EV production and cargo content by electrical stimulation of target cells provides a reliable, large-scale production source for EVs for research and therapeutic purposes. The methods and compositions described herein can provide a powerful mechanism for modulating EV release and EV cargo that would serve various biological and pathological functions. For example, certain miRNAs can be specifically associated with extracellular vesicles produced by electrical stimulation, regardless of stimulation frequency, and/or certain miRNAs can be specifically associated with certain electrical stimulation parameters, such as certain frequencies. Thus, production of EVs can be tuned using electrical stimulation to produce EVs carrying various unique and/or desired sets of miRNAs.

Third, modulation of EV production and cargo content by electrical stimulation of target cells and compositions derived therefrom provides a clean, non-invasive, physical, therapeutic delivery vehicle and/or therapeutic production mechanism for therapeutic cargo molecules present in or on the surface of EVs. This can provide a new way to produce EVs carrying desired cargos by tuning ES parameters. EVs can act as therapeutic carriers due to their unique characteristics. Unlike other methods for creating EVs using chemical reagents, ES is a clean physical method with several adjustable parameters including oscillation frequency, field strength and waveform.

Fourth, modulation of EV production and cargo content by electrical stimulation of target cells and compositions derived therefrom provides an additional mechanism of action for tuning therapeutic ES used to treat several neurological disorders[45,73], such as epilepsy[27,39,74-75], sleep and memory dysfunction[36,76-77], brain tumors[78] and Parkinson's disease[79]. In ES therapy for particular neurological diseases, the effects often depend on stimulation frequency: for parkinsonian and idiopathic tremor, high stimulation frequencies (>90 Hz) improve motor symptoms, whereas lower frequencies (<50 Hz) are either ineffective or can exacerbate symptoms[54]. In contrast, low frequency (<3 Hz) stimulation safely and effectively reduces the seizures in epilepsy[7,39]. The underlying mechanism of frequency-dependent ES therapy is still largely unknown. Using EVs as biomarkers for ES therapy, stimulation parameters can be fine-tuned to achieve a better outcome.

Fifth, in some cases described herein, ES can be applied to reduce exosomal PD-L1 release, and thus provide a cancer treatment, including slowing tumor growth and improving efficacy for other treatments such as chemotherapy, radiotherapy and immune therapy. Such ES treatment can be invasive, such as electrodes in the organ (e.g. brain), on the organ (e.g. brain), in the organ blood vessels, or non-invasive and complementary to other treatments. ES treatments can be applied precisely to target a specific tumor or tumor region, thus minimizing side effects.

Sixth, modulation of EV production and cargo content by electrical stimulation of target cells and compositions derived therefrom can be usefully adapted to and optimized using modern computing technologies. The recent progress in the field of artificial intelligence can provide a systematic method for tuning the EVs for individual need in a large scale population.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

For the terms "for example" and "such as," and grammatical equivalences thereof, the phrase "and without limitation" is understood to follow unless explicitly stated otherwise. As used herein, the term "about" is meant to account for variations due to experimental error. As used herein, the singular forms "a," "an," and "the" are used interchangeably and include plural referents unless the context clearly dictates otherwise.

Also herein, the recitations of numerical ranges by endpoints include all numbers subsumed within that range (e.g., 1 to 5 includes 1, 1.5, 2, 2.75, 3, 3.80. 4, 5, etc.).

Other features and advantages of the invention will be apparent from the following detailed description and figures, and from the claims.

DETAILED DESCRIPTION

Figure 1A:
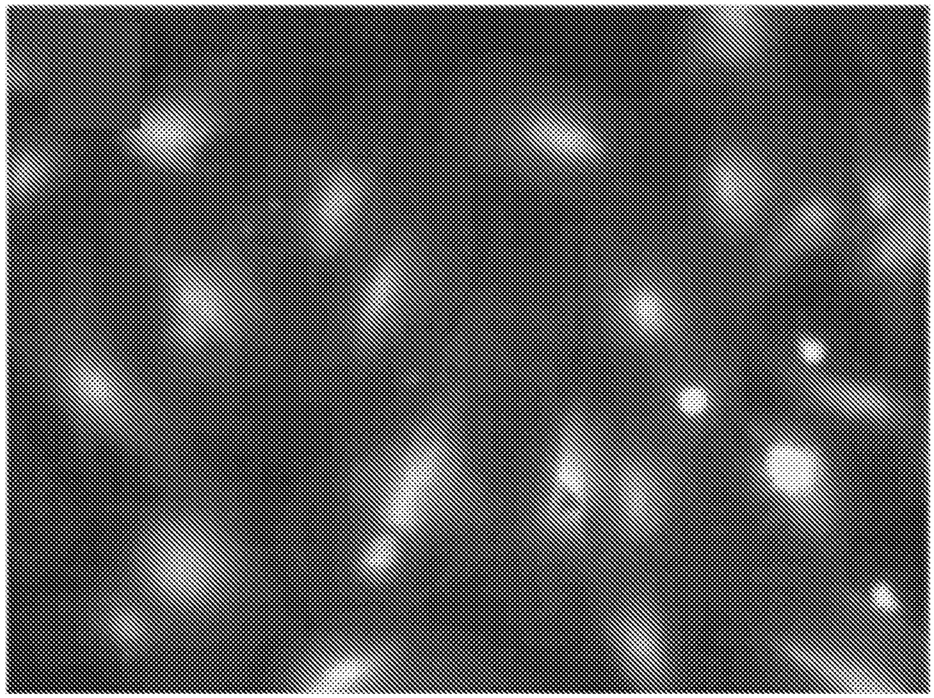
FIG. 1(A-F) is a sequence of images showing EVs released during 2 Hz electrical stimulation from primary mouse astrocytes loaded with Calcein dye at 0 seconds (A), 16 seconds (B), 20 seconds (C), 60 seconds (D), 72 seconds (E), and 120 seconds (F) as described in Example 1.
Figure 1B:
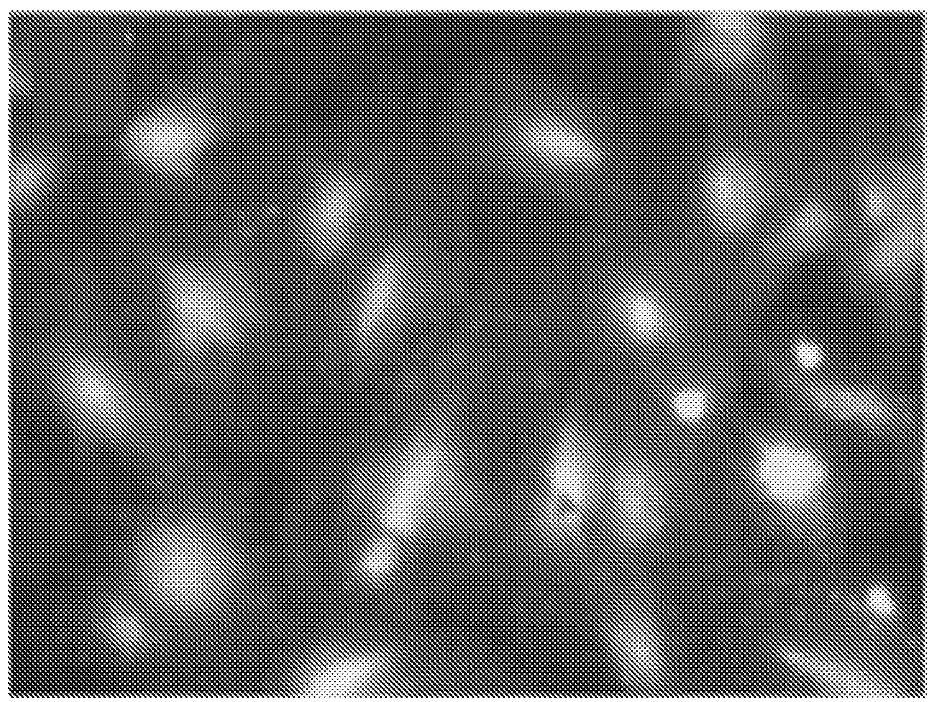
Figure 1C:
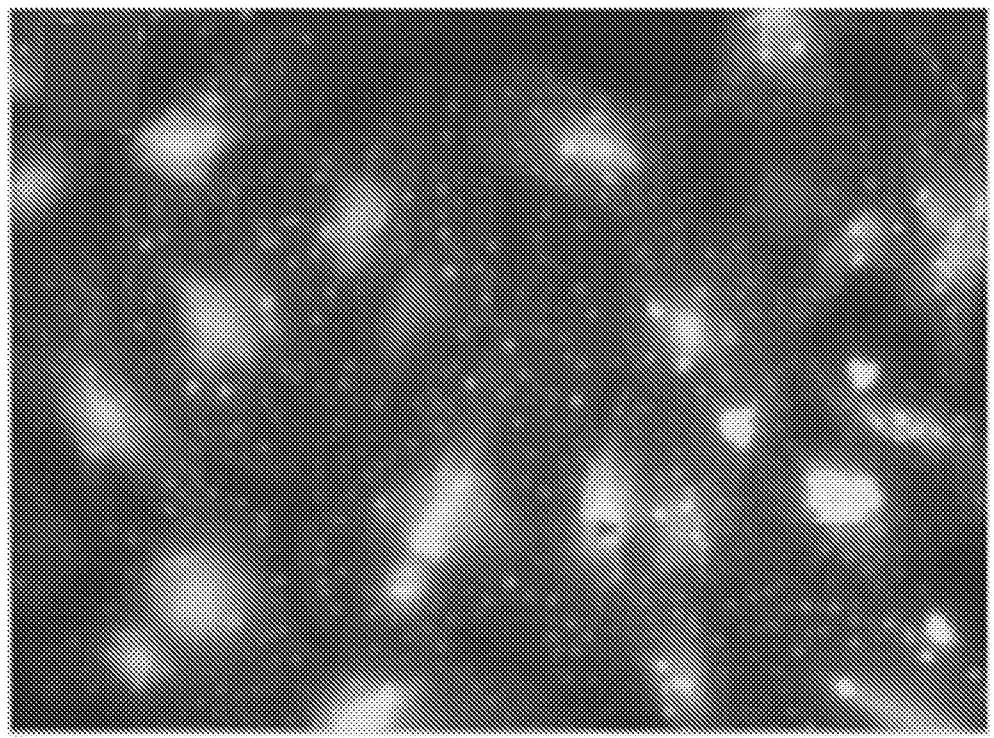
Figure 1D:
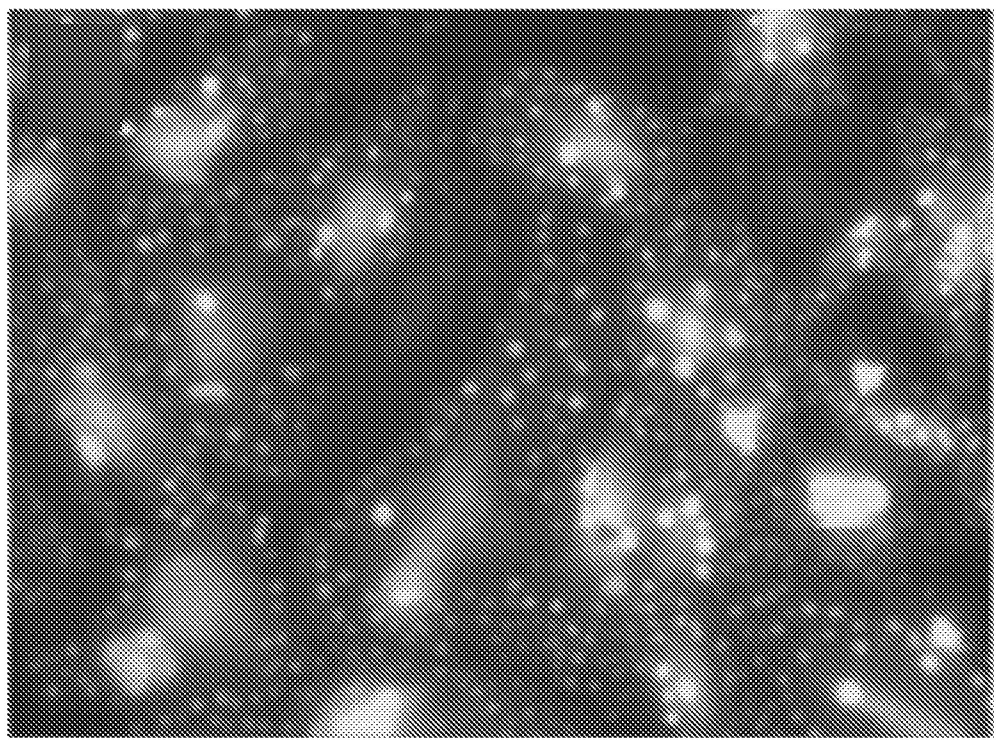
Figure 1E:
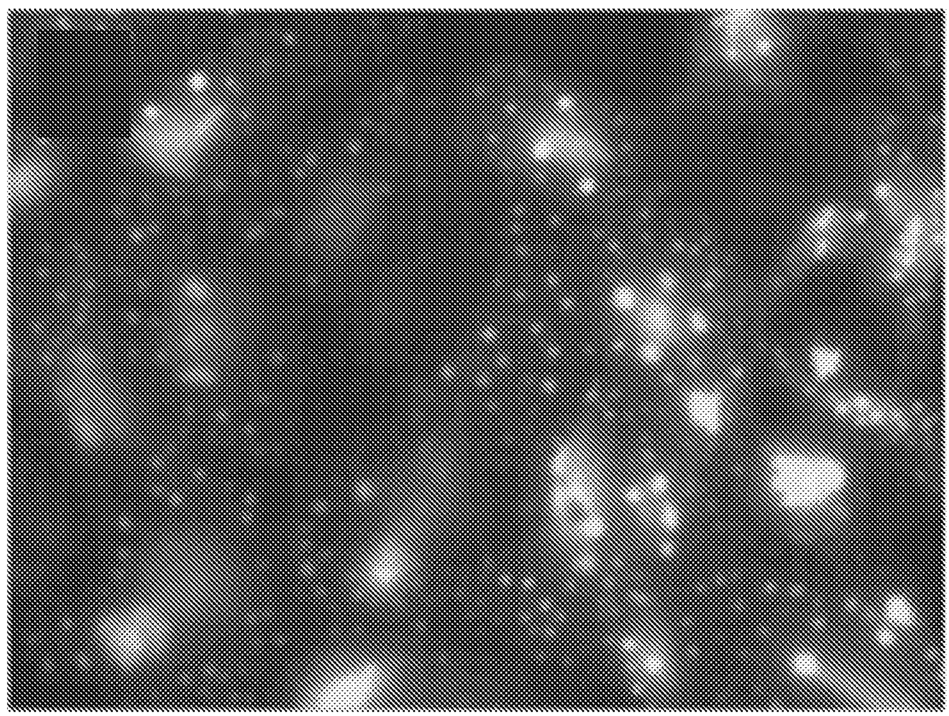
Figure 1F:
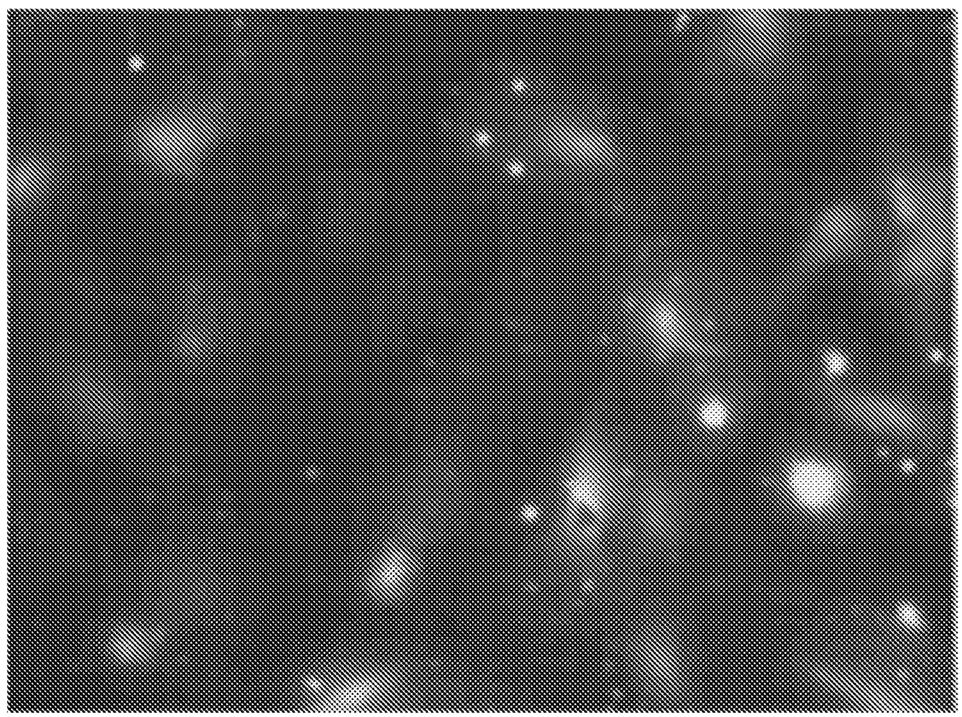

The present disclosure is directed to modulating the release and/or content of EVs from one or more cells using electrical stimulation.

The release of EVs and their production processes are tightly regulated, varying between physiological and pathologic conditions[85, 86]. External stimuli to cells can drastically change the EV-production rate and EV content or composition. However, stimulation through chemicals suffers from a lack of specificity and releases a heterogeneous population of vesicles[87, 88]. A clean and efficient method that regulates EV-production is needed. Provided herein are clean, physical methods for modulating EV production and cargo content by electrical stimulation of target cells and compositions derived therefrom. For example, in some cases of the methods described herein, ES can be used to selectively modulate EV release, and EV cargo content such as EV surface proteins and EV microRNA profiles. The concepts described herein may be applicable to any cell type.

In some cases, the methods and compositions described herein can be used for treating a disease (e.g., a cancer (e.g., glioblastoma, breast cancer, renal cancer, a solid cancer, a primary tumor, a metastatic tumor, a metastasis), a neurological disease (e.g., Parkinson's Disease, Huntington's Disease, Alzheimer's Disease, epilepsy), etc.). For example, in some cases, the methods described herein can be used to modulate EV release and/or EV cargo content to treat a disease. In some cases, the cancer can be, e.g., acute myeloid leukemia, bladder cancer, breast cancer, kidney cancer, melanoma, small cell lung cancer, non-small cell lung cancer, pancreatic cancer, or prostate cancer. In some cases, the methods described herein can be used to modulate release of EVs carrying PD-L1 and/or the content of PD-L1 in released EVs.

As used herein, "modulating" includes having an effect on an object, a process, or the like, such as a cell or its exosomes or ectosomes (microvesicles). Exemplary effects described by modulating include changing, such as increasing or decreasing, a characteristic such as size, or increasing or decreasing a parameter such as amount of, e.g., an object. For example, modulating the release of EVs from one or more cells can include causing EV release, and/or increasing or decreasing the number or size of exosomes or ectosomes derived from the one or more cells, and/or increasing or decreasing the speed of release of exosomes or ectosomes from the one or more cells. As another example, modulating the content of EVs can include increasing or decreasing the amount of one or more cargo molecules contained in an EV (exosome or ectosome), modifying a ratio of molecular contents of an EV, or causing one or more cargo molecules to be present or absent in an EV. The changed effect from modulating is observed with reference to EVs that may be produced from the same or similar cell under normal conditions. Normal conditions can include standard culturing conditions for a given in vitro cell, or wild type conditions for an in vivo cell. For example when causing an increase or decrease in the number of exosomes or ectosomes released from a cell under modified conditions, the increase or decrease is observed with respect to the difference between the EVs released by the same or similar cell under wild type, standard culture, or normal conditions as compared to the EVs released by the same or similar cell under modified conditions. In some instances the differences are observed over a specific time period, while in other instances the differences are cumulative.

As used herein, EV cargo includes molecules contained within the EVs or expressed on their surfaces, including, for example, miRNAs, DNA fragments, membrane proteins, cytokines, chemokines, mRNA, noncoding RNA, lipids, and other bioactive substances. In some cases, EV cargo includes PD-L1.

EVs and their cargo, including extracellular miRNAs, proteins, lipids, and mRNAs have potential as biomarkers of disease and as therapeutic molecules and delivery vehicles for specific cellular targets. EV bioactive cargo suggests both physiological and potentially pathological roles in viral infection, cancer spread, autoimmunity, epilepsy, and neurodegenerative diseases. EVs transfer their cargo (proteins, lipids and RNAs) in both a paracrine manner (to adjacent target cells) and an endocrine manner (to distant target cells)[3]. Besides their diagnostic properties, EVs also have emerged as vehicles for delivering therapeutics owing to their especially low toxicity compared with synthetic vesicles[21]. However knowledge of EV subtypes, their biogenesis, cargo molecules and mechanisms of shuttling is still incomplete.

The inventors have discovered surprisingly that electrical stimulation modulates the release and cargo content of EVs.

Currently, release of EVs is either spontaneous under normal cell culture conditions, or promoted by proinflammatory cytokines, like TNF-alpha[22]. Using biochemical agents has multiple pharmacological effects such as pharmacokinetics, interactions with other molecules, clearance rates and toxicity. On the other hand, electrical stimulation is a controllable, on-demand non-biochemical method.

The present disclosure provides, in some cases, methods of producing EVs from one or more target cells, including a single cell, populations of cells, intact organs or organ slice explant, by electrically stimulating the one or more target cells. In some cases, a method includes modulating the release and cargo content of extracellular vesicles from a target cell by electrically stimulating the target cell. In some cases, a method of increasing or decreasing the amount of one or more cargo molecules present in or on the surface of an extracellular vesicle of a target cell is provided, including electrically stimulating the target cell, wherein the amount of the one or more cargo molecules is increased or decreased as compared to the amount of the one or more cargo molecules present inside or on the surface of an extracellular vesicle of the same or same type of target cell produced without electrical stimulation.

Electrically stimulating the target cell can include applying an electrical field to the target cell with signal waveforms that are sinusoidal, square waves (charge balanced, i.e., Liley pulse), or complex waveforms, including white, pink, and other noise signals containing ranges of frequency. The defined waveforms, e.g. sinusoidal, can be applied at a frequency of from about 0.001 Hz to about 1000 Hz at from about 0.002 mV/mm to about 5 mV/mm for about 1 to about 5 minutes, from about 0.1 Hz to about 100 Hz at from about 1 mV/mm to about 5 mV/mm for about 1 to about 10 minutes, from about 10 Hz to about 30 Hz at from about 1 mV/mm to about 5 mV/mm for about 1 to about 5 minutes, from about 1 Hz to about 3 Hz at from about 1 mV/mm to about 5 mV/mm for about 1 to about 5 minutes, from about 190 Hz to about 210 Hz at from about 1 mV/mm to about 5 mV/mm for about 1 to about 5 minutes, from about 100 Hz to about 500 Hz at from about 0.1 mV/mm to about 5 mV/mm for about 1 to about 5 minutes, from about 1 Hz to about 500 Hz at from about 3 mV/mm to about 5 mV/mm for about 3 to about 5 minutes from about 1 Hz to about 3 Hz at from about 4 mV/mm to about 6 mV/mm for about 4 to about 6 minutes, from about 10 Hz to about 30 Hz at from about 4 mV/mm to about 6 mV/mm for about 4 to about 6 minutes, or from about 190 Hz to about 210 Hz at from about 4 mV/mm to about 6 mV/mm for about 4 to about 6 minutes. Some exemplary applications include, about 200 Hz at about 5 mV/mm for about 5 minutes, about 20 Hz at about 5 mV/mm for about 5 minutes, about 2 Hz at about 5 mV/mm for about 5 minutes, or 2 Hz at 5 mV/mm for 5 minutes. In some cases, the electric field is a uniform electric field. It has been discovered that the use of a uniform field is particularly useful for in vitro production of EVs from round cell culture dishes. In some cases, electrically stimulating the target cell includes applying patterned pulses, such as by varying the duration and number of pulses in a single train, varying the quiet period between two pulse trains, and the like.

In some cases, EV release can be affected by high-order oligomerization of membrane proteins[61]. In some cases, the electrical field can affect protein oligomerization and EV formation.

In some cases, the target cell can be a cultured cell. In some cases, the target cell can be an in vivo cell. In some cases, stimulating the target cell can include stimulating an organ or portion of an organ containing said target cell. Organs that may be stimulated include brain, heart, liver, lung, skeletal muscle, and other tissues. In some cases, stimulating the target cell can include stimulating an organ slice, such as a brain slice, in vitro.

In some cases, the target cell is an electrically silent cell. For example, the target cell can be a glial cell. In some cases, the target cell is an astrocyte.

In some cases, a method of producing extracellular vesicles derived from a target cell is provided, the method comprising obtaining the target cell; culturing the target cell; and electrically stimulating the target cell. The target cell can be obtained from intact tissue or progenitor cells differentiated in culture. In some cases, the target cell or cells can be obtained from nervous system tissues and can include neurons, astrocytes, or other glial cells. In some cases, the target cell or cells can be obtained from, e.g., cardiac myocytes or hepatic cells. Culturing the target cell can include culturing the target cell for a time period of from about 15 to 35 days, from about 20 to 30 days, or from about 21 days to about 28 days. The target cell can be washed prior to the step of electrically stimulating the cell to eliminate contaminant or EVs produced by the target cell without electrical stimulation. The method can further include collecting extracellular vesicles released after the step of electrically stimulating the target cell. In some cases, the target cell can be one or more astrocytes.

The present disclosure also includes methods of engineering EVs for therapeutic intervention. It has been discovered surprisingly that electrical stimulation parameters, including the frequency of electrical signal and pulse width and the electrical field strength, affect not only cellular vesiculation, but also the cargo content of EVs. EVs and their cargos are variable depending on the host cell's physiological (stress) and pathological processes (toxins and carcinogenesis). Without wishing to be bound by theory, it is believed that the physical stress of electrical stimulation modulates the release of EVs and influences their cargo content. Thus, the cargo content, such as the type and amount of one or more of the proteins, lipids, mRNAs, miRNAs, and non-coding RNAs can be adjusted by adjusting stimulation parameters for the cells.

In some cases, the miRNA content of an EV can be modulated by increasing or decreasing the amount of one or more miRNAs present in or on the surface of an EV released from a target cell by adjusting the electrical stimulation parameters. MicroRNAs (miRNAs) have therapeutic potential for regenerative medicine[1]. These small, non-coding RNAs direct post-transcriptional regulation of gene networks by targeting protein-coding mRNAs that are pivotal in the pathogenesis of neurological disorders such as epilepsy. For example, evidence for dysregulation of numerous specific miRNAs in epilepsy supports the hypothesis that miRNAs, as gene expression regulators, are pertinent to both the cause and treatment of epilepsy.

The major drawback of miRNAs as therapeutic agents is the lack of efficient vehicles for delivery to the target site or cell type[2]. The ideal delivery system would transfer the desired miRNA cargo to a specific tissue or organ in a local and sustained manner. Viral- and non-viral-based vectors both have safety issues including potential immunogenicity, insertional mutagenesis, toxicity and nonspecific uptake. EVs are released from all cell types into extracellular fluids and are capable of transferring their bioactive cargo (proteins, lipids and RNAs) in both a paracrine manner (to adjacent homotypic cells) and an endocrine manner (to distant target cells)[3]. The following four properties make EV-transferred miRNAs ideal regulators of cellular function: 1) remarkable stability; 2) low cytotoxicity; 3) permeation of the blood-brain barrier and 4) target cell selectivity.

In some cases, a method of increasing or decreasing the content of one or more miRNAs in extracellular vesicles released from a target cell is provided, the method including electrically stimulating the target cell, wherein the content of the one or more miRNAs is increased or decreased as compared to the amount of the one or more miRNAs present inside or on the surface of an extracellular vesicle of the same or same type of target cell produced without electrical stimulation. In some cases, increasing the content of one or more miRNAs in extracellular vesicles released to from a target cell includes producing EVs having miRNA that is not present inside or on the surface of an extracellular vesicle released by the same or same type of target cell without electrical stimulation.

In some cases, the one or more miRNAs are selected from an miRNA that is upregulated in one or more forms of epilepsy, such as miR-21, miR-146, miR-34a, miR-134, and miR-132, and combinations thereof[64]. In some cases, the one or more miRNAs are selected from miR-423-5p, miR-4700-5p, miR-181a-5p, miR-92b-3p, miR-99b-5p, miR-320b, miR-23b-3p, miR-125b-5p, miR-27b-3p, miR-21-5p, miR-184, miR-23a-3p, miR-203a-3p, miR-125a-3p, miR-22-3p, miR-320a-3p, miR-103a-3p, miR-10a-5p, miR-27a-3p, miR-7704, miR-107, miR-148a-3p, miR-25-3p, miR-let-7f-5p, miR-221-3p, miR-4492, miR-let-7i-5p, miR-let-7a-5p, miR-92a-3p, let-7c-5p, 125a-5p, 10b-5p, 151a-3p, 28-3p, 191-5p, miR-7977, miR-130a-3p, miR-143-3p, miR-26a-5p, miR-100-5p, miR-3168, miR-1469, miR-4680-3p, miR-4259, miR-205-5p, miR-3195, miR-let-7b-5p, miR-30a-5p, miR-30d-5p, miR-375-3p, miR-183-5p, miR-146b-5p, miR-378a-3p, miR-26b-5p, miR-9-5p, miR-222-3p, miR-423-3p, miR-744-5p, miR-99a-5p, miR-4775, miR-4324, miR-662, miR-4781-3p, miR-5100, miR-361-5p, miR-125b-1-3p, miR-30d-3p, miR-125b-2-3p, miR-193b-3p, miR-141-3p, miR-24-3p, miR-5047, miR-21-3p, miR-129-5p, miR-151a-5p, miR-30a-3p, miR-210-3p, miR-6728-5p, miR-204-5p, miR-30e-5p, miR-98-5p, miR-186-5p, miR-486-5p, miR-10395-3p, miR-431-5p, miR-148b-5p, miR-182-5p, miR-3661, miR-6068, and combinations thereof.

In some cases, a method of increasing or decreasing the content of one or more membrane proteins in extracellular vesicles released from a target cell is provided, the method including electrically stimulating the target cell, wherein the content of the one or more membrane proteins is increased or decreased as compared to the amount of the one or more membrane proteins present inside or on the surface of an extracellular vesicle of the same or same type of target cell produced without electrical stimulation.

In some cases, a method of increasing or decreasing the content of one or more mRNAs in extracellular vesicles released from a target cell is provided, the method including electrically stimulating the target cell, wherein the content of the one or more mRNAs is increased or decreased as compared to the amount of the one or more mRNAs present inside or on the surface of an extracellular vesicle of the same or same type of target cell produced without electrical stimulation.

In some cases, a method of increasing or decreasing the content of one or more cytokines or chemokines in extracellular vesicles released from a target cell is provided, the method including electrically stimulating the target cell, wherein the content of the one or more cytokines or chemokines is increased or decreased as compared to the amount of the one or more cytokines or chemokines present inside or on the surface of an extracellular vesicle of the same or same type of target cell produced without electrical stimulation.

In some cases, the target cell can be any cell type. In some cases, the target cell can be selected from the group consisting of a mammalian cell a protozoal cell, an algal cell, a plant cell, a fungal cell, an invertebrate cell, a fish cell, an amphibian cell, a reptile cell, or a bird cell. In some cases, the target cell can be a cancer cell. In some cases, the target cell can be a human cell. In some cases, the target cell can be a secretory epithelial cell, such as a salivary gland mucous cell, a salivary gland number 1 cell, a Von Ebner's gland cell, a mammary gland cell, a lacrimal gland cell, ceruminous gland cell, an eccrine sweat glandering dark cell, an eccrine sweat gland clear cell, an apocrine sweat gland cell, a gland of Moll cell, a sebaceous gland cell, a Bowman's gland cell, a Brunner's gland cell, a seminal vesicle cell, a prostate gland cell, a bulbourethral gland cell, a Bartholin's gland cell, a Gland of Littre cell, a uterus endometrium cell, an insolated goblet cell, a stomach lining mucous cell, a gastric gland zymogenic cell, a gastric gland oxyntic cell, a pancreatic acinar cell, a paneth cell, a type II pneumocyte, a club cell; a hormone-secreting cell, such as an anterior pituitary cell, a somatotrope, a lactotrope, a thyrotrope, a gonadotrope, a corticotrope, an intermediate pituitary cell, a magnocellular neurosecretory cell, a gut or respiratory tract cell, a thyroid gland cell, a thyroid epithelial cell, a parafollicular cell, a parathyroid gland cell, a parathyroid chief cell, an oxyphil cell, an adrenal gland cell, a chromaffin cell, a leydig cell, a theca interna cell, a corpus luteum cell, a granulosa lutein cell, a theca lutein cell, a juxtaglomerular cell, a macula densa cell, a peripolar cell, a mesangial cell, a pancreatic islet cell, an alpha cell, a beta cell, a delta cell, a PP cell (gamma cell), an epsilon cell; a keratinizing epithelial cells, such as an epidermal keratinocyte, an epidermal basal cell, a keratinocyte, a nail bed basal cell, a medullary hair shaft cell, a cortical hair shaft cell, a cuticular hair shaft cell, a cuticular hair root sheath cell, a hair root sheath cell of Huxley's layer, a hair root sheath cell of Henle's layer, an external hair root sheath cell, a hair matrix cell; a wet stratified barrier epithelial cell, such as a surface epithelial cell of stratified squamous epithelium, a basal cell of epithelia, a urinary epithelium cell; a sensory transducer cell, such as an auditory inner hair cell, an auditory outer hair cell, a basal cell of olfactory epithelium, a cold-sensitive primary sensory neuron, a heat-sensitive primary sensory neuron, a Merkel cell of epidermis, an olfactory receptor neuron, a pain-sensitive primary sensory neuron, a photoreceptor cell, a photoreceptor rod cell, a photoreceptor blue-sensitive cone cell, a photoreceptor green-sensitive cone cell, a photoreceptor red-sensitive cone cell, a proprioceptive primary sensory neuron, a touch-sensitive primary sensory neuron, a chemoreceptor glomus cell, an outer hair cell of vestibular system, an inner hair cell of vestibular system, a taste receptor cell; an autonomic neuron cell, such as a cholinergic neural cell, an adrenergic neural cell, a peptidergic neural cell; a sense organ or peripheral neuron supporting cell, such as an inner pillar cell of organ of *Corti*, an outer pillar cell of organ of *Corti*, an inner phalangeal cell of organ of *Corti*, an outer phalangeal cell of organ of *Corti*, a border cell of organ of *Corti*, a Hensen cell of organ of *Corti*, a vestibular apparatus supporting cell, a taste bud supporting cell, an olfactory epithelium supporting cell, a Schwann cell, a satellite glial cell, an enteric glial cell; a central nervous system neuron or glial cells, such as a neuron, an interneuron, a basket cell, a cartwheel cell, a stellate cell, a golgi cell, a granule cell, a Lugaro cell, a unipolar brush cell, a Martinotti cell, a chandelier cell, a Cajal-Retzius cell, a double-bouquet cell, a neurogliaform cell, a retina horizontal cell, an amacrine cell, a spinal interneuron, a Renshaw cell, a principal cell, a spindle neuron, a fork neuron, a pyramidal cell, a place cell, a grid cell, a Betz cell, a stellate cell, a bushy cell, a Purkinje cell, a medium spiny neuron, an astrocyte, an oligodendrocyte, an ependymal cell, a tanycyte; a lens cell, such as an anterior lens epithelial cell, a crystallin-containing lens fiber cell; an adipocyte; a lipocyte; a kidney or renal cell, such as a kidney parietal cell, a kidney glomerulus podocyte, a kidney proximal tubule brush border cell, a Loop of Henle thin segment cell, a kidney distal tubule cell, a kidney collecting duct cell; a Type I pneumocyte; a pancreatic duct cell; a nonstriated duct cell; a duct cell; an intestinal brush border cell; an exocrine gland striated duct cell; a gall bladder epithelial cell; a ductulus efferens nonciliated cell; an epididymal principal cell; an epididymal basal cell; an endothelial cell; an extracellular matrix cell, such as a planum semilunatum epithelial cell, an organ of *Corti* interdental epithelial cell, a fibroblast, an epithelial fibroblast, a nonepithelial fibroblast, a loose connective tissue fibroblasts, a corneal fibroblasts, a pericyte, a chondrocyte, an osteocyte, a hyalocyte, a hepatic stellate cell, a pancreatic stelle cell; a skeletal muscle cell, such as a red skeletal muscle cell, a white skeletal muscle cell, an intermediate skeletal muscle cell, a satellite cell; a heart muscle cell; smooth muscle cell; a myoepithelial cell of iris; a myoepithelial cell of exocrine glands; a blood or immune system cell, such as an erythrocyte; a megakaryocyte, a monocyte, a macrophage, a Langerhans cell, an osteoclast, a dendritic cell, a microglial cell, a neutrophil, an eosinophil, a basophil, a hybridoma cell, a mast cell, a T cell, a B cell, a natural killer cell, a reticulocyte, a hematopoietic stem cell or progenitor cell; an ovarian follicle cell; a sertoli cell; a thymus epithelial cell; an interstitial kidney cell. In some cases, the target cell can be selected from the group consisting of a hematopoietic cell, a mammary cell, an intestinal cell, a mesenchymal cell, an endothelial cell, a neural cell, an olfactory cell, a neural crest cell, a skin cell, a testicular cell, a fibroblast. In some cases, the target cell can be selected from an astrocyte, a neuron, a microglia, an oligodendrocyte precursor, an ependymocyte, a cerebral endothelial cell, a renal cell, a cancer cell, or combinations thereof.

In some cases, factors such as age, sex, body mass index and medication may influence cellular vesiculation. Therefore, in some cases, adjustments can be made to the electrical stimulation of the cells based on the presence of one or more of these factors in the organism from which the cells are derived. In some cases, such as in large scale production of EVs for therapeutic purposes, steps can be taken to minimize variables and optimize reproducibility among produced EVs by standardizing these or other factors. For example, in some cases, the period of primary cell culture before EV preparation can be standardized. In some cases, the cell culture period can range from about 7 days to about 35 days, from about 10 days to about 30 days, from about 7 days to about 14 days, from about 25 days to about 35 days, or from about 20 to 30 days at sub-confluent density. In some cases, the cell line can be an astrocytic cell line and the period of primary cell culture can range from about 7 to about 28 days, about 7 to 14 days, or about 21 to 28 days at sub-confluent density.

Another method for optimizing reproducibility can include eliminating EVs from the culture medium and any supplementary serum or other additives by washing the cells prior to electrical stimulation. Washing the cells prior to electrical stimulation can also remove any EVs released spontaneously from the growing cells. Another method for optimizing reproducibility can include matching source species groups according to age, sex and weight.

In some aspects, EVs can be engineered to include, exclude, or modify EV surface proteins, or the amount of EV surface proteins, that influence mobility and target cell recognition. For example, in the case of astrocyte derived EVs, aquaporin-4 (AQP4) water channel is implicated in homomeric oligomerization[60], glial/glioblastoma motility16 and astrocytic adhesion properties[17]. Such surface proteins can be used for in vivo targeting by EVs.

In some cases, methods are provided for treating a disease (e.g., a cancer (e.g., glioblastoma, breast cancer, renal cancer, a solid cancer, a primary tumor, a metastatic tumor, a metastasis), a neurological disease (e.g., Parkinson's Disease, Huntington's Disease, Alzheimer's Disease, epilepsy), etc.) in a subject. In some cases, the subject is in need of, or has been determined to be in need of, such treatment. In some cases, ES can be used to modulate EV release and/or EV cargo content to treat a disease. In some cases, ES can be used to modulate EV release from cancer cells and/or EV cargo content in EVs released from cancer cells to treat cancer, or to suppress or limit the spread of cancer, such as the spread of tumor cells. In some cases, a method is provided for treating cancer in a subject having a tumor, comprising electrically stimulating at least a portion of the tumor or a portion of the subject containing the tumor. In some cases, a method is provided for reducing spread of a tumor in a subject having the tumor, comprising electrically stimulating at least a portion of the tumor or a portion of the subject containing the tumor. In some cases, the cancer can be, e.g., breast cancer, kidney cancer, or glioblastoma.

As used herein, the term "subject" refers to any mammal. In some cases, the subject may be a rodent (e.g., a mouse, a rat, a hamster, a guinea pig), a canine (e.g., a dog), a feline (e.g., a cat), an equine (e.g., a horse), an ovine, a bovine, a porcine, a primate, e.g., a simian (e.g., a monkey), an ape (e.g., a gorilla, a chimpanzee, an orangutan, a gibbon), or a human. In some cases of any of the methods described herein, the subject is between 1 minute and 120 years old. In some cases of any of the methods described herein, the subject is a fetus or mammal undergoing gestation. Any of the methods described herein can be used to treat a subject, e.g., a diseased subject (i.e., a subject with a disease, e.g., who has been diagnosed with a disease), or an asymptomatic subject (i.e., a subject who clinically presents as healthy, or who has not been diagnosed with a disease). As used herein, treating includes "prophylactic treatment" which means reducing the incidence of or preventing (or reducing risk of) a sign or symptom of a disease in a subject at risk for the disease, and "therapeutic treatment", which means reducing signs or symptoms of a disease, reducing progression of a disease, reducing severity of a disease, re-occurrence in a subject diagnosed with the disease. As used herein, the term "treat" means to ameliorate at least one clinical parameter of the disease (e.g., reduce tumor size, prevent or reduce tumor spread, reduce a symptom, etc.).

In some cases of any of the methods provided herein, the ES is administered at least once (e.g., 2, 3, 4, 5, 6, 7, 8, 9, 10, 11, 12, 13, 14, 15, 16, 17, 18, 19, 20, 30, 40, 50, 60, 70 80, 90, 100 times) during a period of time (e.g., every day, every 2 days, twice a week, once a week, every week, three times per month, two times per month, one time per month, every 2 months, every 3 months, every 4 months, every 5 months, every 6 months, every 7 months, every 8 months, every 9 months, every 10 months, every 11 months, once a year). Also contemplated are monthly treatments, e.g., administering at least once per month for at least 1 month (e.g., at least two, at least three, at least four, at least five, at least six or more months, e.g., 12 or more months), and yearly treatments (e.g., administration once a year for one or more years).

The frequency and duration of ES, frequency of administration of ES, and timing of administration required to effectively treat a subject may be influenced by the age of the subject, the general health of the subject, the severity of the disease, previous treatments, and the presence of comorbidities. In some cases, ES treatment can be invasive, such as through electrodes in the organ (e.g. brain), on the organ (e.g. brain), or in the organ blood vessels. In some cases, ES treatment can be non-invasive. In some cases, the ES fields and currents can be created non-invasively using transcranial magnetic field stimulation (TMS). In some cases, ES treatment can be complementary to or additional to other treatments. In some cases, the ES can be generated using single or multitude arrays of electrodes to deliver currents.

The methods described herein can be used in cancer treatments. The term "cancer" refers to cells having the capacity for autonomous growth. Examples of such cells includes cells having an abnormal state or condition characterized by rapidly proliferating cell growth. The term is meant to include cancerous growths, e.g., tumors, oncogenic processes, metastatic tissues, malignantly transformed cells.

A metastatic tumor can arise from a multitude of primary tumor types, including but not limited to those of brain, prostate, colon, lung, breast, bone and liver origin. Metastases develop, e.g., when tumor cells shed, detach or migrate from a primary tumor, enter the vascular system, penetrate into surrounding tissues, and grow to form tumors at distinct anatomical sites, e.g., sites separate from a primary tumor.

Individuals considered at risk for developing cancer may benefit from the present disclosure, e.g., because prophylactic treatment can begin before there is any evidence and/or diagnosis of the disorder. Individuals "at risk" include, e.g., individuals exposed to carcinogens, e.g., by consumption (e.g., by inhalation and/or ingestion), at levels that have been shown statistically to promote cancer in susceptible individuals. Also included are individuals at risk due to exposure to ultraviolet radiation, or their environment, occupation, and/or heredity, as well as those who show signs of a precancerous condition such as polyps. Similarly, individuals in very early stages of cancer or development of metastases (i.e., only one or a few aberrant cells are present in the individual's body or at a particular site in an individual's tissue) may benefit from such prophylactic treatment.

Skilled practitioners will appreciate that a patient can be diagnosed, e.g., by a medical professional, e.g., a physician or nurse (or veterinarian, as appropriate for the patient being diagnosed), as suffering from or at risk for a condition described herein, e.g., cancer, using any method known in the art, e.g., by assessing a patient's medical history, performing diagnostic tests, and/or by employing imaging techniques.

Skilled practitioners will also appreciate that treatment need not be administered to a patient by the same individual who diagnosed the patient (or the same individual who prescribed the treatment for the patient). Treatment can be administered (and/or administration can be supervised), e.g., by the diagnosing and/or prescribing individual, and/or any other individual, including the patient her/himself (e.g., where the patient is capable of self-administration).

Non-limiting examples of cancer include: acute lymphoblastic leukemia (ALL), acute myeloid leukemia (AML), adrenocortical carcinoma, anal cancer, appendix cancer, astrocytoma, basal cell carcinoma, brain tumor, glioblastoma, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and para-nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms' tumor.

For example, any of the methods described herein can be used to treat a cancer selected from the group consisting of: glioblastoma, squamous cell carcinoma, breast cancer, colon cancer, hepatocellular cancer, melanoma, neuroblastoma, renal cancer, pancreatic cancer, and prostate cancer. Treatment of multiple cancer types at the same time is contemplated by and within the present disclosure.

In some instances, the subject having the cancer may have previously received another cancer treatment and/or may be concomitantly receiving another cancer treatment (e.g., any of the cancer treatments described herein).

In some cases of any of the methods provided herein, the ES is administered with one or more additional therapies (e.g., chemotherapy (e.g., a chemotherapeutic agent (e.g., doxorubicin, paclitaxel, cyclophosphamide), cell-based therapy, radiation therapy, immunotherapy, a small molecule, an inhibitory nucleic acid (e.g., antisense RNA, antisense DNA, miRNA, siRNA, lncRNA), another exosome-based therapy, gene therapy or surgery).

In some cases, the methods described herein can be used to modulate release of EVs carrying PD-L1 from cancer cells and/or the content of PD-L1 in EVs released from cancer cells. EVs carrying PD-L1 are possible mediators of spreading cancer; ES modulation of EV content may provide a generic mechanism of suppressing PD-L1 in EVs and/or PD-L1 carrying EVs, and may be useful as a therapeutic targeting cancer spread.

A recent principle for cancer therapy is to stimulate the inherent ability of our immune system to attack tumor cells. One area of progress that has shown promise in therapeutic advancement for human cancers, including solid tumors, is anti-PD therapy, targeting the programmed death-1/programmed death ligand-1 (PD-1/PD-L1) pathway (referred to as the PD pathway) with monoclonal antibodies used for blocking the PD pathway[92].

PD-L1 is expressed on a variety of cell types. The PD-1/PD-L1 regulatory mechanism was designed to protect normal mucosa from autoimmune attack; unregulated PD-L1 on cells binds PD-1 on T cells, contributing to the development of T-cell exhaustion[93]. Tumor cells have co-opted this PD-1/PD-L1 regulatory mechanism, and instead overexpress PD-L1 to avoid immunologic surveillance to facilitate cancer growth[94]. Cancer cells release ample extracellular vesicles (EVs), mostly in the form of exosomes, which carry PD-L1 on their surfaces. Exosomal PD-L1 can suppress the function of CD8 T cells and facilitate tumor growth[95]. The increased level of circulating exosomal PD-L1 likely causes cancer spread and reduces efficacy of treatment by neutralizing antibodies designed to block PD-pathway.

Instead of increasing the amount of applied antibody which inherently generates negative impact of toxicity, the methods described herein using ES can reduce the release of tumor-derived exosomal PD-L1. The release of EVs and their cargo content is specifically related to a physiological condition of the host cell. ES employs the body's natural biological response, and can have different effects on cells in a normal or in a disease condition. Focal ES can, in some cases, be applied precisely to target a tumor or tumor region, thus minimizing side effects encountered with systemic treatment.

In some cases, application of ES can reduce exosomal PD-L1 derived from cancer tissue using electrical stimulation in order to improve efficacy of cancer treatment, such as immune therapy using antibodies targeting at PD pathway. The ES can be delivered non-invasively or invasively. In some cases, a method is provided for reducing exosomal PD-L1 derived from one or more target cells, or present in a target tissue or an extracellular milieu surrounding one or more target cells, comprising electrically stimulating the one or more target cells, at least a portion of the target tissue or target tissue region containing at least a portion of the target cells or target tissue.

For example, in some cases, when EVs are quantified in a sample (e.g., target cells, target tissue, blood sample, extracellular milieu sample) after application of ES at about 2 Hz at about 5 mV/mm for about 5 minutes, the amount of EVs carrying PD-L1 is lower than the amount of EVs carrying PD-L1 in a similar sample without electrical stimulation (e.g., a sample taken from a tissue, a tissue portion, one or more cells, extracellular milieu, petri dish, blood sample, or urine sample not subjected to external electrical stimulation). In some cases, when EVs are quantified in a sample after application of ES at about 20 Hz at about 5 mV/mm for about 5 minutes, the amount of EVs carrying PD-L1 is lower than the amount of EVs carrying PD-L1 in a similar sample without electrical stimulation. In some cases, when EVs are quantified in a sample after application of ES at about 200 Hz at about 5 mV/mm for about 5 minutes, the amount of EVs carrying PD-L1 is lower than the amount of EVs carrying PD-L1 in a similar sample without electrical stimulation. In some cases, when EVs are quantified in a sample after application of ES at about 2 KHz at about 5 mV/mm for about 5 minutes, the amount of EVs carrying PD-L1 is lower than the amount of EVs carrying PD-L1 in a similar sample without electrical stimulation. In some cases, when EVs are quantified in a sample after application of ES at about 8 KHz at about 5 mV/mm for about 5 minutes, the amount of EVs carrying PD-L1 is lower than the amount of EVs carrying PD-L1 in a similar sample without electrical stimulation.

As another example, in some cases, when exosomal PD-L1 is quantified in a sample (e.g., target cells, target tissue, blood sample, extracellular milieu sample) after application of ES at about 2 Hz at about 5 mV/mm for about 5 minutes, the amount of exosomal PD-L1 is lower than the amount of exosomal PD-L1 in a similar sample without electrical stimulation (e.g., a sample taken from a tissue, a tissue portion, one or more cells, extracellular milieu, petri dish, blood sample, or urine sample not subjected to external electrical stimulation). In some cases, when EVs are quantified in a sample after application of ES at about 20 Hz at about 5 mV/mm for about 5 minutes, the amount of exosomal PD-L1 is lower than the amount exosomal PD-L1 in a similar sample without electrical stimulation. In some cases, when EVs are quantified in a sample after application of ES at about 200 Hz at about 5 mV/mm for about 5 minutes, the amount of exosomal PD-L1 is lower than the amount of exosomal PD-L1 in a similar sample without electrical stimulation. In some cases, when EVs are quantified in a sample after application of ES at about 2 KHz at about 5 mV/mm for about 5 minutes, the amount of exosomal PD-L1 is lower than the amount of exosomal PD-L1 in a similar sample without electrical stimulation. In some cases, when EVs are quantified in a sample after application of ES at about 8 KHz at about 5 mV/mm for about 5 minutes, the amount of exosomal PD-L1 is lower than the amount of exosomal PD-L1 in a similar sample without electrical stimulation.

In some cases, a target cell is a cell that produces EVs. In some cases, the target cell produces EVs carrying (e.g., inside or on the surface of the EVs) PD-L1. In some cases, a target tissue is a tissue or tissue portion containing one or more target cells. In some cases, a target tissue region can include a region of tissue containing at least a portion of the target tissue and/or target cells, as well as tissue or cells that are not target tissues or target cells. In some cases, a target tissue region is a portion of a subject, such as a portion of the body of a subject (e.g., a leg, an abdomen or portion of an abdomen, a breast, an organ (e.g., brain, kidney), etc.). In some cases, extracellular milieu In some cases, ES can be applied to reduce exosomal PD-L1 release, and thus slow tumor growth and improve efficacy for other treatments, such as chemotherapy, radiotherapy and immune therapy. Induced modulation of extracellular vesicles can be achieved under various (invasive or non-invasive) stimulations, including (but not limited to) electrical, magnetic or ultrasonic stimulations.

Different cancer cells and cell types may have different responses to ES (e.g., suppression of PD-L1 EVs and/or PD-L1 content of EVs may occur at different applied field frequencies in for different cells). It will be appreciated that one skilled in the art can determine the appropriate applied field frequencies and duration for a particular cancer, cell, or cell type. In the methods described herein, ES parameters (e.g., frequency, current amplitude, pulse width, wave-form morphology) can be adjusted and tuned by one skilled in the art to minimize the release of exosomal PD-L1, and thus optimize the cancer therapy and individualize the therapy for each patient and tumor type.

Glioblastoma (GBM) is a grade IV malignant brain tumor. GBM cells reproduce rapidly and easily grow into normal brain tissue. Median survival for patients is approximately 11-15 months. In some cases, ES can be applied to a subject to treat GBM and/or to suppress the spread of GBM cells. The methods described herein for reducing PD-L1 EVs or PD-L1 content in EVs differs from other ES therapy for GBM[96], which relies on the principle of arresting cell proliferation[97].

The methods described herein can also be useful in treating other cancers. In some cases, ES can be applied to a subject to treat renal cancer and/or to suppress the spread of cancerous renal cells. In some cases, the renal cancer is a renal adenocarcinoma. In some cases, ES can be applied to a subject to treat breast cancer and/or to suppress the spread of breast cancer cells. In some cases, the breast cancer is a breast adenocarcinoma.

In certain instances, a course of treatment and/or the severity of the disease being treated can be monitored. In some cases, PD-L1 can be used as a biomarker to detect early stage cancer, track tumor development, and/or track effectiveness of a cancer treatment. Tumor-associated PD-L1 (B7-H1) promotes T-cell apoptosis and regulates cellular and humoral immune responses through the PD-1 receptor on activated T and B cells. The expression of PD-L1 is rather minimal in normal human tissues but abundant in human carcinomas (e.g., carcinomas of the lung, ovary, colon, and in glioblastomas and melanomas). These tumor cells release extracellular vesicles (mostly in the form of exosomes) that carry PD-L1 on their surface. Therefore, increased circulating exosomal PD-L1 can be a useful biomarker for indicating early stage cancer, and can be detected through liquid biopsy. Furthermore, the magnitude of exosomal PD-L1 changes during treatment can indicate the adaptive response of the tumor cells to T cell reinvigoration, and can be used to stratify clinical responders from non-responders. In some cases, anti-PD-L1 antibodies, such as monoclonal anti-PD-L1 antibodies, can be used for exosomal PD-L1 detection.

An anti-PD-L1 antibody can be an antibody that binds to a PD-L1 protein (also known as CD274). For example, an anti-PD-L1 antibody can bind to a human PD-L1 protein. A human PD-L1 protein be any isoform of the human PD-L1 protein, including any of the sequences known by UniParc reference numbers: UPI000003816A, UPI00001BD8B1, UPI00003E5A06. UniParc reference number UPI000003816A is generally considered to be the canonical human PD-L1 sequence. In some cases, an anti-PD-L1 antibody can bind to the PD-L1 sequence known by UniParc reference number UPI000003816A.

An anti-PD-L1 antibody can be any appropriate anti-PD-L1 antibody. Non-limiting examples of anti-PD-L1 antibodies include atezolizumab (Tecentriq®), avelumab (Bavencio®), durvalumab (Imfinzi®), BMS-936559, CK-301, MPDL3280A, MEDI4736, and MSB0010718C. Additional non-limiting examples of anti-PD-L1 antibodies include Abcam product numbers ab205921, ab228415, ab209889, ab213524, ab228462, ab80276, ab226766, ab238697, ab210931, ab228463, ab213480, ab221612, ab233482, ab237726, ab209960, ab236238, ab243877, ab209959, ab224027, or ab223141. Additional non-limiting examples of anti-PD-L1 antibodies include Cell Signaling Technologiyes product numbers 13684, 15165, 86744, 29122, or 64988. Additional non-limiting examples of anti-PD-L1 antibodies include Millipore Sigma product numbers SAB2500216, ABF133, MABC991, MABC980, MABC1131, MABF404, SAB4301882, SAB5600121, or AB3500123. Additional non-limiting examples of anti-PD-L1 antibodies include BD Biosciences catalog numbers 558065, 558017, 563742, 563738, 564554, 565188, 563741, 563739, 741423, 746346, 561787, or 557924. Additional non-limiting examples of anti-PD-L1 antibodies include Thermo Fisher Scientific catalog numbers 14-5982-82, 12-5983-42, 46-5983-42, 46-5982-82, 17-5983-42, 16-5983-82, 14-9971-82, PAS-18337, PAS-20343, PAS-28115, 14-5983-82, 13-9971-81, 13-5983-82, 62-5982-80, or 48-5983-42. Additional non-limiting examples of anti-PD-L1 antibodies include New England Biolabs item numbers 136845, 151655, or 25048S. Additional non-limiting examples of anti-PD-L1 antibodies can be found in Chen, et al.[95], for example, clone 5H1-A3, clone MIH1 (BD Biosciences), clone E1L3N (Cell Signaling Technology), clone SH1, clone D8T4X (Cell Signaling Technology), and clone 29E.2A3 (BioLegend). Additional non-limiting examples of anti-PD-L1 antibodies can found in articles with the following PubMed IDs (PMIDs): 29336307, 21355078, 14530338, 11224527, and 27824138.

In some cases, an anti-PD-L1 antibody can be detectable in any appropriate application, for example, flow cytometry, immunocytochemistry, immunofluorescence, immunohistochemistry (e.g., immunohistochemistry paraffin, immunohistochemistry frozen), Western blotting, immunoprecipitation, ELISA. In some cases, an anti-PD-L1 antibody can be commercially available in a form that is detectable in an appropriate application. In some cases, an anti-PD-L1 antibody can be prepared to be detectable in an appropriate application, using any appropriate method. In some cases, an anti-PD-L1 antibody can be conjugated to a dye. A dye-conjugated anti-PD-L1 antibody can be a commercially available dye-conjugated anti-PD-L1 antibody, or dye-conjugated anti-PD-L1 antibody can be prepared using any appropriate method. In some cases, an anti-PD-L1 antibody can be selected based on the detection method.

Additional non-limiting examples of anti-PD-L1 antibodies can be found elsewhere, for example, in the product catalogs of Abcam, Cell Signaling Technology, Sigma Aldrich (Millipore Sigma), EMD Millipore (Millipore Sigma), BD Biosciences, Thermo Fisher Scientific, New England Biolabs, or any other antibody vendor.

In some cases, a method is provided for determining the effectiveness of a cancer treatment in a subject, comprising quantifying an amount of exosomal PD-L1 in a sample from the subject. In some cases, quantifying can include quantifying the amount of exosomal PD-L1 in a sample from the subject at two or more time points before, during, or after the treatment. In some cases, the method can comprise quantifying, at a first time point a first amount of exosomal PD-L1 in a sample from the subject; quantifying, at a second time point a second amount of exosomal PD-L1 in a sample from the subject; and determining the effectiveness of the treatment based on a difference between the first amount and second amount of exosomal PD-L1. In some cases, the method can comprise quantifying the amount of exosomal PD-L1 in a sample from the subject at 3 or more time points, 4 or more time points, 5 or more time points, 10 or more time points, 15 or more time points, or 20 or more time points. In some cases, the first time point can be prior to a treatment, or upon commencement of a treatment. In some cases, the first time point can be after treatment. In some cases, the second and later time point can be after treatment, such as 1 hour, 2 hours, 3 hours, 4 hours, 6 hours, 8 hours, 10 hours, 12 hours, 20 hours, 1 day, 2 days, 4 days, 6 days, 1 week, 2 weeks, 3 weeks, 1 month, 2 months, 3 months, 6 months, 9 months, 12 months, or more after treatment. In some cases, samples can be taken from a subject and exosomal PD-L1 in the sample can be quantified at time points long after treatment has stopped, for example, to monitor the status of the subject and/or the cancer.

In some cases, a method is provided for detecting cancer in a subject, comprising quantifying the amount of exosomal PD-L1 in a sample from the subject. In some cases, the amount of exosomal PD-L1 in the sample can be compared against a threshold value indicative of a type of cancer or a stage of cancer. It will be appreciated that the threshold value will be dependent upon the type of cancer and the type of sample taken. In some cases, the sample is a tissue sample. In some cases, the sample is a blood sample. In some cases, the sample is a urine sample.

In one embodiment, a system for in vitro electrical stimulation of one or more target cells is provided. The electrical stimulation system can be a bench top device (that uses electrical stimulation to optimally tune EV cargo for therapeutic applications.

Figure 3:
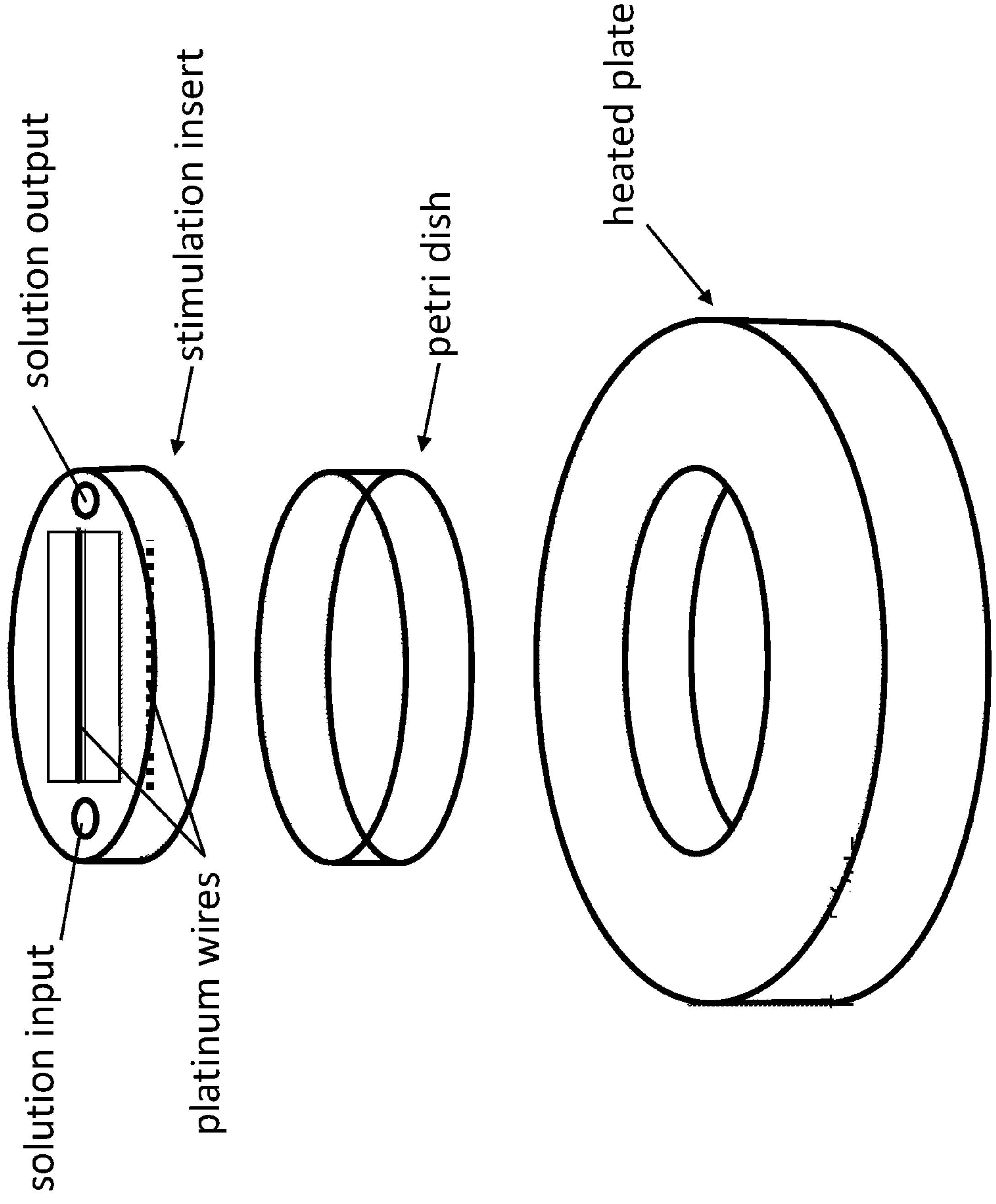
FIG. 3 is perspective view of an exemplary system that can be used in performing some of the methods described herein.

In one embodiment, the electrical stimulation system includes an insert for a petri dish. The insert has an opening with two connections for solution exchanges, one as input for preheated medium solutions and the other one is an output to a medium collector. Two platinum wires are embedded on opposite sides of the opening and provide a uniform electric field when it is connected to an electrical signal generator. In addition, a heated plate surrounds the petri dish to keep cell culture at a desired temperature. A series of patterned electrical pulses are then applied to the wires while extracellular vesicles are collected. Various exemplary cases of the invention are shown in FIG. 3. A series of patterned electrical pulses can be applied to the wires while extracellular vesicles are collected.

The device and system for in vitro electrical stimulation is suitable for large-scale production of EVs enriched with specific miRNAs, which will have both therapeutic and economic benefits to the field of regenerative medicine[10].

In another aspect, a composition is provided comprising one or more modified extracellular vesicles or an extract from one or more modified extracellular vesicles, wherein the modified extracellular vesicles are produced by electrical stimulation of a target cell, and wherein the one or more modified extracellular vesicles or the extract from one or more modified extracellular vesicles contain one or more cargo molecules in an amount that is greater or lesser than the amount of the one or more cargo molecules present inside or on the surface of an extracellular vesicle from the same cell or an extract of one or more extracellular vesicles from the same cell produced without electrical stimulation.

In some cases, the one or more cargo molecules are selected from a protein, a lipids, an mRNA, a noncoding RNA, and an miRNA.

In some cases, miRNAs contained in extracellular vesicles derived from astroglial cells can be used for therapeutic benefit to the central nervous system.

It has been discovered surprisingly that miRNA profiles of astrocyte-derived EVs and other cellular EVs can be altered by electrical stimulation. EVs derived from artificial electrical stimulation of astrocytes are hereinafter referred to as "Ase-EVs." In one embodiment, Ase-EVs are produced by low-frequency electrical stimulation (2 Hz, 5 mV/mm for 5 mins) containing elevated levels of at least two miRNAs, miR-21 and miR-146. Both of these miRNAs have been reported elevated in brain tissue of children with mesial temporal lobe epilepsy[13] and in regional brain homogenates of rats subjected to tetanic stimulation-induced seizures[14]. miR-21 is documented as a strong anti-apoptotic factor4 and miR-146 is a critical factor in immune responses, regulating the inflammatory response[5]. They target different members of the tumor necrosis factor (TNF-α) family, and are consistently up-regulated in several neurological disorders, including epilepsy[6].

Electrical brain stimulation (EBS) is an emerging therapy for several neurologic disorders. Although epilepsy, parkinsonian and essential tremor are FDA-approved indications for focal EBS, using implanted electrodes, the molecular basis of its efficacy remains unclear, and seizure-free outcomes are rare. EVs released from astrocytes under electrical stimulation can be an important component of EBS' therapeutic effect, and the efficacy might be improved by individualizing stimulation to "tune" EV cargo. All cell types release into extracellular fluids EVs that transfer bioactive cargo (proteins, lipids and RNAs) in both paracrine and endocrine manner. The inventors' discovery that miRNA profiles of astrocyte-derived EVs can be altered by electrical stimulation has several clinical implications.

Firstly, it provides a plausible explanation for the empirically-observed therapeutic benefit of deep-brain stimulation for epilepsy[7] and several other neurological disorders[8]. Secondly, it suggests the use of Ase-EVs as a potential non-invasive therapeutic approach for multiple neurological disorders[9].

In addition to the proven benefit of EBS therapy for epilepsy, parkinsonian and essential tremor[33], preliminary studies show improvement from EBS targeting cortical and deep brain structures for cognition[36,42,43], depression[45,46], and post-traumatic stress disorder[41]. However, epilepsy patients are rarely rendered seizure-free by deep brain stimulation (DBS) targeting the thalamus[38] or by responsive stimulation (RNS) targeting the hippocampus and cortex[27]. Improvements in EBS therapy are needed.

Epilepsy affects 65 million individuals worldwide, and antiepileptic drugs fail to control seizures in 30% of patients. Recent advances in neuroimaging, neural autoantibody detection and brain stimulation devices have improved the management of drug-resistant epilepsy by reducing seizure severity and frequency. Well-designed trials have led to FDA approval of EBS[27,38], but improved efficacy is needed. The inventors have recently demonstrated that continuous subthreshold stimulation significantly improves efficacy[7,44], but the lack of mechanistic understanding of EBS therapy slows progress. Data from experimental epilepsy models and analysis of resected human brain tissues suggest an important role for innate immune system activation and inflammation in epilepsy. As the most abundant cells in the central nervous system (CNS), astrocytes have critical homeostatic functions. Their proposed role in CNS disorders is reinforced by recognition that: 1) the astrocytic syncytium is the afferent lymphatic gateway[58] leading from brain parenchyma to cervical lymph nodes via meningeal lymphatic vessels[25]; 2) autoimmune astrocytopathies illustrate the outcomes of acquired disruption of astrocyte functions (mediated, for example, by aquaporin-4-specific IgG[59] or by cytotoxic T cells specific for glial fibrillary acidic protein-derived peptides[37]; 3) pro-inflammatory cytokines influence astrocytes to activate CNS-infiltrating antigen-specific helper and cytotoxic T cells by processing locally released antigens and presenting them via MHC class 2 molecules, and 4) stress conditions signal astro-neuronal progenitor cells to proliferate, differentiate and repair. Fundamental to these processes are the mechanisms by which astrocytes communicate with each other, with other CNS cells and with other systems and organs.

Recent studies have reported that astrocyte-derived EVs ("As-EVs") regulate the peripheral leukocyte response to inflammatory brain lesions[34], and that the miRNA profiles of EVs are altered in plasma of patients with mesial temporal lobe epilepsy and hippocampal sclerosis[57], a very common type of focal epilepsy. As-EV miRNAs are suggested mediators of neuronal plasticity[40].

Without wishing to be bound by theory, it is proposed that altered properties of Ase-EVs produced under the influence of electrical stimulation have therapeutic effects applicable to antiepileptic treatment. The negative effects of a seizure are well-recognized. Counterintuitively, this hypothesis predicts that the large-scale electric signal generated by a seizure's synchronous neuronal activity might promote the release of EVs containing anti-inflammatory miRNAs, thus limiting inflammatory damage to the affected brain region[47]. Although resembling seizure activity, the beneficial effect of controlled focal electrical treatment can be delivered on a much smaller scale. This hypothesis plausibly explains why therapeutic electrical stimulation reduces the generation of large-scale clinical seizures and suppresses seizure spread.

In some cases a method of stimulating the brain of a subject is provided including delivering to the subject a composition including one or more modified extracellular vesicles or an extract from one or more modified extracellular vesicles, wherein the modified extracellular vesicles are produced by electrical stimulation of a target cell, and wherein the one or more modified extracellular vesicles or the extract from one or more modified extracellular vesicles contain one or more cargo molecules in an amount that is greater or lesser than the amount of the one or more cargo molecules present inside or on the surface of an extracellular vesicle from the same cell or an extract of one or more extracellular vesicles from the same cell produced without electrical stimulation. The one or more cargo molecules can be selected from a protein, a lipids, an mRNAs, a noncoding RNA, and an miRNA.

Depending on the target of the therapeutic, the composition can be delivered by intravenous injection, intramuscular injection, subcutaneous injection, intraperitoneal injection, intraocular delivery, or intranasal delivery.

In some cases, a method of treating a brain disorder is provided including administering to a subject having brain disorder a composition including one or more modified extracellular vesicles or an extract from one or more modified extracellular vesicles, wherein the modified extracellular vesicles are produced by electrical stimulation of a target cell, and wherein the one or more modified extracellular vesicles or the extract from one or more modified extracellular vesicles contain one or more cargo molecules in an amount that is greater or lesser than the amount of the one or more cargo molecules present inside or on the surface of an extracellular vesicle from the same cell or an extract of one or more extracellular vesicles from the same cell produced without electrical stimulation.

To cross the blood-brain barrier, the composition can be delivered by intravenous injection or intranasal delivery. The brain disorder can be selected from Parkinson's disease, essential tremor, dystonia, cognitive disorders, and epilepsy. In one embodiment, the brain disorder is a focal epilepsy. In one embodiment, the brain disorder is a refractory epilepsy.

In another embodiment, a method of stimulating electrically active cells is provided including stimulating extracellular vesicle release by electrically silent cells. It has been surprisingly discovered that the release of EVs from electrically silent cells such as astroglial cells can result in stimulation of electrically active cells such as neurons. In some cases, the electrically active cells and electrically silent cells are spatially adjacent such that the EVs transfer their cargo in a paracrine manner to the electrically active cells. Similarly, in another embodiment, a method of stimulating the release of extracellular vesicles from electrically silent cells is provided including stimulating activity of adjacent electrically active cells. The electrically active cells can be stimulated by artificial biochemical stimulation or by artificial electrical stimulation.

In some cases, the electrically active cells are neurons. In some cases, the electrically silent cells are glial cells. In some cases, the electrically silent cells are astrocytes.

In some cases, compositions containing EVs enriched in either or both miR-21 and miR-146, or extracts of EVs enriched in either or both miR-21 and miR-146 can be administered to a subject having epilepsy.

In some cases, administration of such compositions to a subject having epilepsy affects or modulates seizure activity. Types of epilepsy that can be modulated using one or more compositions containing EVs enriched in one or more components such as proteins, miRNAs (e.g., miR-21 and/or miR-146), or mRNAs, or extracts of EVs enriched one or more components include absence seizures (including typical and atypical absences), atonic seizures, catamenial seizures (menstrual-related), cluster seizures, episodic disorders, Dravet syndrome (severe myoclonic epilepsy in infancy or SMEI), focal (partial) seizures, focal (partial) seizures with secondary generalization, focal seizures with secondary generalised tonic clonic seizures, infantile spasms, Juvenile Myoclonic Epilepsy, Lennox-Gastaut syndrome, myoclonic seizures, myoclonic seizures in Juvenile Myoclonic Epilepsy, tonic seizures, tonic clonic seizures, tonic clonic seizures in severe myoclonic epilepsy in infancy (SMEI or Dravet syndrome), and West Syndrome with Tuberous Sclerosis.

Because epilepsy is driven by multiple cellular pathways that act in concert, the inhibition of a single target may have limited efficacy, or be deleterious. For example, overexpression of miR-21 can lead to suppression of several key tumor suppressor genes. Therefore, effective epilepsy treatment can, in some cases, include targeting multiple pathways simultaneously, either with one or more compositions containing EVs enriched in one or more components such as proteins, miRNAs (e.g., miR-21 and/or miR-146), or mRNAs, or extracts of EVs enriched one or more components. In some cases, the one or more compositions containing EVs enriched in one or more components or extracts of EVs enriched in one or more components can be administered in combination with one or more other anti-epileptic therapies. Anti-epileptic therapies that may be administered in combination with one or more compositions containing enriched EVs or extracts of enriched EVs include Acetazolamide, Carbamazepine, Clobazam, Clonazepam, Eslicarbazepine acetate, Ethosuximide, Gabapentin, Lacosamide, Lamotrigine, Levetiracetam, Nitrazepam, Oxcarbazepine, Perampanel, Piracetam, Phenobarbital, Phenytoin, Pregabalin, Primidone, Rufinamide, Sodium valproate, Stiripentol, Tiagabine, Topiramate, Vigabatrin, and Zonisamide.

In some cases of any of the compositions provided herein, the composition further includes one or more additional therapies (e.g., chemotherapy (e.g., a chemotherapeutic agent (e.g., doxorubicin, paclitaxel, cyclophosphamide), cell-based therapy, radiation therapy, immunotherapy, a small molecule, an inhibitory nucleic acid (e.g., antisense RNA, antisense DNA, miRNA, siRNA, lncRNA) or surgery).

EMBODIMENTS

Embodiment 1

A method of increasing or decreasing the amount of one or more cargo molecules present in or on the surface of an extracellular vesicle derived from a target cell, comprising:

electrically stimulating the target cell, wherein the amount of the one or more cargo molecules is increased or decreased as compared to the amount of the one or more cargo molecules present inside or on the surface of an extracellular vesicle of the same or same type of target cell produced without electrical stimulation.

Embodiment 2

The method of embodiment 1, wherein electrically stimulating the target cell comprises applying an electrical field to the target cell at a frequency of between about 0.001 Hz to about 1000 Hz at about 0.002 mV/mm to about 5 mV/mm for about 1 to about 5 minutes.

Embodiment 3

The method of embodiment 1, wherein electrically stimulating the target cell comprises applying an electrical field to the target cell at a frequency of about 200 Hz at about 5 mV/mm for about 5 minutes.

Embodiment 4

The method of embodiment 1, wherein electrically stimulating the target cell comprises applying an electrical field to the target cell at a frequency of about 20 Hz at about 5 mV/mm for about 5 minutes.

Embodiment 5

The method of embodiment 1, wherein electrically stimulating the target cell comprises applying an electrical field to the target cell at a frequency of 2 Hz at 5 mV/mm for 5 minutes.

Embodiment 6

The method of any one of embodiments 1-5 wherein the electric field is a uniform electric potential field.

Embodiment 7

The method of any one of embodiments 1-5, wherein electrically stimulating the target cell comprises applying patterned pulses.

Embodiment 8

The method of any one of embodiments 1-7, wherein stimulating the target cell comprises stimulating an organ or portion of an organ containing said target cell.

Embodiment 9

The method of any one of embodiments 1-8, wherein stimulating the target cell comprises stimulating a brain slice in vitro.

Embodiment 10

The method of any one of embodiments 1-9, wherein the target cell is a cultured cell.

Embodiment 11

The method of any one of embodiments 1-10, wherein the target cell is an electrically silent cell.

Embodiment 12

The method of any one of embodiments 1-10, wherein the target cell is a glial cell.

Embodiment 13

The method of any one of embodiments 1-10, wherein the target cell is an astrocyte.

Embodiment 14

A method for modulating the release and cargo content of extracellular vesicles from a target cell, comprising: electrically stimulating the target cell.

Embodiment 15

The method of embodiment 14, wherein electrically stimulating the target cell comprises applying an electrical field to the target cell at a frequency of between about 0.001 Hz to about 1000 Hz at about 0.002 mV/mm to about 5 mV/mm for about 1 to about 5 minutes.

Embodiment 16

The method of embodiment 14, wherein electrically stimulating the target cell comprises applying an electrical field to the target cell at a frequency of about 200 Hz at about 5 mV/mm for about 5 minutes.

Embodiment 17

The method of embodiment 14, wherein electrically stimulating the target cell comprises applying an electrical field to the target cell at a frequency of about 20 Hz at about 5 mV/mm for about 5 minutes.

Embodiment 18

The method of embodiment 14, wherein electrically stimulating the target cell comprises applying an electrical field to the target cell at a frequency of 2 Hz at 5 mV/mm for 5 minutes.

Embodiment 19

The method of any one of embodiments 14-18, wherein the electric field is a uniform electric potential field.

Embodiment 20

The method of any one of embodiments 14-18, wherein electrically stimulating the target cell comprises applying patterned pulses.

Embodiment 21

A method of generating extracellular vesicles from one or more electrically silent cells comprising electrically stimulating the cell.

Embodiment 22

The method of embodiment 21, wherein the electrically silent cell is a glial cell.

Embodiment 23

The method of embodiment 21, wherein the electrically silent cell is an astrocyte.

Embodiment 24

The method of any one of embodiments 21-23, wherein electrically stimulating the target cell comprises applying an electrical field to the target cell at a frequency of between about 0.001 Hz to about 1000 Hz at about 0.002 mV/mm to about 5 mV/mm for about 1 to about 5 minutes.

Embodiment 25

The method of any one of embodiments 21-23, wherein electrically stimulating the target cell comprises applying an electrical field to the target cell at a frequency of about 200 Hz at about 5 mV/mm for about 5 minutes.

Embodiment 26

The method of any one of embodiments 21-23, wherein electrically stimulating the target cell comprises applying an electrical field to the target cell at a frequency of about 20 Hz at about 5 mV/mm for about 5 minutes.

Embodiment 27

The method of any one of embodiments 21-23, wherein electrically stimulating the target cell comprises applying an electrical field to the target cell at a frequency of 2 Hz at 5 mV/mm for 5 minutes.

Embodiment 28

The method of any one of embodiments 21-27, wherein the electric field is a uniform electric potential field.

Embodiment 29

The method of any one of embodiments 21-27, wherein electrically stimulating the target cell comprises applying patterned pulses.

Embodiment 30

A method of increasing or decreasing content of one or more miRNAs in or on the surface of extracellular vesicles released from a target cell, comprising:

electrically stimulating the target cell, wherein the content of the one or more miRNAs is increased or decreased as compared to the amount of the one or more miRNAs present inside or on the surface of an extracellular vesicle of the same or same type of target cell produced without electrical stimulation.

Embodiment 31

The method of embodiment 30, wherein the one or more miRNAs are selected from miR-21, miR-146, miR-423-5p, miR-4700-5p, miR-181a-5p, miR-92b-3p, miR-99b-5p, miR-320b, miR-23b-3p, miR-125b-5p, miR-27b-3p, miR-21-5p, miR-184, miR-23a-3p, miR-203a-3p, miR-125a-3p, miR-22-3p, miR-320a-3p, miR-103a-3p, miR-10a-5p, miR-27a-3p, miR-7704, miR-107, miR-148a-3p, miR-25-3p, miR-let-7f-5p, miR-221-3p, miR-4492, miR-let-7i-5p, miR-let-7a-5p, miR-92a-3p, let-7c-5p, 125a-5p, 10b-5p, 151a-3p, 28-3p, 191-5p, miR-7977, miR-130a-3p, miR-143-3p, miR-26a-5p, miR-100-5p, miR-3168, miR-1469, miR-4680-3p, miR-4259, miR-205-5p, miR-3195, miR-let-7b-5p, miR-30a-5p, miR-30d-5p, miR-375-3p, miR-183-5p, miR-146b-5p, miR-378a-3p, miR-26b-5p, miR-9-5p, miR-222-3p, miR-423-3p, miR-744-5p, miR-99a-5p, miR-4775, miR-4324, miR-662, miR-4781-3p, miR-5100, miR-361-5p, miR-125b-1-3p, miR-30d-3p, miR-125b-2-3p, miR-193b-3p, miR-141-3p, miR-24-3p, miR-5047, miR-21-3p, miR- 129-5p, miR-151a-5p, miR-30a-3p, miR-210-3p, miR-6728-5p, miR-204-5p, miR-30e-5p, miR-98-5p, miR-186-5p, miR-486-5p, miR-10395-3p, miR-431-5p, miR-148b-5p, miR-182-5p, miR-3661, miR-6068, and combinations thereof.

Embodiment 32

The method of any one of embodiments 30-31, wherein the target cell is an astrocyte.

Embodiment 33

The method of any one of embodiments 30-32, wherein electrically stimulating the target cell comprises applying an electrical field to the target cell at a frequency of between about 0.001 Hz to about 1000 Hz at about 0.002 mV/mm to about 5 mV/mm for about 1 to about 5 minutes.

Embodiment 34

The method of any one of embodiments 30-32, wherein electrically stimulating the target cell comprises applying an electrical field to the target cell at a frequency of about 200 Hz at about 5 mV/mm for about 5 minutes.

Embodiment 35

The method of any one of embodiments 30-32, wherein electrically stimulating the target cell comprises applying an electrical field to the target cell at a frequency of about 20 Hz at about 5 mV/mm for about 5 minutes.

Embodiment 36

The method of any one of embodiments 30-32, wherein electrically stimulating the target cell comprises applying an electrical field to the target cell at a frequency of 2 Hz at 5 mV/mm for 5 minutes.

Embodiment 37

The method of any one of embodiments 30-36, wherein the electric field is a uniform electric potential field.

Embodiment 38

The method of any one of embodiments 30-36, wherein electrically stimulating the target cell comprises applying patterned pulses.

Embodiment 39

A method of producing extracellular vesicles derived from astrocytes, comprising:

obtaining the astrocytes;

culturing the astrocytes;

electrically stimulating the astrocytes.

Embodiment 40

The method of embodiment 39, wherein obtaining the astrocytes comprises harvesting the astocytes from brain tissue or from patient-derived Induced Pluripotent Stem Cells (iPSC).

Embodiment 41

The method of any one of embodiments 39-40, wherein culturing the astrocytes comprises culturing the astrocytes for a time period of from about 21 days to about 28 days.

Embodiment 42

The method of any one of embodiments 39-41, further comprising washing the astrocytes prior to the step of electrically stimulating the astrocytes.

Embodiment 43

The method of any one of embodiments 39-42, further comprising collecting extracellular vesicles released after the step of electrically stimulating the astrocytes.

Embodiment 44

The method of any one of embodiments 39-43, wherein electrically stimulating the astrocytes comprises applying an electrical field to the target cell at a frequency of between about 0.001 Hz to about 1000 Hz at about 0.002 mV/mm to about 5 mV/mm for about 1 to about 5 minutes.

Embodiment 45

The method of any one of embodiments 39-43, wherein electrically stimulating the astrocytes comprises applying an electrical field to the target cell at a frequency of about 200 Hz at about 5 mV/mm for about 5 minutes.

Embodiment 46

The method of any one of embodiments 39-43, wherein electrically stimulating the astrocytes comprises applying an electrical field to the target cell at a frequency of about 20 Hz at about 5 mV/mm for about 5 minutes.

Embodiment 47

The method of any one of embodiments 39-43, wherein electrically stimulating the astrocytes comprises applying an electrical field to the target cell at a frequency of 2 Hz at 5 mV/mm for 5 minutes.

Embodiment 48

The method of any one of embodiments 39-47, wherein the electric field is a uniform electric potential field.

Embodiment 49

The method of any one of embodiments 39-47, wherein electrically stimulating the astrocytes comprises applying patterned pulses.

Embodiment 50

A composition comprising one or more modified extracellular vesicles or an extract from one or more modified extracellular vesicles, wherein the modified extracellular vesicles are produced by electrical stimulation of a target cell, and wherein the one or more modified extracellular vesicles or the extract from one or more modified extracellular vesicles contain one or more cargo molecules in an amount that is greater or lesser than the amount of the one or more cargo molecules present inside an extracellular vesicle from the same cell or an extract of one or more extracellular vesicles from the same cell produced without electrical stimulation.

Embodiment 51

The composition of embodiment 50, wherein the one or more cargo molecules is selected from a protein, a lipids, an mRNAs, and an miRNA.

Embodiment 52

The composition of embodiment 50, wherein the one or more cargo molecules is an miRNA.

Embodiment 53

A method of stimulating the brain of a subject comprising delivering to the subject the composition of any one of embodiments 50-52.

Embodiment 54

The method of embodiment 53, wherein delivering the composition is selected from intravenous injection and intranasal delivery.

Embodiment 55

A method of treating a brain disorder comprising administering to a subject having brain disorder the composition of any one of embodiments 50-52.

Embodiment 56

The method of embodiment 55, wherein delivering the composition is selected from intravenous injection and intranasal delivery.

Embodiment 57

The method of any one of embodiments 55-56, wherein the brain disorder is selected from Parkinson's disease, essential tremor, dystonia, cognitive disorders, and epilepsy.

Embodiment 58

The method of any one of embodiments 55-56, wherein the brain disorder is epilepsy.

Embodiment 59

A method of stimulating electrically active cells comprising stimulating extracellular vesicle release by electrically silent cells.

Embodiment 60

The method of embodiment 59, wherein the electrically active cells and the electrically silent cells are situated adjacent one another.

Embodiment 61

The method of any one of embodiments 59-60, wherein the electrically active cells are neurons.

Embodiment 62

The method of any one of embodiments 59-60, wherein the electrically silent cells are glial cells.

Embodiment 63

The method of any one of embodiments 59-60, wherein the electrically silent cells are astrocytes.

Embodiment 64

A method of stimulating the release of extracellular vesicles from electrically silent cells comprising biochemically or electrically stimulating activity of spatially adjacent electrically active cells.

Embodiment 65

The method of embodiment 64, wherein the electrically active cells are neurons.

Embodiment 66

The method of embodiment 64, wherein the electrically silent cells are glial cells.

Embodiment 67

The method of embodiment 64, wherein the electrically silent cells are astrocytes.

Embodiment 68

The method of any one of embodiments 1-13, wherein the cargo molecule is PD-L1.

Embodiment 69

The method of embodiment 68, wherein an amount of PD-L1 is decreased as compared to an amount of PD-L1 present inside or on the surface of an extracellular vesicle of the same or same type of target cell produced without electrical stimulation.

Embodiment 70

The method of any one of embodiments 14-20, wherein extracellular vesicles are extracellular vesicles carrying PD-L1.

Embodiment 71

The method of any one of embodiments 14-20, wherein modulating the release of extracellular vesicles comprises decreasing the amount of extracellular vesicles carrying PD-L1 released from the target cell as compared to an amount of extracellular vesicles carrying PD-L1 released from the same target cell or target cell type without electrical stimulation.

Embodiment 72

The method of any one of embodiments 14-20, wherein modulating the cargo content of extracellular vesicles comprises decreasing the amount of PD-L1 inside or on the surface of extracellular vesicles released from the target cell an as compared to an amount of PD-L1 inside or on the surface of extracellular vesicles released from the target cell or target cell type without electrical stimulation.

Embodiment 73

The method of any one of embodiments 1-38 and 64-72, wherein the target cell is selected from the group consisting of a renal cell, a breast cell, and a glial cell.

Embodiment 74

The method of any one of embodiments 1-38 and 64-73, wherein the target cell is a cancer cell.

Embodiment 75

A method of reducing exosomal PD-L1 derived from one or more target cells, or present in a target tissue or an extracellular milieu surrounding one or more target cells, comprising electrically stimulating the one or more target cells, at least a portion of the target tissue or target tissue region containing at least a portion of the target cells or target tissue.

Embodiment 76

The method of embodiment 75, wherein electrically stimulating the one or more target cells, at least a portion of the target tissue or target tissue region containing at least a portion of the target cells or target tissue comprises applying an electrical field to the target cell at a frequency of between about 0.001 Hz to about 1000 Hz at about 0.002 mV/mm to about 5 mV/mm for about 1 to about 5 minutes.

Embodiment 77

The method of embodiment 75, wherein electrically stimulating the one or more target cells, at least a portion of the target tissue or target tissue region containing at least a portion of the target cells or target tissue comprises applying an electrical field to the target cell at a frequency of about 200 Hz at about 5 mV/mm for about 5 minutes.

Embodiment 78

The method of embodiment 75, wherein electrically stimulating the one or more target cells, at least a portion of the target tissue or target tissue region containing at least a portion of the target cells or target tissue comprises applying an electrical field to the target cell at a frequency of about 20 Hz at about 5 mV/mm for about 5 minutes.

Embodiment 79

The method of any one of embodiments 75-78, wherein the electric field is a uniform electric potential field.

Embodiment 80

The method of any one of embodiments 75-78, wherein electrically stimulating the one or more target cells, at least a portion of the target tissue or target tissue region containing at least a portion of the target cells or target tissue comprises applying patterned pulses.

Embodiment 81

A method of treating cancer in a subject having a tumor, comprising electrically stimulating at least a portion of the tumor or a portion of the subject containing the tumor.

Embodiment 82

A method of reducing spread of a tumor in a subject having the tumor, comprising electrically stimulating at least a portion of the tumor or a portion of the subject containing the tumor.

Embodiment 83

The method of any one of embodiments 81-82, wherein electrically stimulating at least a portion of the tumor or a portion of the subject containing the tumor comprises applying an electrical field to the target cell at a frequency of between about 0.001 Hz to about 1000 Hz at about 0.002 mV/mm to about 5 mV/mm for about 1 to about 5 minutes.

Embodiment 84

The method of any one of embodiments 81-82, wherein electrically stimulating at least a portion of the tumor or a portion of the subject containing the tumor comprises applying an electrical field to the target cell at a frequency of about 200 Hz at about 5 mV/mm for about 5 minutes.

Embodiment 85

The method of any one of embodiments 81-82, wherein electrically stimulating at least a portion of the tumor or a portion of the subject containing the tumor comprises applying an electrical field to the target cell at a frequency of about 20 Hz at about 5 mV/mm for about 5 minutes.

Embodiment 86

The method of any one of embodiments 81-85, wherein the electric field is a uniform electric potential field.

Embodiment 87

The method of any one of embodiments 81-85, wherein electrically stimulating at least a portion of the tumor or a portion of the subject containing the tumor comprises applying patterned pulses.

Embodiment 88

The method of any one of embodiments 81-87, wherein the tumor is a solid tumor.

Embodiment 89

The method of any one of embodiments 81-88, wherein the tumor is a breast adenocarcinoma, a renal adenocarcinoma, or a glioblastoma Embodiment 90

The method of any one of embodiments 81-89, wherein wherein an amount of PD-L1 present inside or on the surface of an extracellular vesicle produced by one or more cells of the tumor is decreased as compared to the amount of PD-L1 present inside or on the surface of an extracellular vesicle of the same or same type of cell produced without electrical stimulation.

Embodiment 91

The method of any one of embodiments 81-90, wherein an amount of exosomal PD-L1 present in or around the tumor is decreased as compared to the amount of PD-L1 present in or around the same or same type of tumor without electrical stimulation Embodiment 92

The method of any one of embodiments 81-91, further comprising administering to the subject one or more additional therapies before, during, or after the electrical stimulation.

Embodiment 93

The method of embodiment 92, wherein the one or more additional therapies are selected from the group consisting of chemotherapy, radiation therapy, and immunotherapy.

Embodiment 94

The method of embodiment 93, wherein the chemotherapy comprises administering a chemotherapeutic agent selected from the group consisting of doxorubicin, paclitaxel, cyclophosphamide, and combinations thereof.

Embodiment 95

A method of determining the effectiveness of a cancer treatment in a subject, comprising quantifying an amount of exosomal PD-L1 in a sample from the subject.

Embodiment 96

The method of embodiment 95, wherein quantifying comprises quantifying the amount of exosomal PD-L1 in a sample from the subject at two or more time points before, during, or after the treatment.

Embodiment 97

The method of embodiment 95, comprising:

quantifying, at a first time point a first amount of exosomal PD-L1 in a sample from the subject;

quantifying, at a second time point a second amount of exosomal PD-L1 in a sample from the subject; and determining the effectiveness of the treatment based on a difference between the first amount and second amount of exosomal PD-L1.

Embodiment 98

A method of detecting cancer in a subject, comprising quantifying the amount of exosomal PD-L1 in a sample from the subject.

EXAMPLES

Example 1: Release of EVs with Electrical Stimulation

The effect of ES on release of EVs was evaluated in astrocytes, the most heterogeneous type of homeostatic glia in the central nervous system (CNS). Most brain activities involve interaction between astrocytes and neurons, including physical interaction of astrocytes with synapses as well as blood vessels[66, 67] Astroglial functions[68] include regulation of synaptic connectivity, integration and synchronization of neuronal networks and the maintenance of the blood-brain barrier integrity. Instead of being electrically silent, astrocytes respond to low levels of electrical stimulation (ES) with elevation of their intracellular calcium concentration[69, 70] Primary mouse (brain tissue of pups, approximately 1 to 4 days old, from house breed wild type 129 mice) astrocytes were cultured (approximately 1 to 2 weeks) and loaded with Calcein (a green fluorescent dye) to mark cytoplasmic volume of astrocytes, then stimulated with electrical stimulation (2 Hz frequency square wave, 0.1 ms pulse width and 5 mV/mm electrical field potential generated from a stimulus isolator (A365 from World Precision Instruments) to a perfusion inserts (RC-37FS from Warner Instruments)). Sequential images (FIG. 1) showing EVs released during ES were taken under fluorescent microscopy (Olympus IX73 equipped with a Lambda 10-3 from Sutter Instrument to control a Xeon Arc Bulb, excitation filter 485/20, Emission filter 530/25) at time=0 seconds (A), 16 seconds (B), 20 seconds (C), 60 seconds (D), 72 seconds (E), and 120 seconds (F). It was found that ambient ES affects EV release from mouse primary cultured astrocytes (FIG. 1). Outward budding and vesicle shedding at the plasma membrane occurred when ES was applied. The applied field magnitude was determined through a test varying the field strength in stepwise lowering from a point as high as 100 mV/mm. It was found that high magnitude fields kill most cells, but at or below 5 mV/mm most cells are sustainable to ES. Field magnitudes at or below 5 mV/mm are within the range of endogenous electrical fields generated by neuronal populations measured from hippocampus[65].

Example 2: miRNA Modification with Electrical Stimulation

Figure 2:
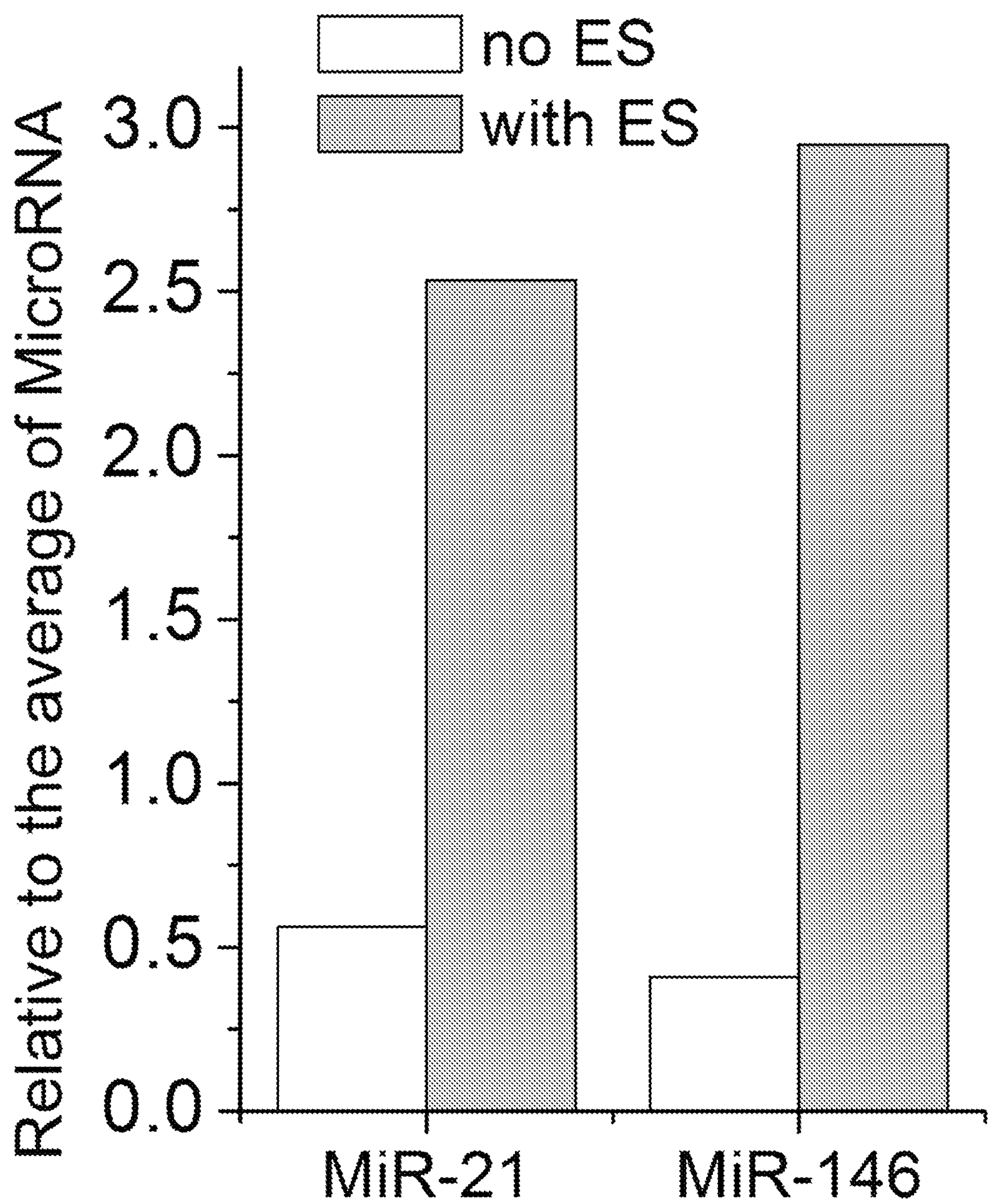
FIG. 2 is a graph showing the relative expression of miRNA in various samples as described in Example 2.

Primary mouse astrocytes were cultured. EVs were sampled and analyzed for miRNA content of miR-21 and miR-146 from 1) astrocytes not subject to electrical stimulation, and 2) astrocytes with electrical stimulation. Results are shown in FIG. 2.

Example 3: In Vitro Studies of Primary Cultures of Murine Neurons and Brain Slice Substrates The therapeutic effect of Ase-EVs collected under a stimulation parameter that has been used in restorative therapy for focal epilepsy and proven to be effective in both epilepsy patients and dogs with naturally occurring epilepsy is examined. Ase-EVs are collected under electrical stimulation, and each sample is characterized (concentration and size distribution) by nanoparticle tracking analysis using a NanoSight (NS300) device equipped with appropriate software for this task.

In vitro studies of primary cultures of murine neurons and brain slice substrates are used to evaluate the direct effects of astrocyte-derived EVs on neurons. Substrates of cultured neurons and brain slices from both wild type and genetically modified mice (miR-21-null or miR-146-null), available from Jackson Laboratories (miR-21 null mice, B6:129S6_Mir21atm1Yoli; miR-146 null mice: B6.Cg-Mir146tm1.1Bal/J) are used.

To investigate the possibility that astrocyte-derived EVs may not target neurons directly, but through intermediary astroglial or microglial cells, mixed cultures of neurons, astrocytes and microglia, or cultures of neurons and astrocytes depleted of microglia by clodrosome treatment are also examined. Mixture culture preparations have been successfully used as platforms for studying neuron-glia interactions[18].

Brain slice electrophysiology allows synaptic circuitry to be studied in isolation from the rest of the brain[19]. Besides large-scale synchronized neuronal activities, local field potentials generated from a small group of neurons after electrical stimulation are often used to represent functional neuronal communications at the synaptic level. Study of long-term potentiation based on local field potentials is used an additional method to determine whether astrocyte-derived EVs affect neural circuitry.

An established multi-electrode array (MEA) technique is used to detect synchronized neuronal activity, both singly and in synchronized firing, and examine the functional effects of astrocyte-derived EVs on neurons. The cultured neuronal substrate is a simple platform that avoids input from glial cells. The brain slice substrate, on the other hand, maintains the integrity of neuron-glia contacts thus simulating a more native environment. Both substrates allow access for drug application. Neuronal activity is enhanced either by increasing extracellular K+ concentration to alter the neuron's reversal potential, or by adding a GABAergic antagonist (bicuculline) to suppress inhibitory neuronal input.

Neuronal synchronization is defined as a coincidence in time of two or more events reflecting neuronal electrical activity. Spontaneous emergence of synchronized periodic bursting can be observed in a network of cultured dissociated neurons from mouse hippocampus and cortex. These periodic bursts of highly synchronized network activity typically last up to several seconds. Although simplified with respect to brain circuitry, this study will illustrate the contribution of single neuronal excitatory mechanisms to the formation of neural circuits.

In preliminary studies the inventors used MEA to monitor spontaneous activity in hippocampal slice preparations in 64 different locations continuously and simultaneously. Here the same technology is applied to dissociated neuronal cultures to simultaneously monitor firing activity in 64 individual neurons. MEA recordings with stable bursting amplitude and frequency are identified by Fast Fourier Analysis, focusing on three measurement modalities: interburst intervals (IBIs), quiet time between bursts and peaked distributions. The coefficient of variation of IBI distribution is indicative of well-defined oscillation frequency. These parameters are used to determine effects of astrocyte-derived EVs.

A MED64 system (Alpha MED), equipped with software Mobius for data acquisition and analysis, and available in various application-specific packages such as spike frequency and waveform analysis, is used for the analysis.

The effect of Ase-EVs is determined by analyzing the neuronal functional parameters before and after incubating the substrates with Ase-EVs. In addition, qRT-PCR analysis and immunocyto/histochemistry are applied to determine whether Ase-EVs are capable of reducing, respectively, neuronal cytotoxicity and pro-inflammatory activation of astrocytes and microglia. Finally, the effects on these neuronal and brain slice substrates of EVs derived from similarly treated miRNA-null astrocytes (genetically modified miR-21-null or miR-146-null mice) are compared to the effects of EVs prepared from wild-type astrocytes.

Example 4: In Vivo Studies of miR-21 and miR-146 Knockout Strains of Mice

In vivo studies of miR-21 and miR-146 knockout strains of mice are used to investigate the role of Ase-EVs enriched with specific miRNAs. Ase-EVs are delivered by intravenous (i.v.) injection or intranasal delivery[20] to genetically modified mice (miR-21-null or miR-146-null), available from Jackson Laboratories (miR-21 null mice, B6:129S6_Mir21atm1Yoli; miR-146 null mice: B6.Cg-Mir146tm1.1Bal/J). Characteristic phenotypes have been reported for each strain with specific miRNA deficiency, and data pertinent to microRNA biology have been reported[11,12]. miRNA levels in brain tissue homogenates from mice at baseline and after intravenous (i.v.) injection or intranasal delivery of Ase-EVs from respective wild-type mice or miRNA-null mice are measured, quantitatively and qualitatively to determine if the Ase-EVs can permeate the blood-brain barrier, to reverse the miRNA deficiency.

Example 5: Astrocyte-Derived EVs in Epilepsy

Frequency of Electrical Brain Stimulation

The effects of EBS strongly depend on stimulation frequency: for parkinsonian and idiopathic tremor, high frequencies (>90 Hz) improve motor symptoms; lower frequencies (<50 Hz) are either ineffective or exacerbate symptoms[54]. In contrast, low frequency (<3 Hz) stimulation safely and effectively reduces the seizures in epilepsy[39,44].

To test the hypothesis that Ase-EVs mediate EBS therapeutic benefits, the frequency-dependence of Ase-EV generation by subjecting cultured mouse astrocytes to ambient electrical stimulation at low (2 Hz), intermediate (20 Hz) and high (200 Hz) frequencies is evaluated in vitro. Resulting EVs are evaluated for size and numbers (by nanoparticle tracking analysis) and cargo (quantitative western blot of astrocytic proteins [aquaporin-4, EAAT1, EAAT2 and GFAP] and genome-wide RNA profiles).

RNA-seq

Because epilepsy is driven by multiple cellular pathways that act in concert, an effective treatment may require targeting multiple pathways simultaneously. It is also likely that electrical stimulation changes multiple noncoding RNAs. The repertoire of both coding and noncoding RNA associated with Ase-EVs requires detailed investigation. An unbiased approach is taken to identify changes globally in all extracellular RNA (exRNA) in EVs.

Many types of stress increase the expression of small noncoding RNAs (Diebel et al., 2016). Cellular stress imposed by electrical stimulation can similarly induce release of EVs and exRNA. EV-bound miRNAs are only a portion of the total exRNA detected during stress response[24,50,51]. Although this example is focused on characterization of EV-bound exRNAs, the exRNA released from astrocytes in vitro is also investigated in association with extracellular proteins and cholesterol (Example 5A) and in microdialysates collected from murine brain (Example 5B) and patients in vivo (Example 5C).

In Vivo Microdialysis

Microdialysis is a validated and well-established technique for recovering and measuring exogenous and endogenous small molecules in the interstitial fluid of tissues, and has been applied recently to detect large extracellular proteins[56] and circulating miRNAs[23,62]. Unlike the heterogeneity of miRNAs in urine or blood, tissue-specific microdialysis provides higher sensitivity for analyzing a specific microenvironment. The recent availability of 1000-kD cut-off membranes for a large molecular-weight microdialysis probe (AtmosLM, from Eicom), enabling large pore microdialysis coupled with open flow microperfusion[48], allows determination of interstitial concentrations of exRNA.

Sex as a Variable

Localization-related symptomatic epilepsies are reported to be more frequent in men, and cryptogenic localization-related epilepsies more frequent in women[32]. Another study reported a greater male frequency of generalized epilepsy of unknown etiology, and female frequency of autonomic, visual, and psychic symptoms associated with non-acquired focal epilepsy[31]. Therefore, for the in vivo study of Example 5B, separate groups of mice are investigated based on sex. Twelve libraries are submitted for deep sequencing (six from male mice and six from female mice), and 12 or more libraries from patient samples to determine if similar non-coding RNAs are present in patient samples. An equal number of men and women are studied in Example 5C.

Example 5A: In Vitro Studies Using Primary Cultured Murine Astrocytes

In vitro studies using primary cultured murine astrocytes (As) are performed to characterize EVs released at baseline (EVs derived from astrocytes without electrical stimulation) and by electrical stimulation (modified astrocyte-derived EVs).

Media is collected from triplicate experiments and the release of EVs following electrical stimulation at 2, 20 and 200 Hz and in an untreated control is assessed. Nanosight technology (described in Example 2 above) is used to ascertain the differences in the size or concentration of particles released by electrical stimulation as compared to the control. Next, media is collected and total RNA is extracted to ascertain the complete repertoire of RNA released by electrical stimulation as compared to the untreated control. In order to obtain reproducible and robust data each treatment is conducted in triplicate and each treatment and a control is submitted for deep sequencing in triplicate (a total of 48 libraries for deep sequencing). Additional samples are interrogated by quantitative RT-PCR for any genes and noncoding RNAs that are consistently upregulated in expression (exceeding control levels) in three triplicates. Extracted RNA is submitted for deep sequencing using True-Seq library construction and RNA-Seq at the University of Minnesota Genomics Center (UMGC). Next, western blot and RNA mimic transfection is used to evaluate potential changes in target proteins of the identified exRNAs.

Example 5B: In Vivo Analysis of as-EVs and Cargos in the Extracellular Space of the Mouse Hippocampus Sampled by Microdialysis The microdialysis method is validated in three ways: 1) in vitro testing by putting the probe into EV samples collected from Example 5A, in which the size distribution and concentration is already known. This step allows estimation of EV recovery rate. 2) in vitro testing by putting the probe into murine cerebrospinal fluid (CSF). This step allows estimation of the EV recovery rate approximating the in vivo microenvironment. 3) in vivo testing of mice to compare EVs sampled from CSF and from hippocampal extracellular fluid microdialysate.

Samples of microdialysate are subjected to three ultracentrifugation steps. The first, low speed, (2,000 g) removes cell bodies. The supernate of step 1 is subjected to two higher speed spins (10,000 g and 100,000 g). The final supernate is used to extract total exRNA to ascertain the complete repertoire of RNA. EV-bound miRNA profiles is analyzed in each pellet fraction.

Example 5C: Characterization of EVs Derived In Vivo from Extracellular Fluid of Human Hippocampus Sampled by Microdialysis Intraoperatively Prior to Surgery for Intractable Seizures The techniques and findings obtained from mouse model studies in Examples 6A and 6B are extended to human subjects. The clinical practice of anterior temporal lobe resection for temporal lobe epilepsy[63,30] provides a unique opportunity to directly sample human hippocampal extracellular space for EV prior to surgical resection as the inventors have previously done to study pharmacological activation of hippocampal seizures[52], microelectrodes[29,55], and adenosine concentrations[49].

Figure 4A:
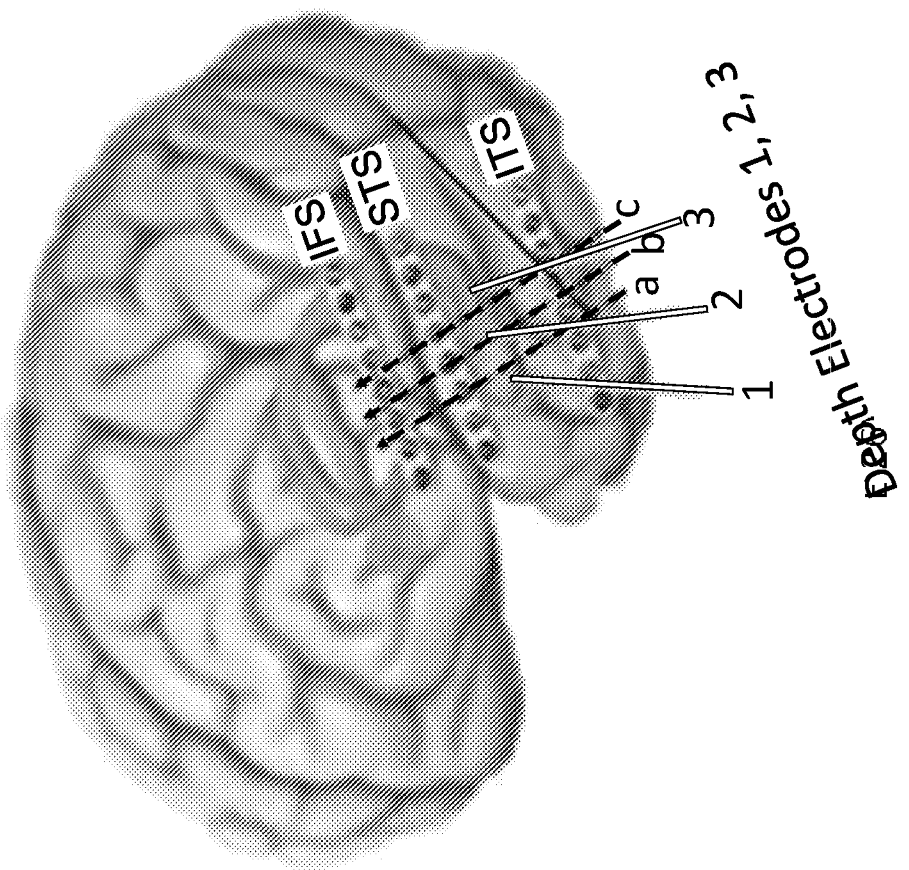
FIG. 4 shows an intra-operative microdialysis platform used in Example 5, including a standard clinical implant for temporal lobectomy (A), clinical depth electrode replaced by hybrid depth with inner cannula for microdialysis (B), and inner cannula for microdialysis (C).
Figure 4B:
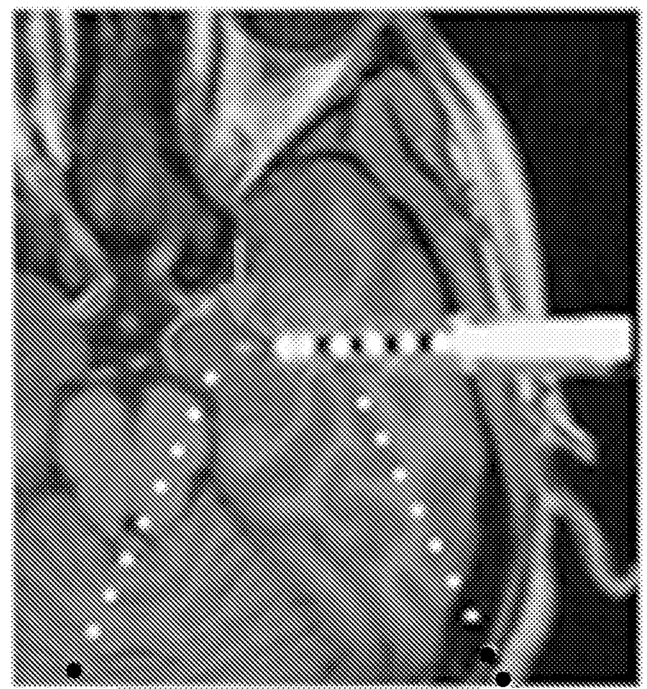
Figure 4C:
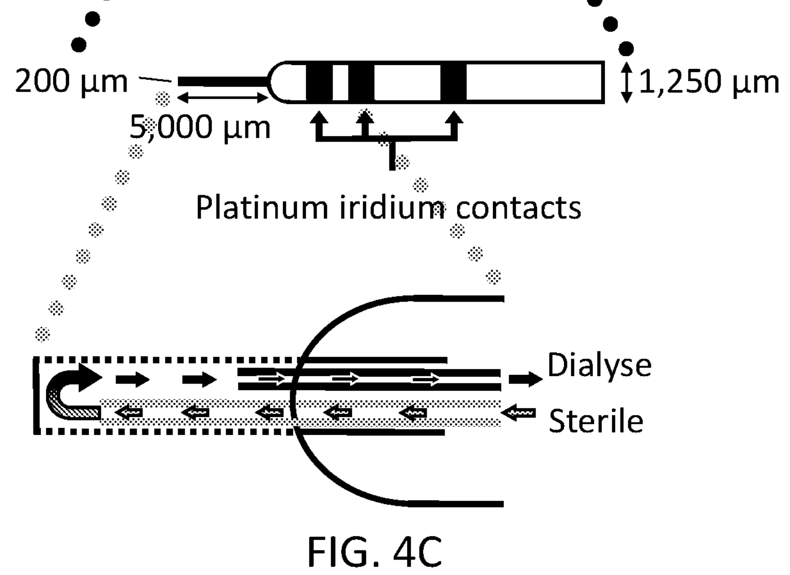

Patient Enrollment: 10 patients (5 women) with drug-resistant epilepsy who are candidates for temporal lobectomy are identified, informed of the study, and consented prior to epilepsy surgery. Per standard clinical practice, 3 depth electrodes targeting the hippocampus are placed prior to resection to verify epileptiform activity (FIG. 4): A) standard clinical implant for temporal lobectomy in which three depth electrodes (1,2,3) are placed laterally through the middle temporal gyrus into hippocampus, B) clinical depth electrode replaced by hybrid depth with inner cannula for microdialysis, C) inner cannula for microdialysis.

Anesthesia Protocol: Induction with sodium thiopental 3-5 mg/kg and fentanyl 2 μg/kg i.v., followed by vecuronium neuromuscular blockade. Anesthesia is maintained with inhaled 0.6% sevoflurane and 0.1-0.25 μg/kg-min remifentanil (RMF) i.v. infusion.

Depth Electrode Implantation (FIG. 4): The number and location of depth electrodes is standardized for clinical practice. The the clinical depth electrode is replaced with an FDA approved electrode having a central cannula for microdialysis. This study parallels the inventor's previous studies using research electrodes to record single neurons (Bower et al., 2015) and adenosine levels[49] and does not impact clinical decision making. The hippocampus head is targeted using MRI to ensure exact placement.

Intraoperative Microdialysis is performed prior to resection[28]. In patients undergoing depth electrode implantation, the clinical depth electrode is replaced by one with an inner cannula for microdialysis[28]. The electrophysiological data are unchanged from clinical practice. Microdialysis to collect extracellular fluid requires approximately 15 additional minutes of operative time. Extracellular fluid in the hippocampus is collected by microdialysis over a 5 minute period, under four separate conditions: 1) Resting state without electrical stimulation. This collection will occur during the standard intra-operative recording time for intracranial EEG. 2) Electrical Brain Stimulation (EBS) #1: Low frequency continuous stimulation (2.5 mA, 2 Hz, 100 ms pulse width minutes). 3) EBS #2: High frequency continuous stimulation (2.5 mA, 20 Hz, 100 ms pulse width minutes). 4) EBS #3: High frequency continuous stimulation (2.5 mA, 200 Hz, 100 ms pulse width minutes). EVs and cargo and exRNAs in all 4 collected dialysates is analyzed.

The profile of EVs (size & quantity) and cargo characteristics for each stimulation paradigm (2 Hz, 20 Hz, 200 Hz) are compared to baseline. The global miRNA expression in EVs is quantified as described in Examples 6A and 6B. The size profiles of EVs and the cargo profiles of miRNA is compared with data from in vitro and in vivo mouse studies.

Example 6: Selective Effect of ES on Release of Astrocyte EVs

To determine the selective effect of ES waveforms on the release of astrocytic EVs, a 5 mV/mm electric field was applied at three different frequencies: 2 Hz, 20 Hz and 200 Hz. These frequencies fall within the three typical endogenous brain oscillation frequencies recorded with intracranial electroencephalography (EEG), delta (0.5-4 Hz), beta-gamma (>12-30 Hz) and ripple (100-200 Hz) frequency oscillations. The three ES frequencies were applied to astrocyte cultures through a custom rig designed to create uniform fields over the astrocytes with continuous fluid exchange to collect the resulting EVs.

A newly established method using ultrafiltration combined with size-exclusion chromatography to separate EVs from other unspecific proteins, as described in Nordin et al.[22], was used to characterize EVs in detail. a fluorescently conjugated AQP4 antibody was used to indicate protein expression level. A nano-flow cytometer (N30 Nanoflow Analyzer, NanoFCM Inc., Xiamen, China) was used to segregate the EVs by size. Aquaporin-4 (AQP4) was targeted to quantify surface proteins on purified EVs. The AQP4 protein is a subclass of water channel expressed specifically in brain astrocytes. AQP4 expression on resulting EVs was characterized utilizing a custom made direct-conjugated monoclonal antibody to AQP4.

Figures 5A, 5B:
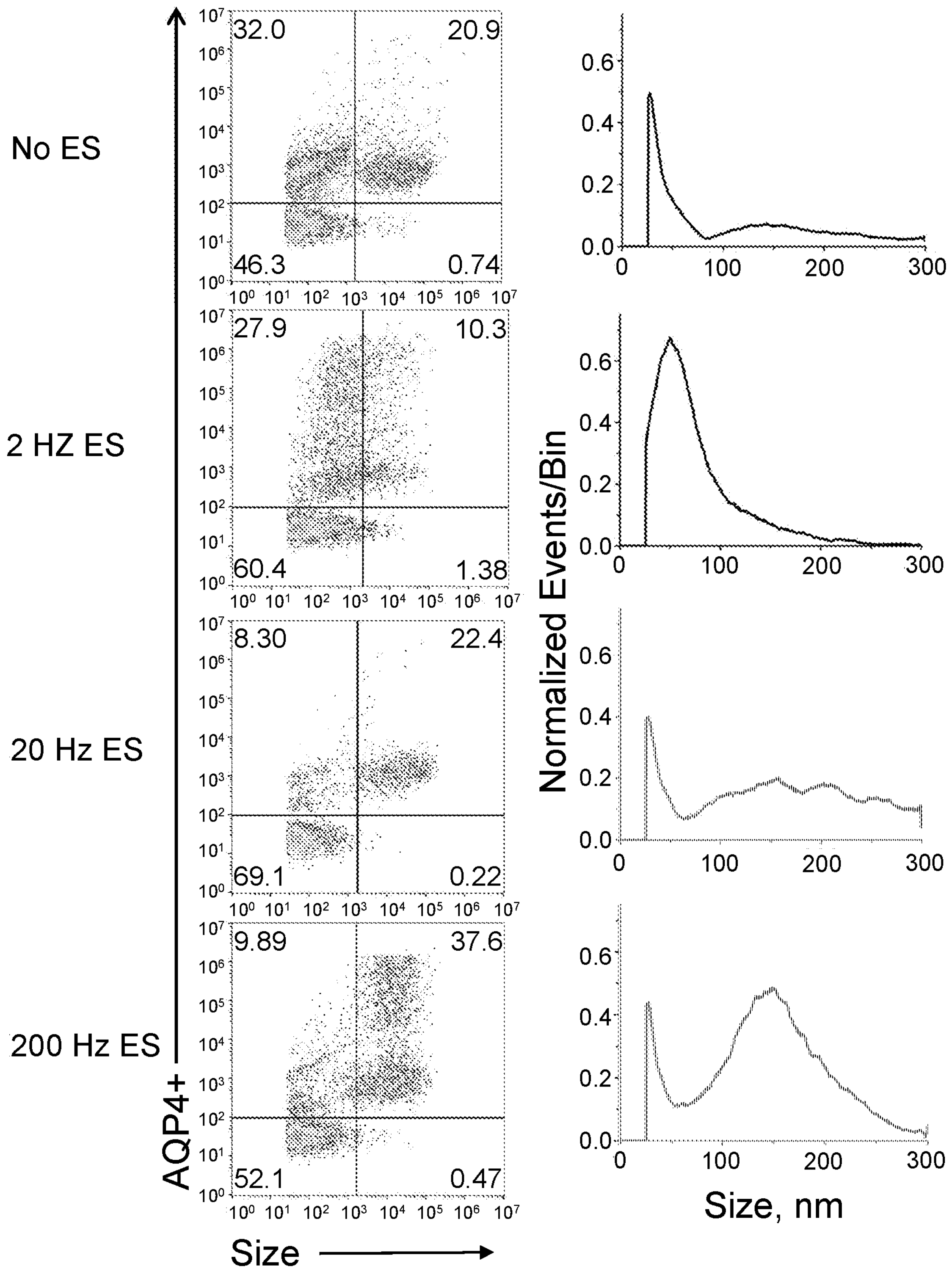
FIG. 5A is a series of density maps showing APQ4+EVs released under conditions of no electrical stimulation (no ES), electrical stimulation at 2 Hz (2 Hz ES), electrical stimulation at 20 Hz (20 Hz ES), and electrical stimulation at 200 Hz (200 Hz ES), according to Example 6.
FIG. 5B is a series of size distribution graphs showing size of APQ4+EVs released under conditions of no electrical stimulation (no ES), electrical stimulation at 2 Hz (2 Hz ES), electrical stimulation at 20 Hz (20 Hz ES), and electrical stimulation at 200 Hz (200 Hz ES), according to Example 6, and corresponding to the density maps in FIG. 5A.

FIGS. 5A and 5B show density plots and corresponding EV size distributions, respectively, of AQP4+EVs collected at different ES frequencies. FIG. 5A illustrates density maps of EVs from nano-flow cytometry experiments that show fluorescent intensity (y-axis) and the vesicle size (x-axis). In normal PBS media without applied ES, density plot from the nano-flow cytometry results show two distinguishable size populations of AQP4+EVs. At 2 Hz ES, the density map (FIG. 5A) shows one dominant AQP4 positive distribution that belongs to the smaller size EVs. At 20 Hz, the smaller size distribution is suppressed. At 200 Hz, the density map (FIG. 5A) shows one dominant distribution at larger size. Expression of AQP4 is also increased as indicated by the high fluorescent signal. FIG. 5B shows size distributions of corresponding EVs from FIG. 5A.

In general, EVs are subdivided into three major groups (exosomes, microvesicles and apoptotic bodies) primarily based on the release processes and vesicle diameter. Exosomes are released through exocytosis of endosomal multivesicular bodies and have a diameter between ~50-100 nm. Microvesicles (or ectosomes) are vesicles of ~100-1000 nm in diameter generated by outward budding and shedding from plasma membrane. Apoptotic bodies are released by apoptotic cells and generally possess dimensions larger than 1000 nm. In this example, the smaller sized group in the density map (FIG. 5A-5B) was characterized as exosomes and the larger sized group as microvesicles. Due to the resolution limitation of optical microscope (>100 nm), it is suggested that vesicles shedding visualized from cultured astrocytes in FIG. 1 are likely microvesicles.

It was unexpectedly found that the size distributions of AQP4+EVs are differentially effected by ES frequency. Using a uniform electric field (5 mV/mm), ES at 2 Hz produces a nearly single distribution of EVs with a peak at ~70 nm. The distribution is slightly shifted to larger EVs when compared to the smaller sized group of exosomes under control conditions. This group of AQP4+EVs still belongs to exosomes, but these exosomes have increased levels of AQP4 expression. ES at 20 Hz reduces the number of both EV groups observed in control conditions, with a greater reduction of exosomes. Lastly, ES at 200 Hz has the opposite effect of ES at 2 Hz, and instead of producing exosomes the dominant effect is to promote microvesicle release, with a size distribution peak at ~170 nm and increased level of microvesicle AQP4 expression. It was thus demonstrated in cultured murine astrocytes that ES frequency selectively affects release of EVs and their cargos (e.g., proteins).

Example 7: Alteration of EV miRNA Content with ES

Figure 6:
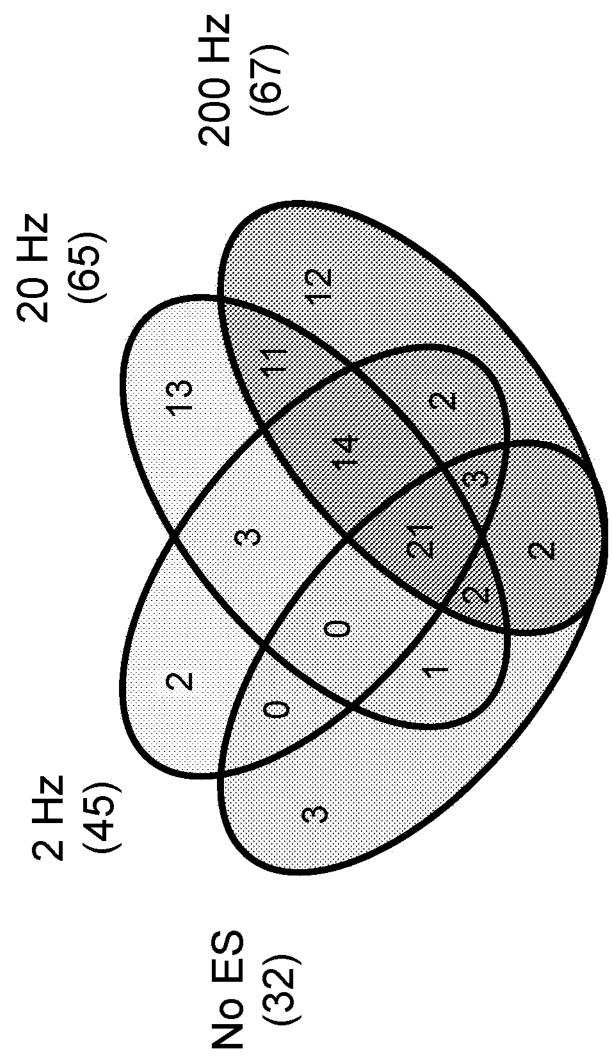
FIG. 6 is a Venn diagram showing the miRNAs distributions from RNA-seq collected from various samples as described in Example 7 and Table 1.

EV cargo, including the genetic materials (such as RNAs) can be another important aspect of EVs. Many types of stresses can increase the expression of small noncoding RNAs[35]. The cellular response to low amplitude ES to induce release of EVs and modulate miRNAs cargo was investigated. The effect of ES frequency on miRNA profiles was investigated through an unbiased approach using RNA-seq to identify changes in EVs miRNAs. RNAs were extracted from purified EVs collected respectively after applying a uniform electric field (5 mV/mm) at 2 Hz, 20 Hz, and 200 Hz ES, using reverse transcription to convert them to a cDNA library for a high-throughput sequencing. RNA-seq results are summarized in a Venn diagram (FIG. 6) with further details listed in Table 1. The Venn diagram in FIG. 6 shows four groups of miRNAs resulting from the RNA-seq of EVs collected from various conditions (No ES, ES at 2, 20, 200 Hz). Numbers of detected miRNAs are presented in the diagram for each section.

TABLE 1

| miRNA distributions | | |
|---|---|---|
| Group set of ES exposure No = baseline 2, 20, 200 Hz ES | Number of miRNA | miRNAs |
| No ∩ 2 ∩ 20 ∩ 200 | 21 | 423-5p, 4700-5p, 181a-5p, 92b-3p, 99b-5p, 320b, 23b-3p, 125b-5p, 27b-3p, 21-5p, 184, 23a-3p, 203a-3p, 125a-3p, 22-3p, 320a-3p, 103a-3p, 10a-5p, 27a-3p, 7704, 107 |
| 2 ∩ 20 ∩ 200-No | 14 | 148a-3p, 25-3p, let-7f-5p, 221-3p, 4492, let-7i-5p, let-7a-5p, 92a-3p, let-7c-5p, 125a-5p, 10b-5p, 151a-3p, 28-3p, 191-5p |
| No ∩ 2 ∩ 200-20 | 3 | 7977, 130a-3p, 143-3p |
| No ∩ 20 ∩ 200-2 | 2 | 26a-5p, 100-5p |

TABLE 1-continued

| miRNA distributions | | |
|---|---|---|
| Group set of ES exposure No = baseline 2, 20, 200 Hz ES | Number of miRNA | miRNAs |
| No ∩ 2 ∩ 20-200 | 0 | |
| No ∩ 2-20-200 | 0 | |
| No ∩ 20-2-200 | 1 | 3168 |
| No ∩ 200-2-20 | 2 | 1469, 4680-3p |
| 2 ∩ 20-No-200 | 3 | 4259, 205-5p, 3195 |
| 2 ∩ 200-No-20 | 2 | let-7b-5p, 30a-5p |
| 20 ∩ 200-No-2 | 11 | 30d-5p, 375-3p, 183-5p, 146b-5p, 378a-3p, 26b-5p, 9-5p, 222-3p, 423-3p, 744-5p, 99a-5p |
| No-2-20-200 | 3 | 4775, 4324, 662 |
| 2-No-20-200 | 2 | 4781-3p, 5100 |
| 20-No-2-200 | 13 | 361-5p, 125b-1-3p, 30d-3p, 125b-2-3p, 193b-3p, 141-3p, 24-3p, 5047, 21-3p, 129-5p, 151a-5p, 30a-3p, 210-3p |
| 200-No-2-20 | 12 | 6728-5p, 204-5p, 30e-5p, 98-5p, 186-5p, 486-5p, 10395-3p, 431-5p, 148b-5p, 182-5p, 3661, 6068 |

A total of 89 miRNAs were identified. The numbers of identified miRNAs in each sample of EVs collected under four conditions are: No ES (32), ES at 2 Hz (45), ES at 20 Hz (65) and ES at 200 Hz (67). Twenty one miRNAs were present in all four groups, 66% in control with No ES, 47% with 2 Hz, 32% with 20 Hz and 31% with 200 Hz. Thus, fourteen miRNAs are specifically associated with ES regardless of stimulation frequency. However, each ES frequency studied (2, 20, and 200 Hz) has a unique set of miRNAs. It was thus demonstrated in cultured murine astrocytes that ES frequency selectively affects EV cargos (e.g., miRNAs).

Example 8: Suppression of PD-L1 in Cancer

Figure 7:
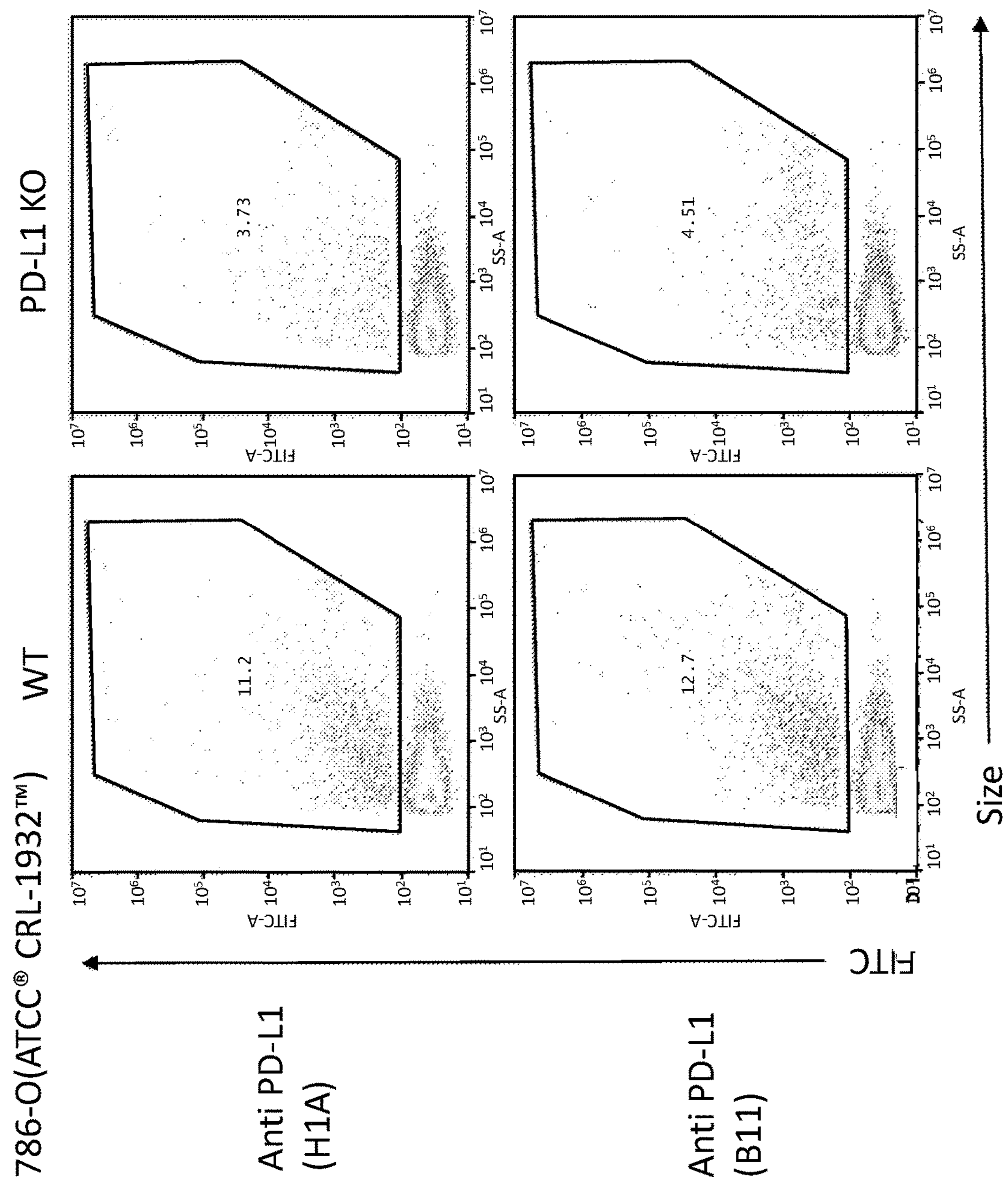
FIG. 7: is a series of density maps showing positive signals using antibodies to PD-L1 for exosomal PD-L1 in WT compared to PD-L1 KO (~12% vs ~4%) in the 786-0 cell line.
Figure 8:
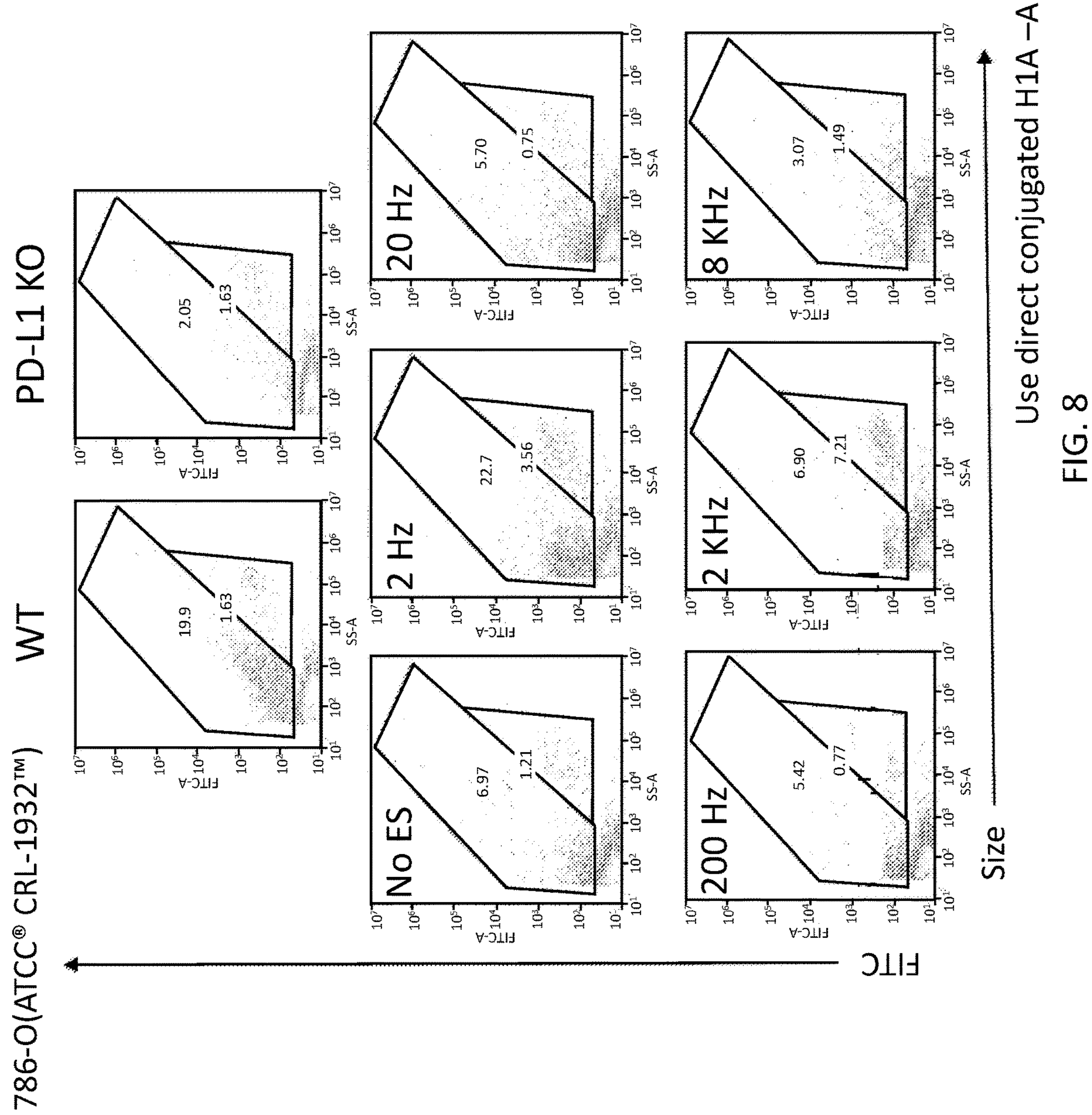
FIG. 8 is a series of density maps showing plots of FITC vs. EV size at different electrical stimulation (ES) frequencies of about 2 Hz, 20 Hz, 200 Hz, 2 KHz, and 8 KHz.

The effect of ES waveforms on the release of EVs in cancer cells was investigated. A 5 mV/mm electric field was applied to 786-0 (ATCC CRL-1932) renal adenocarcinoma cells at multiple different frequencies: 2 Hz, 20 Hz, 200 Hz, 2 KHz, and 8 KHz. No electrical stimulation on the renal adenocarcinoma cells, wild-type cells (WT), and PD-L1 knock-out cells (PD-L1 KO) was also investigated. Nano-flow cytometry and anti-bodies to PD-L1 were used to determine the release of EVs carrying PD-L1 and the amount of PD-L1 carried by released EVs. Ultrafiltration was combined with size-exclusion chromatography to separate EVs from extrinsic proteins. A nano-flow cytometer (N30 Nanoflow Analyzer, NanoFCM Inc., Xiamen, China) was used to separate the EVs by size, and surface proteins on purified EVs were quantified using an extracellular domain-specific PD-L1 anti-body. FIGS. 7 and 8 show particle numbers and sizes corresponding to EVs collected at baseline and at different stimulation frequencies. The series of density maps of FIG. 7 show that in, the 786-0 cell line, both antibodies to PD-L1 revealed a high percentage of positive signals for exosomal PD-L1 in WT compared to PD-L1 KO (~12% vs ~4%). The results indicate the usefulness of nano-flow cytometry combined with PD-L1 antibodies in quantifying PD-L1 positive exosomes. Similar experiments were performed for MAD-MB-231 breast adenocarcinoma cells.

As shown in FIG. 8, ES suppresses release of EVs and of PD-L1, particularly at frequencies of ~20 Hz or greater, such as for 20 Hz, 200 Hz, 2 KHz, and 8 KHz shown in FIG. 8. It was found that ES suppresses PD-L1 carried by EVs in renal cell adenocarcinoma (786-0) and breast adenocarcinoma (MAD-MB-231).

Example 9: Exosomal PD-L1 as a Biomarker

Figure 9:
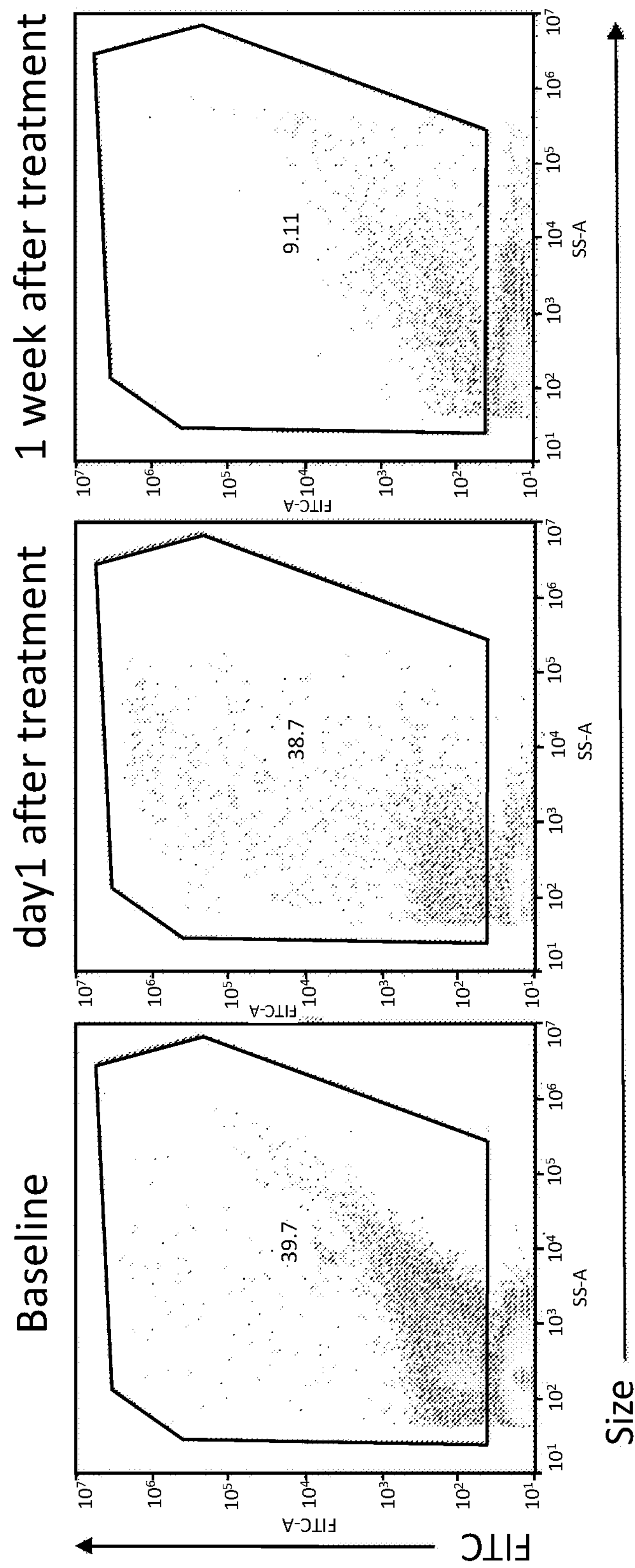
FIG. 9 is a series of density maps showing distribution of PD-L1 positive exosomes in patient samples taken at three time points: before treatment, on day 1 after treatment, and 1 week after treatment, according to Example 11.

Two monoclonal PD-L1 antibodies were developed for exosomal PD-L1 detection. Using a nano-flow cytometer, the PD-L1 antibodies were first applied to exosomes collected from culture media of the wildtype and PD-L1 KO 786-O cell line, as described in Example 8 and FIG. 7. Next, this method was applied to blood samples of a cancer patient. Patient exosomes were collected before radiotherapy treatment (baseline), and at one day, and one week after treatment, the results of which are shown in FIG. 9.

In the 786-O cell line, both antibodies revealed a high percentage of positive signals for exosomal PD-L1 in WT compared to PD-L1 KO (~12% vs ~4%). These results indicate the usefulness of nano-flow cytometry in quantifying PD-L1 positive exosomes. For the patient blood samples, as shown in FIG. 9, the density map of baseline shows a linear distribution of PD-L1 positive exosomes in ~40% of the total exosome population. After one day of treatment, the density map shows a scattered distribution, although the PD-L1 positive exosomes remained in ~40%. However, after one week of treatment the PD-L1 positive exosomes reduced to ~10% of total population, suggesting the effectiveness of the treatment and the usefulness of exosomal PD-L1 detection in evaluating treatments effectiveness.

Example 10: Suppression of PD-L1 in Glioblastoma

The methods of Example 8 are applied to U-87 glioblastoma cells.

Example 11: In Vivo Suppression of PD-L1 in Glioblastoma

Mice are implanted with human brain glioblastoma tissue. Transcranial ES or direct brain ES is applied at multiple different frequencies: 2 Hz, 20 Hz, 200 Hz, 2 KHz, and 8 KHz, as described in Example 8. Tumors are evaluated for tumor spread.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Peng, B., Chen, Y. & Leong, K. W. MicroRNA delivery for regenerative medicine. *Adv. Drug Deliv. Rev.* 88, 108-122 (2015).
2. Li, Z. & Rana, T. M. Therapeutic targeting of microRNAs: current status and future challenges. *Nat. Publ. Gr.* 13, (2014).
3. Yu, X., Odenthal, M. & Fries, J. W. U. Exosomes as miRNA carriers: Formation-function-future. *International Journal of Molecular Sciences* 17, (2016).
4. Chan, J. A., Krichevsky, A. M. & Kosik, K. S. MicroRNA-21 is an antiapoptotic factor in human glioblastoma cells. *Cancer Res.* 65, 6029-6033 (2005).
5. Roos, J. et al. miR-146a-mediated suppression of the inflammatory response in human adipocytes. *Sci. Rep.* (2016).
6. Jimenez-Mateos, E. M. & Henshall, D. C. Epilepsy and microRNA. *Neuroscience* (2013).
7. Lundstrom, B. N., Worrell, G. A., Stead, M. & Van Gompel, J. J. Chronic subthreshold cortical stimulation: a therapeutic and potentially restorative therapy for focal epilepsy. *Expert Rev. Neurother.* 17, 661-666 (2017).
8. Apweiler, R. et al. Deep brain stimulation modulates nonsense-mediated RNA decay in Parkinson's patients leukocytes. *Nucleic Acids Res.* 29, 37-40 (2001).
9. Rufino-Ramos, D. et al. Extracellular vesicles: Novel promising delivery systems for therapy of brain diseases. *Journal of Controlled Release* 262, 247-258 (2017).
10. Campbell, C. R., Berman, A. E., Weintraub, N. L. & Tang, Y. L. Electrical stimulation to optimize cardioprotective exosomes from cardiac stem cells. *Med. Hypotheses* (2016).
11. He, W. et al. MiR-21 is required for anti-tumor immune response in mice: an implication for its bi-directional roles. *Nat. Publ. Gr.* 36, 4212-4223 (2017).
12. Zhao, J. L., Rao, D. S., O'connell, R. M., Garcia-Flores, Y. & Baltimore, D. MicroRNA-146a acts as a guardian of the quality and longevity of hematopoietic stem cells in mice. *Elife* 2, (2013).
13. Peng, J. et al. Expression patterns of miR-124, miR-134, miR-132, and miR-21 in an immature rat model and children with mesial temporal lobe epilepsy. *J Mol. Neurosci.* 50, 291-297 (2013).
14. Gorter, J. A. et al. Hippocampal subregion-specific microRNA expression during epileptogenesis in experimental temporal lobe epilepsy. *Neurobiol. Dis.* (2014).
15. Zhou, K. et al. A method for extracting and characterizing RNA from urine: For downstream PCR and RNAseq analysis. *Anal. Biochem.* 536, 8-15 (2017).
16. Papadopoulos, M. C., Saadoun, S. & Verkman, A. S. Aquaporins and cell migration. *Pflugers Archiv European Journal of Physiology* 456, 693-700 (2008).
17. Hiroaki, Y. et al. Implications of the aquaporin-4 structure on array formation and cell adhesion. *J. Mol. Biol.* 355, 628-639 (2006).
18. Chen, S.-H., Oyarzabal, E. A. & Hong, J.-S. Preparation of rodent primary cultures for neuron-glia, mixed glia, enriched microglia, and reconstituted cultures with microglia. *Methods Mol. Biol.* 1041, 231-40 (2013).
19. Cho, S., Wood, A. & Bowlby, M. R. Brain Slices as Models for Neurodegenerative Disease and Screening Platforms to Identify Novel Therapeutics. *Curr. Neuropharmacol.* 5, 19-33 (2007).
20. Lochhead, J. J. & Thorne, R. G. Intranasal delivery of biologics to the central nervous system. *Adv. Drug Deliv. Rev.* 64, 614-628 (2012).
21. E L Andaloussi, S. et al., 2013. Extracellular vesicles: biology and emerging therapeutic opportunities. Nature Reviews Drug Discovery.
22. Wang, K. et al., 2017. TNF-α promotes extracellular vesicle release in mouse astrocytes through glutaminase. Journal of Neuroinflammation.
23. Abrahamsson, A., Dabrosin, C., 2015. Tissue specific expression of extracellular microRNA in human breast cancers and normal human breast tissue in vivo. Oncotarget 6, 22959-22969.
24. Arroyo, J. D., Chevillet, J. R., Kroh, E. M., Ruf, L K., Pritchard, C. C., Gibson, D. F., Mitchell, P. S., Bennett, C. F., Pogosova-Agadjanyan, E. L., Stirewalt, D. L., Tait, J. F., Tewari, M., 2011. Argonaute2 complexes carry a population of circulating microRNAs independent of vesicles in human plasma. Proc. Natl. Acad. Sci. 108, 5003-5008.
25. Aspelund, A., Antila, S., Proulx, S. T., Karlsen, T. V., Karaman, S., Detmar, M., Wiig, H., Alitalo, K., 2015. A dural lymphatic vascular system that drains brain interstitial fluid and macromolecules. J. Exp. Med. 212, 991-999.
26. Bache, S., Rasmussen, R., et al., 2009. Epilepsy surgery outcomes in temporal lobe epilepsy with a normal MRI. Epilepsia 50, 2053-2060.
27. Bergey, G. K., Morrell, M. J., et al., 2015. Long-term treatment with responsive brain stimulation in adults with refractory partial seizures. Neurology 84, 810-817.
28. Blouin, A. M., Fried, I., et al., 2013. Human hypocretin and melanin-concentrating hormone levels are linked to emotion and social interaction. Nat. Commun. 4, 1547. doi:10.1038/ncomms2461
29. Bower, M. R., Stead, M., et al., 2015. Evidence for Consolidation of Neuronal Assemblies after Seizures in Humans. J. Neurosci. 35, 999-1010.
30. Burkholder, D. B., Sulc, V., et al., 2014. Interictal Scalp Electroencephalography and Intraoperative Electrocorticography in Magnetic Resonance Imaging-Negative Temporal Lobe Epilepsy Surgery. JAMA Neurol. 71, 702.
31. Carlson, C., Dugan, P., Kirsch, H. E., Friedman, D., 2014. Sex differences in seizure types and symptoms. Epilepsy Behav. 41, 103-108.
32. Christensen, J., Kjeldsen, M. J., Andersen, H., Friis, M. L., Sidenius, P., 2005. Gender Differences in Epilepsy. Epilepsia 46, 956-960.
33. Deeb, W., Giordano, J. J., et al., 2016. Proceedings of the Fourth Annual Deep Brain Stimulation Think Tank: A Review of Emerging Issues and Technologies. Front. Integr. Neurosci. 10, 38.
34. Dickens, A. M., Tovar-y-Romo, L. B., et al., 2017. Astrocyte-shed extracellular vesicles regulate the peripheral leukocyte response to inflammatory brain lesions. Sci. Signal. 10.
35. Diebel, K. W., Zhou, K., Clarke, A. B., Bemis, L. T., 2016. Beyond the ribosome: Extra-translational functions of tRNA fragments. Biomark. Insights 11, 1-8.
36. Ezzyat, Y., Kragel, J. E., et al., 2017. Direct Brain Stimulation Modulates Encoding States and Memory Performance in Humans. Curr. Biol. 27, 1251-1258.

37. Fang, B., McKeon, A., et al., 2016. Autoimmune Glial Fibrillary Acidic Protein Astrocytopathy. JAMA Neurol. 73, 1297.

38. Fisher, R., Salanova, V., et al, 2010. Electrical stimulation of the anterior nucleus of thalamus for treatment of refractory epilepsy. Epilepsia 51, 899-908.

39. Kile, K. B., Tian, N., Durand, D. M., 2010. Low Frequency Stimulation Decreases Seizure Activity in a Mutation Model of Epilepsy. Epilepsia 51, 1745-1753.

40. Lafourcade, C., Pablo Ramirez, J., Luarte, A., Fernández, A., Wyneken, U., 2016. MiRNAs in Astrocyte-Derived Exosomes as Possible Mediators of Neuronal Plasticity Supplementary Issue: Brain Plasticity and Repair. J. Exp. Neurosci. 1010, 1-9.

41. Langevin, J.-P., Koek, R. J., Schwartz, H. N., Chen, J. W. Y., Sultzer, D. L., Mandelkern, M. A., Kulick, A. D., Krahl, S. E., 2016. Deep Brain Stimulation of the Basolateral Amygdala for Treatment-Refractory Posttraumatic Stress Disorder. BPS 79, e82-e84.

42. Laxton, A. W., Tang-Wai, D. F., McAndrews, M. P., Zumsteg, D., Wennberg, R., Keren, R., Wherrett, J., Naglie, G., Hamani, C., Smith, G. S., Lozano, A. M., 2010. A phase I trial of deep brain stimulation of memory circuits in Alzheimer's disease. Ann. Neurol. 68, 521-534. doi:10.1002/ana.22089

43. Lozano, A. M., Fosdick, L., et al., 2016. A Phase II Study of Fornix Deep Brain Stimulation in Mild Alzheimer's Disease. J. Alzheimer's Dis. 54, 777-787. doi:10.3233/JAD-160017

44. Lundstrom, B. N., Van Gompel, J., Britton, J., Nickels, K., Wetjen, N., Worrell, G., Stead, M., 2016. Chronic Subthreshold Cortical Stimulation to Treat Focal Epilepsy. JAMA Neurol. 73, 1370. doi:10.1001/jamaneurol.2016.2857

45. Mayberg, H. S., Lozano, A. M., Voon, V., McNeely, H. E., Seminowicz, D., Hamani, C., Schwalb, J. M., Kennedy, S. H., 2005. Deep brain stimulation for treatment-resistant depression. Neuron 45, 651-660. doi:10.1016/j.neuron.2005.02.014

46. Raymaekers, S., Luyten, L., Bervoets, C., Gabriëls, L., Nuttin, B., 2017. Deep brain stimulation for treatment-resistant major depressive disorder: a comparison of two targets and long-term follow-up. Nat. Publ. Gr. 766. doi:10.1038/tp.2017.66

47. Srivastava, A., Dixit, A. B., Banerjee, J., Tripathi, M., Sarat Chandra, P., 2016. Role of inflammation and its miRNA based regulation in epilepsy: Implications for therapy. Clin. Chim. Acta.

48. Takeda, S., Sato, N., Ikimura, K., Nishino, H., Rakugi, H., Morishita, R., 2011. Novel microdialysis method to assess neuropeptides and large molecules in free-moving mouse. Neuroscience.

49. Van Gompel, J. J., Bower, M. R., Worrell, G. A., Stead, M., Chang, S.-Y., Goerss, S. J., Kim, I., Bennet, K. E., Meyer, F. B., Marsh, W. R., Blaha, C. D., Lee, K. H., 2014. Increased cortical extracellular adenosine correlates with seizure termination. Epilepsia 55, 233-244.

50. Vickers, K. C., Palmisano, B. T., Shoucri, B. M., Shamburek, R. D., Remaley, A. T., 2011. MicroRNAs are transported in plasma and delivered to recipient cells by high-density lipoproteins. Nat. Cell Biol. 13, 423-443.

51. Wang, K., Zhang, S., Weber, J., Baxter, D., Galas, D. J., 2010. Export of microRNAs and microRNA-protective protein by mammalian cells. Nucleic Acids Res. 38, 7248-7259.

52. Wass, C. T., Grady, R. E., Fessler, A. J., Cascino, G. D., Lozada, L., Bechtle, P. S., Marsh, W. R., Sharbrough, F. W., Schroeder, D. R., 2001. The Effects of Remifentanil on Epileptiform Discharges during Intraoperative Electrocorticography in Patients Undergoing Epilepsy Surgery. Epilepsia 42, 1340-1344.

53. Witwer, K. W., Buzás, E. I., Bemis, L. T., Bora, A., Lässer, C., Lötvall, J., Nolte-'t Hoen, E. N., Piper, M. G., Sivaraman, S., Skog, J., Théry, C., Wauben, M. H., Hochberg, F., 2013. Standardization of sample collection, isolation and analysis methods in extracellular vesicle research. J. Extracell. Vesicles 2, 20360.

54. Wojtecki, L., Moldovan, A.-S., Groiss, S. J., Elben, S., Südmeyer, M., Schnitzler, A., 2015. The treatment of Parkinson's disease with deep brain stimulation: current issues. NEURAL Regen. Res. 10.

55. Worrell, G. A., Jerbi, K., Kobayashi, K., Lina, J. M., Zelmann, R., Le Van Quyen, M., 2012. Recording and analysis techniques for high-frequency oscillations. Prog. Neurobiol.

56. Yamada, K., Cirrito, J. R., Stewart, F. R., Jiang, H., Finn, M. B., Holmes, B. B., Binder, L. I., Mandelkow, E.-M., Diamond, M. I., Lee, V. M.-Y., Holtzman, D. M., 2011. In Vivo Microdialysis Reveals Age-Dependent Decrease of Brain Interstitial Fluid Tau Levels in P301S Human Tau Transgenic Mice. J. Neurosci.

57. Yan, S., Zhang, H., Xie, W., Meng, F., Zhang, K., Jiang, Y., Zhang, X., Zhang, J., 2017. Altered microRNA profiles in plasma exosomes from mesial temporal lobe epilepsy with hippocampal sclerosis. Oncotarget 8, 4136-4146.

58. Yang, L., Kress, B. T., Weber, H. J., Thiyagarajan, M., Wang, B., Deane, R., Benveniste, H., Iliff, J. J., Nedergaard, M., 2013. Evaluating glymphatic pathway function utilizing clinically relevant intrathecal infusion of CSF tracer. J. Transl. Med. 11, 107.

59. Zekeridou, A., Lennon, V. A., 2015. Aquaporin-4 autoimmunity. Neurol. Neuroimmunol. neuroinflammation 2, e110.

60. Furman C S, Gorelick-Feldman D A, Davidson K G V, Yasumura T, Neely J D, Agre P, et al. Aquaporin-4 square array assembly: Opposing actions of M1 and M23 isoforms. Proc Natl Acad Sci USA. 2003; 100:13609-14. doi: 10.1073/pnas.2235843100.

61. Shen B. et al, Protein Targeting to Exosomes/Microvesicles by Plasma Membrane Anchors. J. Biol. Chem. 2011, 286:14383-14395.

62. Bache et al. Detection and quantification of microRNA in cerebral microdialysate Journal of Translational Medicine (2015) 13:149.

63. Bell M L et al, Epilepsy surgery outcomes in temporal lobe epilepsy with a normal MRI. Epilepsia, 50(9):2053-2060, 2009.

64. Li, M M. et al. MicroRNAs dysregulation in Epilepsy. Brain Research. 2014, 1584 (94-104).

65. S. Weiss, D. Faber, Field effects in the CNS play functional roles. Front. Neural Circuits. 4, 1-10 (2010).

66. R. D. Fields, B. Stevens-graham, New Insights into Neuron-Glia

Communication. Science (80-.). 298, 556-562 (2002).

67. G. Perea, M. Sur, A. Araque, Neuron-glia networks: integral gear of brain function. Front. Cell. Neurosci. 8, 378 (2014).

68. M. Nedergaard, B. Ransom, S. a. Goldman, New roles for astrocytes: Redefining the functional architecture of the brain. Trends Neurosci. 26, 523-530 (2003).

69. H. Monai, H. Hirase, Astrocytic calcium activation in a mouse model of tDCS—Extended discussion. Neurogenesis. 3, 1-7 (2016).

70. H. Monai, H. Hirase, Astrocytes as a target of transcranial direct current stimulation (tDCS) to treat depression. Neurosci. Res. 126 (2018), pp. 15-21.
71. J. Z. Nordin et al., Ultrafiltration with size-exclusion liquid chromatography for high yield isolation of extracellular vesicles preserving intact biophysical and functional properties. Nanomedicine Nanotechnology, Biol. Med. 11, 879-883 (2015).
72. C. A. Anastassiou, R. Perin, H. Markram, C. Koch, Ephaptic coupling of cortical neurons. Nat. Neurosci. 14, 217-224 (2011).
73. M. A. Nitsche et al., Transcranial direct current stimulation: State of the art 2008. Brain Stimul. 1 (2008), pp. 206-223.
74. R. S. Fisher, Therapeutic devices for epilepsy. Ann. Neurol. 71, 157-168 (2012).
75. S. Toprani, D. M. Durand, Long-lasting hyperpolarization underlies seizure reduction by low frequency deep brain electrical stimulation. J. Physiol. 591, 5765-5790 (2013).
76. M. Z. Koubeissi, F. Bartolomei, A. Beltagy, F. Picard, "Electrical stimulation of a small brain area reversibly disrupts consciousness" (2014), doi:10.1016/j.yebeh.2014.05.027.
77. M. T. Kucewicz et al., Evidence for verbal memory enhancement with electrical brain stimulation in the lateral temporal cortex. Brain. 141, 971-978 (2018).
78. R. Stupp et al., NovoTTF-100A versus physician's choice chemotherapy in recurrent glioblastoma: a randomised phase III trial of a novel treatment modality. Eur. J. Cancer. 48, 2192-202 (2012).
79. G. Deuschl et al., A Randomized Trial of Deep-Brain Stimulation for Parkinson's Disease. N. Engl. J. Med. 355, 896-908 (2006).
80. M. Rodrigues, J. Fan, C. Lyon, M. Wan, Y. Hu, Role of Extracellular Vesicles in Viral and Bacterial Infections: Pathogenesis, Diagnostics, and Therapeutics. Theranostics. 8, 2709-2721 (2018).
81. A. Becker et al., Extracellular Vesicles in Cancer: Cell-to-Cell Mediators of Metastasis. Cancer Cell. 30 (2016), pp. 836-848.
82. D. Turpin et al., Role of extracellular vesicles in autoimmune diseases. Autoimmun. Rev. 15, 174-183 (2016).
83. D. Turpin et al., Role of extracellular vesicles in autoimmune diseases. Autoimmun. Rev. 15, 174-183 (2016).
84. X. Yu, M. Odenthal, J. W. U. Fries, Exosomes as miRNA carriers: Formation-function-future. Int. J. Mol. Sci. 17 (2016), doi:10.3390/ijms17122028.
85. M. Yáñez-Mó et al., Biological properties of extracellular vesicles and their physiological functions. J. Extracell. Vesicles. 4 (2015), pp. 1-60.
86. J. De Toro, L. Herschlik, C. Waldner, C. Mongini, Emerging roles of exosomes in normal and pathological conditions: New insights for diagnosis and therapeutic applications. Front. Immunol. 6, 1-12 (2015).
87. E. N. M. Nolte-'t Hoen, M. H. M. Wauben, Immune Cell-derived Vesicles: Modulators and Mediators of Inflammation. Curr. Pharm. Des. 18, 2357-2368 (2012).
88. E. J. van der Vlist et al., CD4+ T cell activation promotes the differential to release of distinct populations of nanosized vesicles. J. Extracell. Vesicles. 1, 1-9 (2012).
89. G. Buzsáki, Z. Horváth, R. Urioste, J. Hetke, K. Wise, High-frequency network oscillation in the hippocampus. Science (80-.). 256, 1025-1027 (1992).
90. A. Kamondi, L. Acsády, X. J. Wang, G. Buzsáki, Theta oscillations in somata and dendrites of hippocampal pyramidal cells in vivo: Activity-dependent phase-precession of action potentials. Hippocampus. 8, 244-261 (1998).
91. F. Rattay, The basic mechanism for the electrical stimulation of the nervous system. Neuroscience. 89, 335-346 (1999).
92. Chen, Lieping, and Xue Han. 2015. "Anti-PD-1/PD-L1 Therapy of Human Cancer: Past, Present, and Future." Journal of Clinical Investigation. American Society for Clinical Investigation. doi:10.1172/JCI80011.
93. Dong, Haidong, Scott E. Strome, Diva R. Salomao, Hideto Tamura, Fumiya Hirano, Dallas B. Flies, Patrick, C. Roche, et al. 2002. "Tumor-Associated B7-H1 Promotes T-Cell Apoptosis: A Potential Mechanism of Immune Evasion." Nature Medicine 8 (8). Nature Publishing Group: 793-800. doi:10.1038/nm730.
94. Patel, Sandip Pravin, and Razelle Kurzrock. 2015. "PD-L1 Expression as a Predictive Biomarker in Cancer Immunotherapy." Molecular Cancer Therapeutics 14 (4). American Association for Cancer Research: 847-56. doi: 10.1158/1535-7163.MCT-14-0983.
95. Chen, Gang, Alexander C Huang, Wei Zhang, Gao Zhang, Min Wu, Wei Xu, Zili Yu, et al. 2018. "Exosomal PD-L1 Contributes to Immunosuppression and Is Associated with Anti-PD-1 Response." Nature. doi:10.1038/s41586-018-0392-8.
96. Stupp, Roger, Eric T Wong, Andrew A Kanner, David Steinberg, Herbert Engelhard, Volkmar Heidecke, Eilon D Kirson, et al. 2012. "NovoTTF-100A versus Physician's Choice Chemotherapy in Recurrent Glioblastoma: A Randomised Phase III Trial of a Novel Treatment Modality." European Journal of Cancer (Oxford, England: 1990) 48 (14): 2192-2202. doi:10.1016/j.ejca.2012.04.011.
97. Kirson, Eilon D, Vladimir Dbalý, Frantisek Tovarys, Josef Vymazal, Jean F Soustiel, Aviran Itzhaki, Daniel Mordechovich, et al. 2007. "Alternating Electric Fields Arrest Cell Proliferation in Animal Tumor Models and Human Brain Tumors." Proceedings of the National Academy of Sciences of the United States of America 104 (24): 10152-57. doi:10.1073/pnas.0702916104.

What is claimed is:

1. A method of obtaining extracellular vesicles derived from a target cell exposed to electrical stimulation, wherein said method comprises:

(a) electrically stimulating said target cell in culture at 0.002 mV/mm to 5 mV/mm or at 4 mV/mm to 6 mV/mm, wherein said target cell releases said extracellular vesicles, and (b) collecting said extracellular vesicles from said target cell in culture, wherein said target cell is a cancer cell, a central nervous system neuron or glial cell, an immune system cell, a neural cell, a glial cell, or an endothelial cell.

2. The method of claim 1, wherein electrically stimulating said target cell comprises applying an electrical field to said target cell at a frequency of between 0.001 Hz to 1000 Hz at 0.002 mV/mm to 5 mV/mm for about 1 to about 5 minutes.

3. The method of claim 2, wherein said electric field is a uniform electric potential field.

4. The method of claim 1, wherein electrically stimulating said target cell comprises applying patterned pulses.

5. The method of claim 1, wherein electrically stimulating said target cell comprises electrically stimulating an organ or portion of an organ containing said target cell.

6. The method of claim 1, wherein electrically stimulating said target cell comprises stimulating a brain slice in vitro.

7. The method of claim 1, wherein said target cell is a central nervous system glial cell.

8. The method of claim 1, wherein said target cell is an astrocyte.

9. The method of claim 1, wherein said target cell is a cancer cell.

10. The method of claim 1, wherein said target cell is a central nervous system neuron.

* * * * *